(12) United States Patent
Sayeski et al.

(10) Patent No.: US 8,367,078 B2
(45) Date of Patent: Feb. 5, 2013

(54) KINASE INHIBITOR COMPOUNDS

(75) Inventors: Peter P. Sayeski, Gainesville, FL (US); György M. Keserü, Telki (HU)

(73) Assignee: University of Florida Research Foundation, Inc., Gainesville, FL (US)

( * ) Notice: Subject to any disclaimer, the term of this patent is extended or adjusted under 35 U.S.C. 154(b) by 216 days.

(21) Appl. No.: 12/663,521

(22) PCT Filed: Jun. 5, 2008

(86) PCT No.: PCT/US2008/007073
§ 371 (c)(1), (2), (4) Date: Jul. 12, 2010

(87) PCT Pub. No.: WO2008/153900
PCT Pub. Date: Dec. 18, 2008

(65) Prior Publication Data
US 2010/0278933 A1    Nov. 4, 2010

Related U.S. Application Data

(60) Provisional application No. 60/933,449, filed on Jun. 6, 2007.

(51) Int. Cl.
| | |
|---|---|
| A61K 9/00 | (2006.01) |
| A61K 47/00 | (2006.01) |
| A61K 9/48 | (2006.01) |
| A61K 9/20 | (2006.01) |
| A61K 33/42 | (2006.01) |
| A01N 59/26 | (2006.01) |
| G01N 33/20 | (2006.01) |
| C07C 255/00 | (2006.01) |
| C07C 49/20 | (2006.01) |
| C07F 9/22 | (2006.01) |

(52) U.S. Cl. ........ 424/400; 424/439; 424/451; 424/463; 424/464; 424/489; 424/601; 436/81; 558/303; 558/385; 562/8; 562/11; 568/8; 568/303; 568/307; 568/382; 568/414; 568/415; 568/700; 568/702

(58) Field of Classification Search .............. 424/400, 424/439, 451, 463, 464, 489, 601; 436/81; 558/303, 385; 562/8, 11; 568/8, 303, 307, 568/382, 414, 415, 700, 702
See application file for complete search history.

(56) References Cited

U.S. PATENT DOCUMENTS

| | | | |
|---|---|---|---|
| 5,972,978 | A | 10/1999 | Andersen et al. |
| 7,632,651 | B2 * | 12/2009 | Boge et al. .................. 435/7.4 |
| 2006/0166936 | A1 | 7/2006 | Binch et al. |
| 2006/0288432 | A1 | 12/2006 | Vainchenker et al. |
| 2007/0015752 | A1 | 1/2007 | Hangauer, Jr. |

OTHER PUBLICATIONS

International Search Report for related PCT application, PCT/US08/07073, dated Aug. 29, 2008.
International Preliminary Report on Patentability dated Aug. 29, 2008 for related PCT application PCT/US08/07073.

* cited by examiner

*Primary Examiner* — Richard Schnizer
*Assistant Examiner* — Jane C Oswecki
(74) *Attorney, Agent, or Firm* — Edwards Wildman Palmer LLP; Jeffrey D. Hsi; Mark D. Russett

(57) ABSTRACT

The invention relates to kinase inhibitor compounds and methods of identifying and using them. The invention further relates to pharmaceutical compositions and methods for treating disorders, especially cancer.

26 Claims, 36 Drawing Sheets

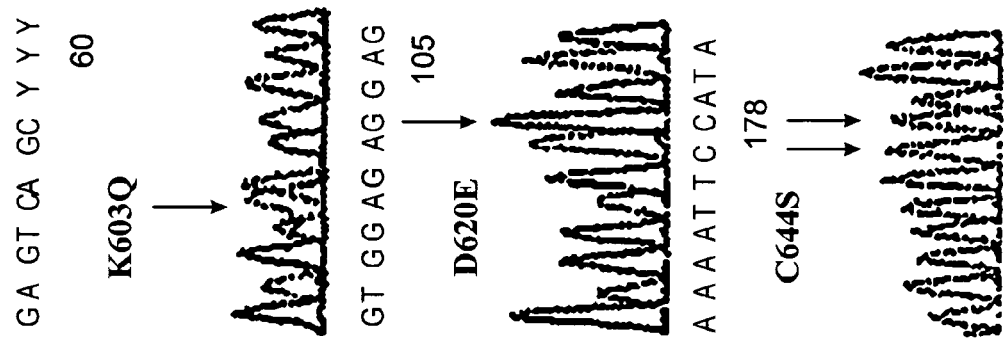
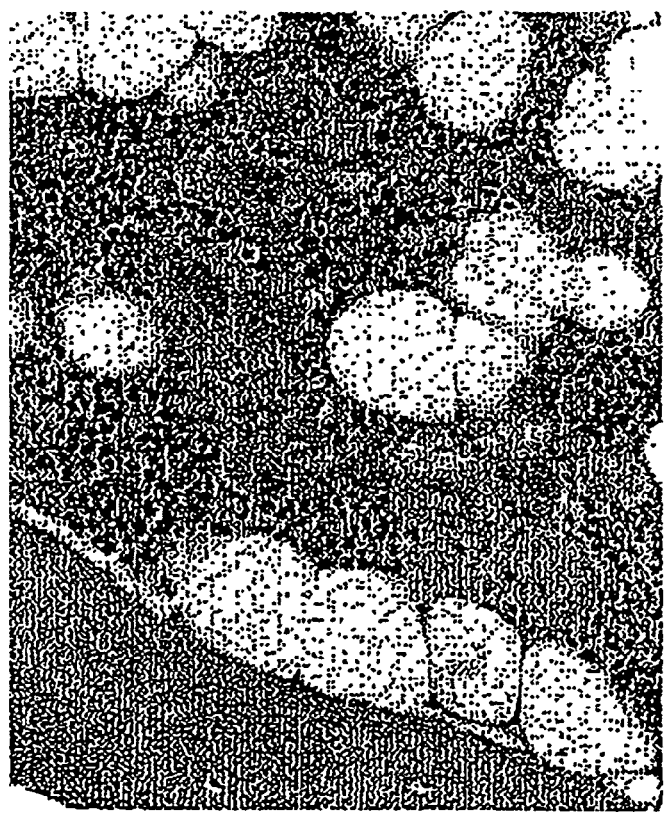
FIG. 1B
FIG. 1A

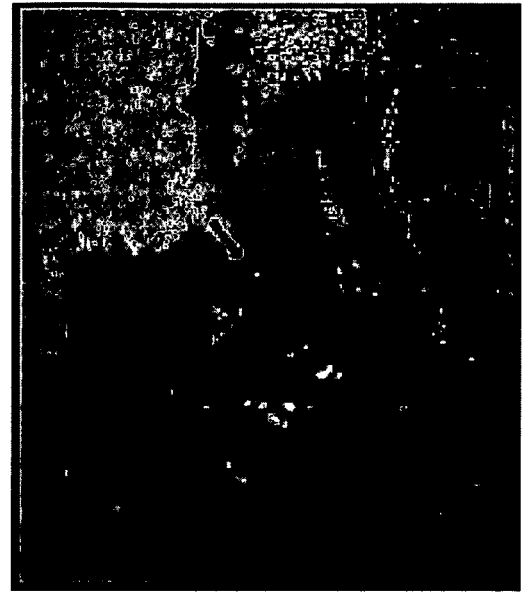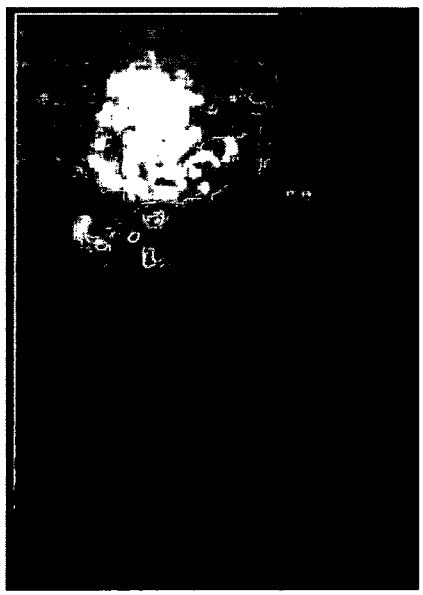
Gross Anatomy of Some Skin Tumors
No correlation between G6 treatment and tumor size
FIG. 15

| Compound | Structure | % Growth Inhibition | Aqueous Solubility (μM) |
|---|---|---|---|
| G6 (Lead Compound) | 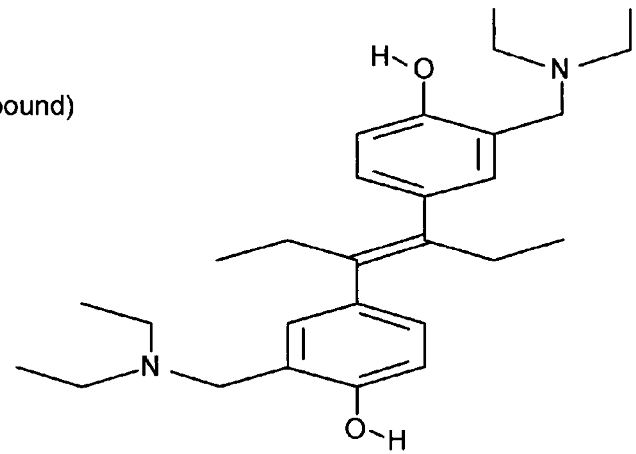 | 100 | 497.5 |
| D1 | 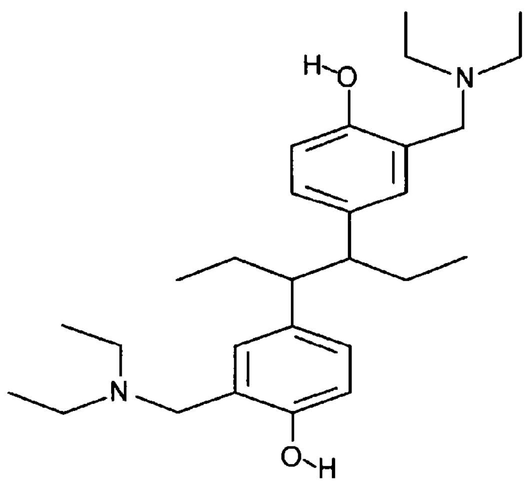 | 81.57 | 374.3402778 |

FIG. 17A 396.1979167
361.9583333
85.45
22.65
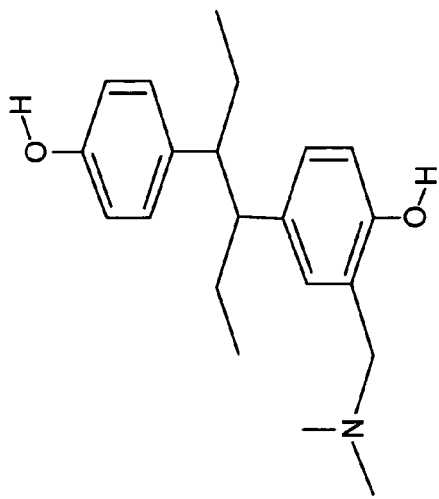
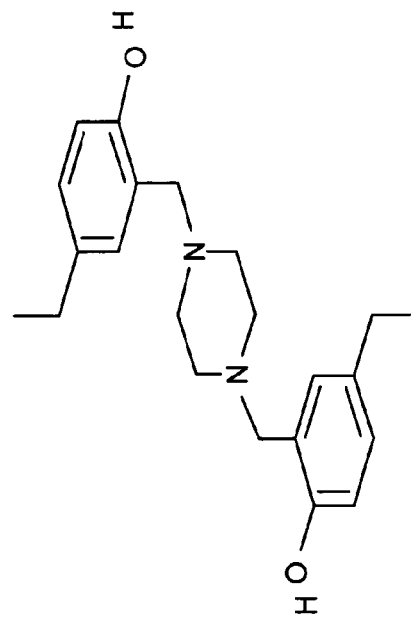
D4
D5
FIG. 17C Growth inhibition and aqueous solubility assays could not be done.
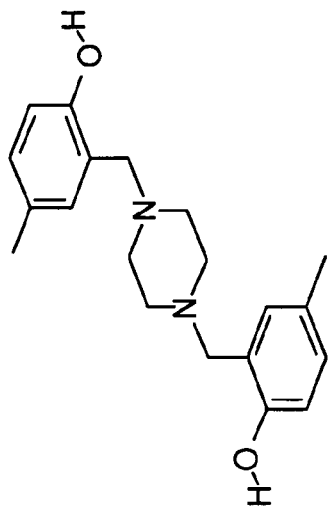
D6
Was not soluble in DMSO at 10 mM.
256.8402778
79.85
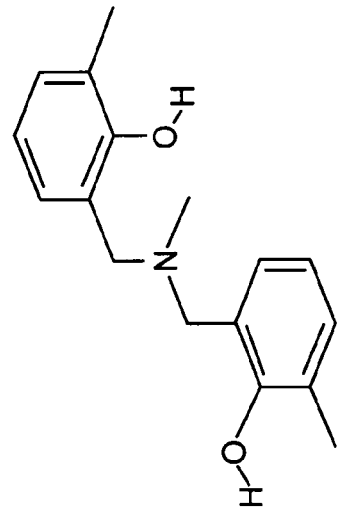
D7
FIG. 17D 361.9212963
14.97916667
53.17
49.14
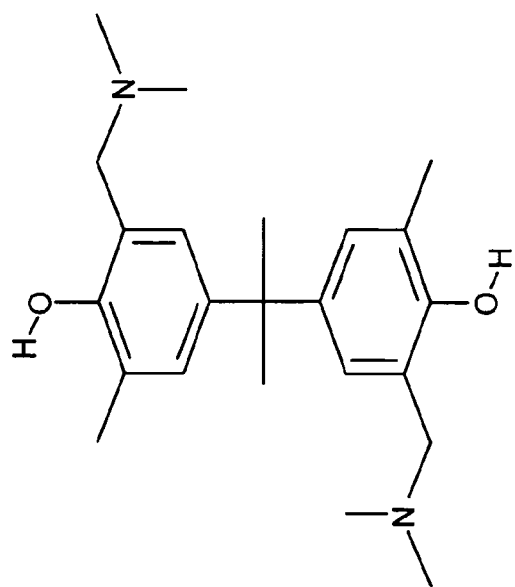
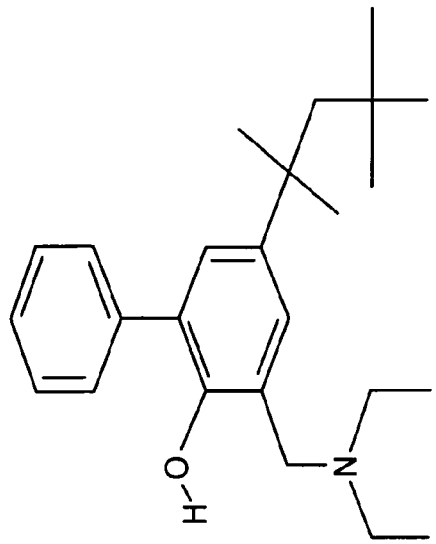
D8
D9
FIG. 17E 186.2083333
394.21875
24.38
0.77
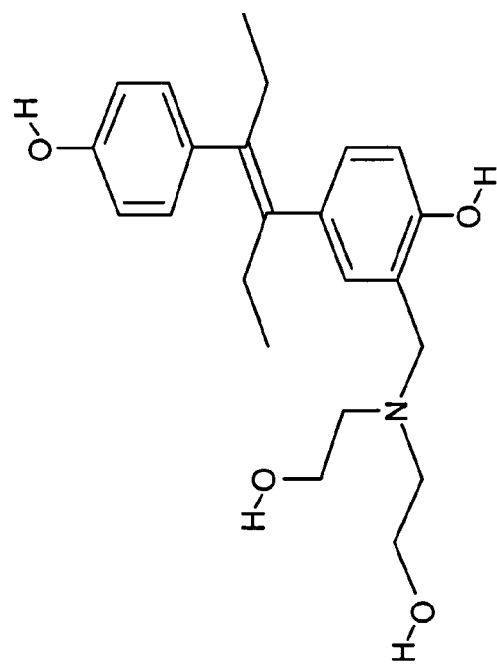
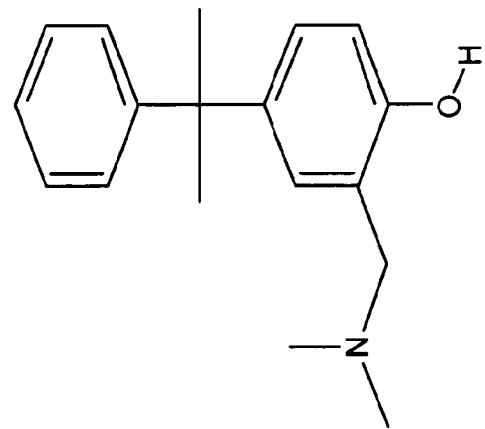
D10
D11
FIG. 17F FIG. 17G
21.125  15.55
164.1898148  28.79
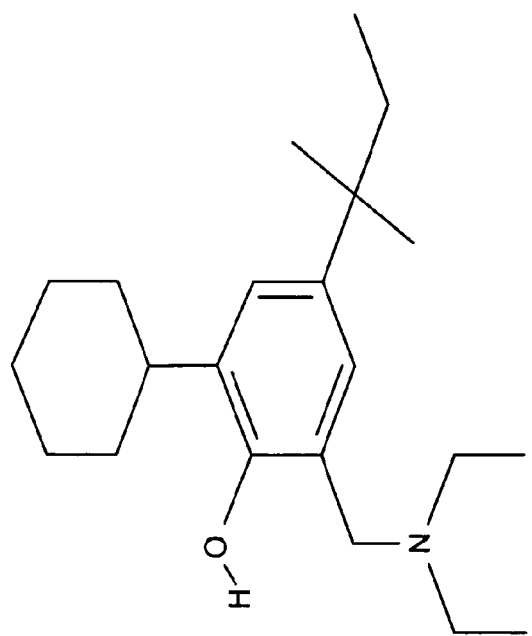
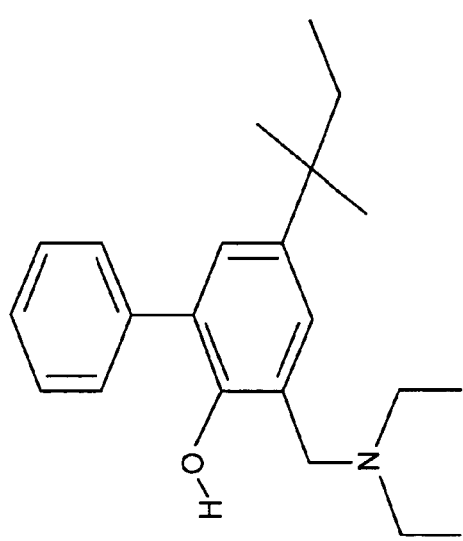
D12
D13

81.45833333
39.73
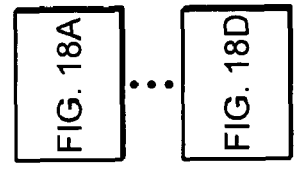
FIG. 17H
FIG. 18
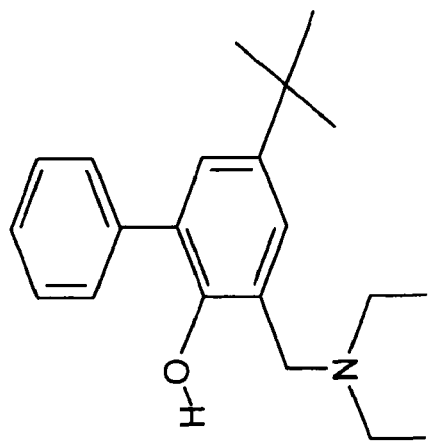
D14

| Compound | Structure | % Growth Inhibition | Aqueous Solubility (µM) |
|---|---|---|---|
| G6 Lead Compound | | 100 | 468.194 |
| D21 | 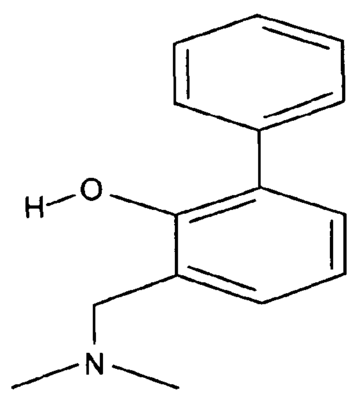 | -5 | 458.185 |

Statistical significance between DMSO and G13; (p=0.052)
Statistical significance between DMSO and G11; (p=0.00000000752)
Statistical significance between DMSO and G6; (p=2.98 x 10$^{-25}$)

FIG. 23

US 8,367,078 B2

KINASE INHIBITOR COMPOUNDS

RELATED APPLICATIONS

This application is the national stage application pursuant to 35 U.S.C. §371 of PCT application PCT/US2008/007073, filed Jun. 5, 2008, which claims the benefit of U.S. Provisional Application No. 60/933,449, filed Jun. 6, 2007. The entire contents of the aforementioned applications are hereby incorporated herein by reference.

STATEMENT OF RIGHTS TO INVENTIONS MADE UNDER FEDERALLY SPONSORED RESEARCH

This work was supported in part by a National Institutes of Health/NHLBI Grant, Grant No. R01-HL67277. The government may have certain rights in the invention.

SEQUENCE LISTING

The instant application contains a Sequence Listing which has been submitted via EFS-Web and is hereby incorporated by reference in its entirety. Said ASCII copy, created on Jul. 6, 2010, is named 68387491.txt and is 7,318 bytes in size.

FIELD OF THE INVENTION

The present invention relates to compounds that are capable of modulating Jak2 binding interactions. The compounds thus have therapeutic use in treating a subject suffering from or susceptible to a JAK-2 mediated disorder.

BACKGROUND OF THE INVENTION

Protein kinases constitute a large family of structurally related enzymes that are responsible for the control of a variety of signal transduction processes within the cell. (See, Hardie, G. and Hanks, S. The Protein Kinase Facts Book, I and II, Academic Press, San Diego, Calif.: 1995). The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., FASEB J. 1995, 9, 576-596; Knighton et al., Science 1991, 253, 407-414; Hiles et al., Cell 1992, 70, 419-429; Kunz et al., Cell 1993, 73, 585-596; Garcia-Bustos et al., EMBO J. 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli (e.g., environmental stress, chemical stress, signaling by agents including e.g., cytokines and growth factors).

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [Frank Mol. Med. 5, 432-456 (1999) & Seidel, et al., Oncogene 19, 2645-2656 (2000)].

JAK1, JAK2, and TYK2 are ubiquitously expressed, while JAK3 is predominantly expressed in hematopoietic cells. JAK3 binds exclusively to the common cytokine receptor gamma-chain and is activated by IL-2, IL-4, IL-7, IL-9, and IL-15. The proliferation and survival of murine mast cells induced by IL-4 and IL-9 have, in fact, been shown to be dependent on JAK3- and .gamma-chain-signaling [Suzuki et al, Blood 96, 2172-2180 (2000)].

While to date certain Jak2 inhibitor compounds are being considered for therapeutic use, these compounds suffer limitations due, in part, to their lack of target specificity. As such, there is a need for therapeutic agents that are useful in mediating Jak2-mediated disease but are devoid of the side effect and selectivity limitations of existing agents.

SUMMARY OF THE INVENTION

The subject matter herein provides compounds and methods of using such compounds for treatment of disease and disorders, or symptoms thereof, in a subject.

It has been demonstrated that these compounds can block Jak2 kinase activity in culture cells in vitro, in bone marrow samples derived from human patients harboring known Jak2 mutations ex vivo, and in a mouse model of a Jak2-mediated erythroleukemia, in vivo. Specifically, the compound termed G6 blocked Jak2 kinase activity with an IC50 of approximately 50 nM. G6 inhibited the cytokine independent growth of stem cell cells derived from either polycythemia vera or essential thrombocythemia patients carrying known pathologic Jak2 mutations. G6 also reduced the percentage of blasts cells and the number of nucleated red blood cells in a mouse model of Jak2-mediated erythroleukemia. Finally, structure/function analysis of the G6 lead compound has identified the regions of G6 that mediate Jak2 inhibition versus those that mediate aqueous solubility.

In a first aspect, the invention features a method of treating or preventing a JAK2 mediated disorder in a subject comprising: administering to the subject identified as in need thereof a compound selected from Table 1 or a salt, hydrate or solvate thereof.

In one embodiment, the compound is 2-(diethylaminomethyl)-4-[4-[3-(diethylaminomethyl)-4-hydroxy-phenyl]hex-3-en-3-yl]phenol (G6), or a derivative thereof.

In another embodiment, the G6 derivative is a compound selected from Table 2 or a salt, hydrate or solvate thereof.

In a further related embodiment, the subject is administered an additional therapeutic agent. In still another related embodiment, the compound and the additional therapeutic agent are administered simultaneously. In a further embodiment, the compound and the additional therapeutic agent are administered sequentially.

In another embodiment, the JAK2 mediated disorder is a hematological disease or disorder. In a related embodiment, the hematological disease or disorder is selected from the group consisting of polycythemia vera, essential thrombocythemia, angiogenic myeloid metaplasia, and primary myelofibrosis.

In another embodiment, the JAK2 mediated disorder is cancer. In a related embodiment, the cancer is selected from the group consisting of leukemias, lymphomas, myelomas, and solid tumors. In a further embodiment, the leukemia is selected from the group consisting of chronic myelogenous leukemia (CML), acute myeloid leukemia (AML) and acute promyelocytic leukemia (APL).

In another embodiment, the JAK2 mediated disorder is a cardiac disease or disorder. In a related embodiment, the cardiac disease or disorder is selected from the group consisting of cardiac hypertrophy, cardiac ischemia-reperfusion, and heart failure.

In a further embodiment of any one of the above aspects, the compound selected from Table 1 or Table 2, or salt, hydrate or solvate thereof is an inhibitor of the Jak2-V617F mutant.

In another further embodiment of any one of the above aspects, the compound selected from Table 1 or Table 2, or a salt, hydrate or solvate thereof, inhibits Jak2 autophosphorylation.

In another embodiment, the compound selected from Table 1 or Table 2, or salt, hydrate or solvate thereof does not inhibit c-Src or Tyk2 autophosphorylation as effectively as Jak2 autophosphorylation.

In still another embodiment, the compound is selected from the group consisting of G6, G13, G31, G33 or G40.

In another embodiment, the compound is selected from the group consisting of D4, D5, D28 and D30.

In another aspect, the invention features a method of treating cancer in a subject comprising administering to the subject identified as in need thereof a compound of Table 1 or a salt, hydrate or solvate thereof.

In one embodiment, the cancer is selected from the group consisting of leukemias, lymphomas, myelomas, and solid tumors. In a related embodiment, the leukemia is selected from the group consisting of chronic myelogenous leukemia (CML), acute myeloid leukemia (AML) and acute promyelocytic leukemia (APL).

In another aspect, the invention features a method of treating a hematological disease or disorder in a subject comprising administering to the subject identified as in need thereof a compound of Table 1 or a salt, hydrate or solvate thereof.

In one embodiment, the cardiac disease or disorder is selected from the group consisting of cardiac hypertrophy, cardiac ischemia-reperfusion, and heart failure.

In still another aspect, the invention features a method for reducing Jak2-dependent cell growth comprising contacting a cell with a Jak-2 inhibitor compound.

In another further aspect, the invention features a method of inhibiting JAK2 in a subject identified as in need of such treatment, comprising administering a compound of Table 1 or a salt, hydrate or solvate thereof.

In one embodiment of any one of the above aspects, the compound is 2-(diethylaminomethyl)-4-[4-[3-(diethylaminomethyl)-4-hydroxy-phenyl]hex-3-en-3-yl]phenol (G6), or a derivative thereof. In a further embodiment, the G6 derivative is a compound selected from Table 2, or a salt, hydrate or solvate thereof. In another further embodiment, the G6 derivative compound is selected from the group consisting of D4, D5, D28 and D30.

In one embodiment of any one of the above aspects, the compound selected from Table 1 or Table 2, or a salt, hydrate or solvate thereof, is an inhibitor of the Jak2-V617F mutant.

In another embodiment of any one of the above aspects, the compound selected from Table 1 or Table 2, or a salt, hydrate or solvate thereof, inhibits Jak2 autophosphorylation.

In one embodiment, the compound selected from Table 1 or Table 2, or a salt, hydrate or solvate thereof does not inhibit c-Src or Tyk2 autophosphorylation as effectively as Jak2 autophosphorylation.

In another embodiment of any one of the above aspects, the subject is identified as having the Jak2-V617F mutant.

In another embodiment of any one of the above aspects, the subject is identified as having the K603Q, D620E or C644S mutation in the Jak2 JH2 domain.

In still another embodiment of any one of the above aspects, the subject is identified as having the K603Q, D620E and C644S mutations in the Jak2 JH2 domain.

In another embodiment of any one of the above aspects, the subject is identified as having the K603Q, D620E and C644S mutations in the Jak2 JH2 domain and is identified as not having the Jak2-V617F mutant.

In yet another embodiment of any one of the above aspects, the subject is a human.

In another aspect, the invention features a composition comprising a compound capable of modulating Jak2 activity selected from one or more compounds listed in Table 1 or Table 2, or a salt, hydrate or solvate thereof.

In one embodiment, the modulation is an inhibition of Jak2 activity.

In another aspect, the invention features a pharmaceutical composition comprising a compound capable of modulating Jak2 activity selected from one or more compounds listed in Table 1 or Table 2, or a pharmaceutically acceptable ester, salt, or prodrug thereof, together with a pharmaceutically acceptable carrier.

In still another aspect, the invention features a kit comprising a compound capable of modulating Jak2 activity selected from one or more compounds listed in Table 2, and instructions for use in treating cancer.

In another aspect, the invention features a kit comprising a compound capable of modulating Jak2 activity selected from one or more compounds listed in Table 2, and instructions for use in treating a hematological disorder.

In still another aspect, the invention features a kit comprising a compound capable of modulating Jak2 activity selected from one or more compounds listed in Table 2, and instructions for use in treating a cardiac disorder.

In another aspect, the invention features a kit comprising a compound capable of modulating Jak2 activity selected from one or more compounds listed in Table 2, and instructions for use in reducing Jak2-dependent cell growth.

The invention also provides a pharmaceutical compositions of the compounds described herein, comprising a compound herein, or a pharmaceutically acceptable ester, salt, or prodrug thereof, together with a pharmaceutically acceptable carrier.

The invention also provides methods for designing, evaluating and identifying compounds which bind to the aforementioned binding pockets. Other embodiments of the invention are disclosed infra.

BRIEF DESCRIPTION OF THE DRAWINGS

The present invention is further described below with reference to the following non-limiting examples and with reference to the following figures, in which:

FIG. 15 are photographs showing the gross anatomy of skin tumors.

FIG. 17B is a table showing the percent growth inhibition and aqueous solubility of the G6 derivative compound D14.

FIG. 18A is a table showing the percent growth inhibition and aqueous solubility of G6 and the G6 derivative compound D21.

FIG. 23 shows the interactions of G6, D4 and D5 with the activation loop of Jak2.

DETAILED DESCRIPTION OF THE INVENTION

Figure 1C:
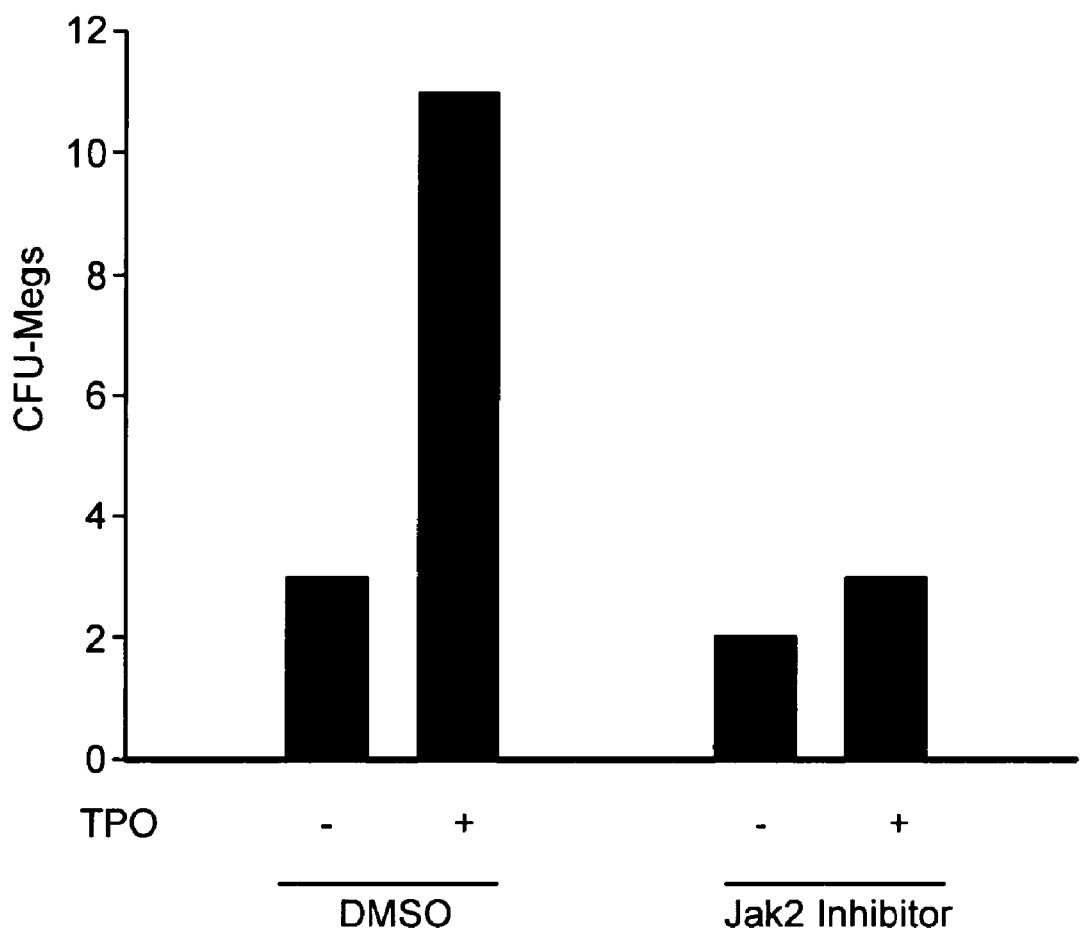
FIG. 1($a$-$c$) depicts: (a) Bone marrow biopsy (H&E×400) showing clustered, atypical megakaryocytes in background normocellular marrow with no significant increase in reticulin fibrosis. (b) Sequence chromatograms showing the K603Q (top (SEQ ID NO: 5)), D620E (middle (SEQ ID NO: 6)), and C644S (bottom (SEQ ID NO: 7)) mutations. The nucleotide changes for each of the three mutations are as follows: K603Q, aag→cag; D620E, gac→gag; C644S, tgt→tcc. (c) $10^5$ cells were re-suspended in methylcellulose containing media and seeded in 35 mm dishes containing either DMSO (0.25% vol/vol) or 3-[5-[(4-oxo-4-phenyl-butan-2-ylidene)amino]pentylimino]-1-phenyl-butan-1-one (25 μM final). Some cultures were also supplemented with human thrombopoietin (50 ng/ml). Cultures were grown in a humidified environment at 37° C. with 5% $CO_2$ and CFU-Megs were counted thirteen days later.
Figure 2:
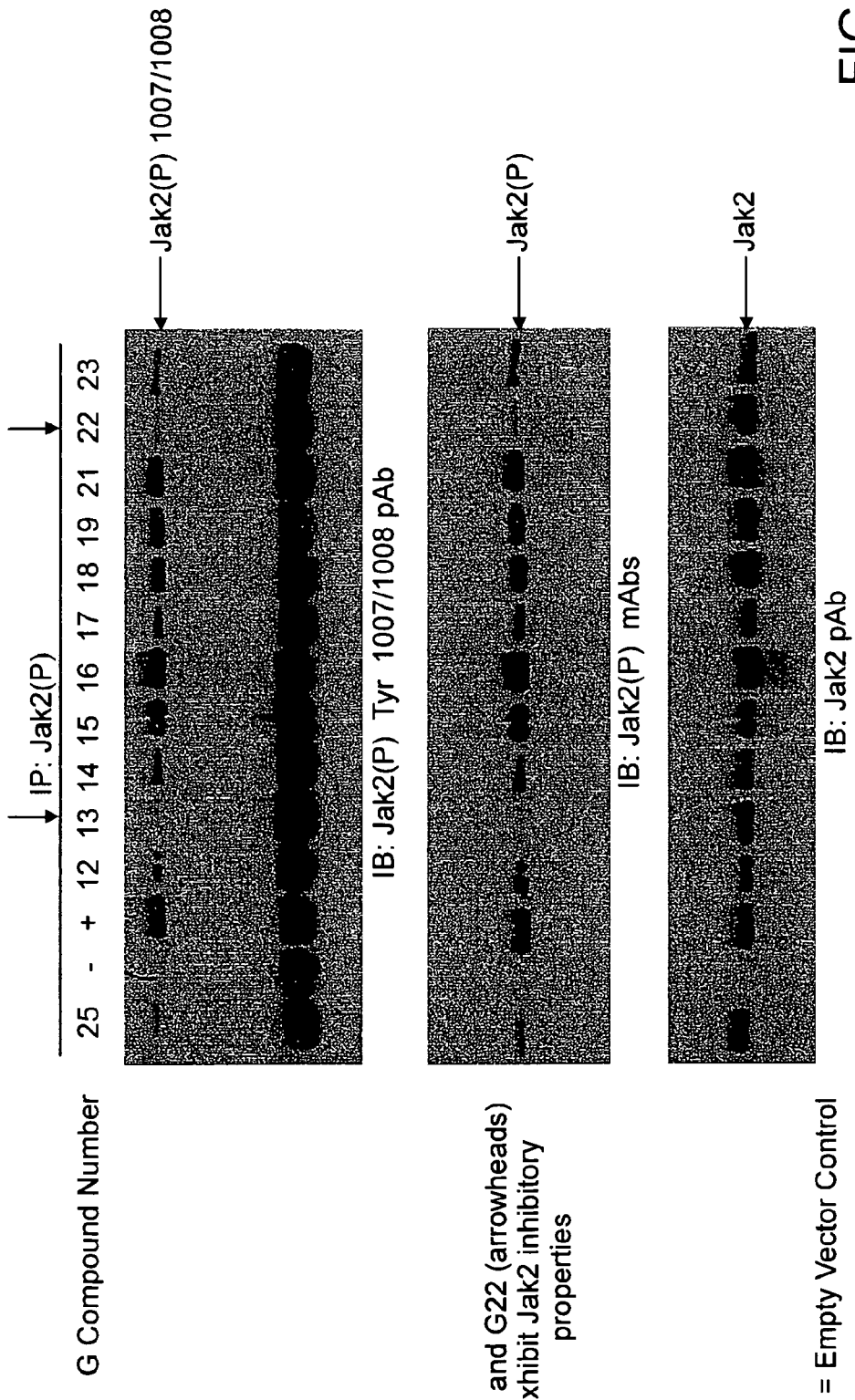
FIG. 2 depicts the results of Jak2-WT (wild type) ability to autophosphorylate in the presence of various test compounds.
Figure 3:
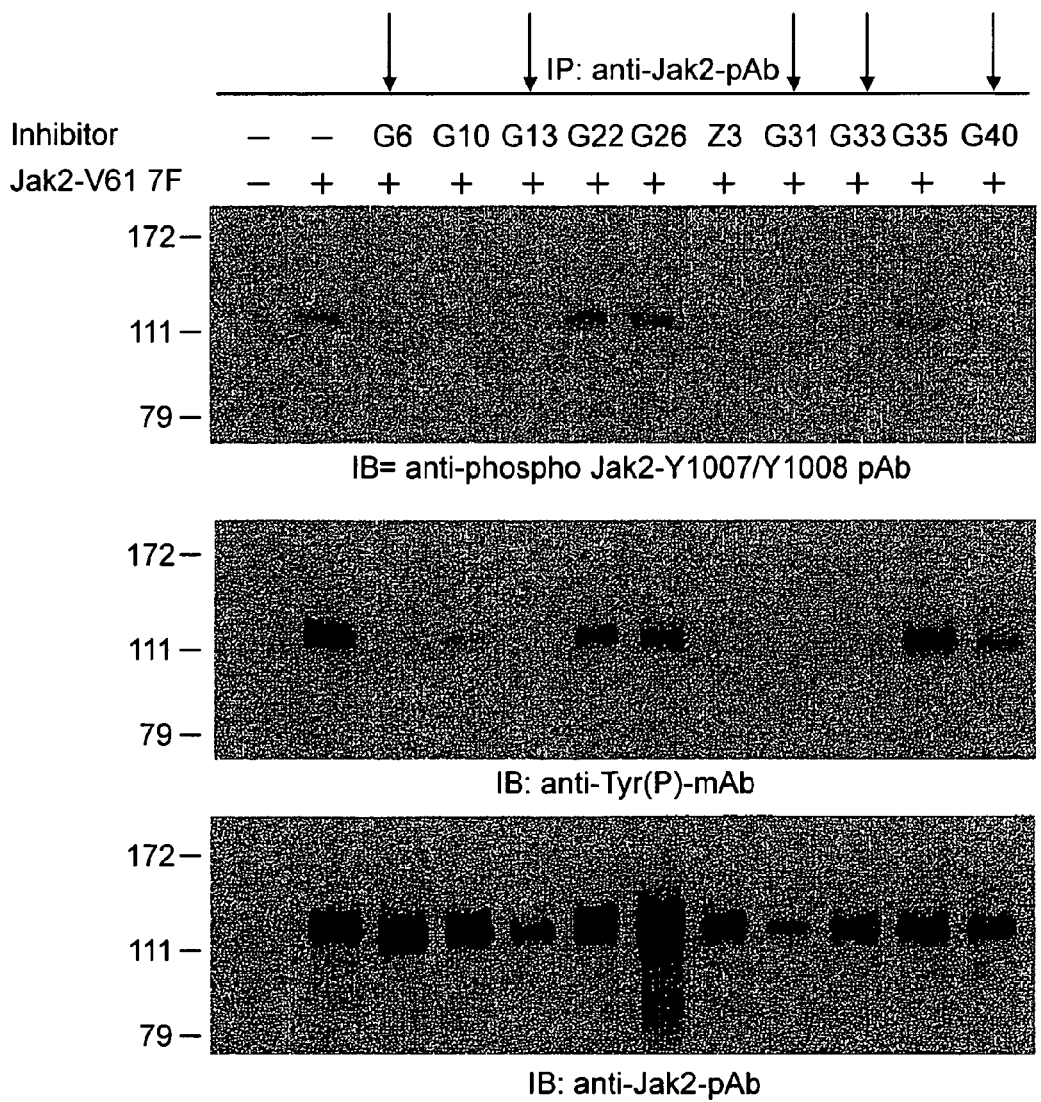
FIG. 3 depicts the results of Jak2-V617F (mutant) ability to autophosphorylate in the presence of various test compounds.
Figure 4:
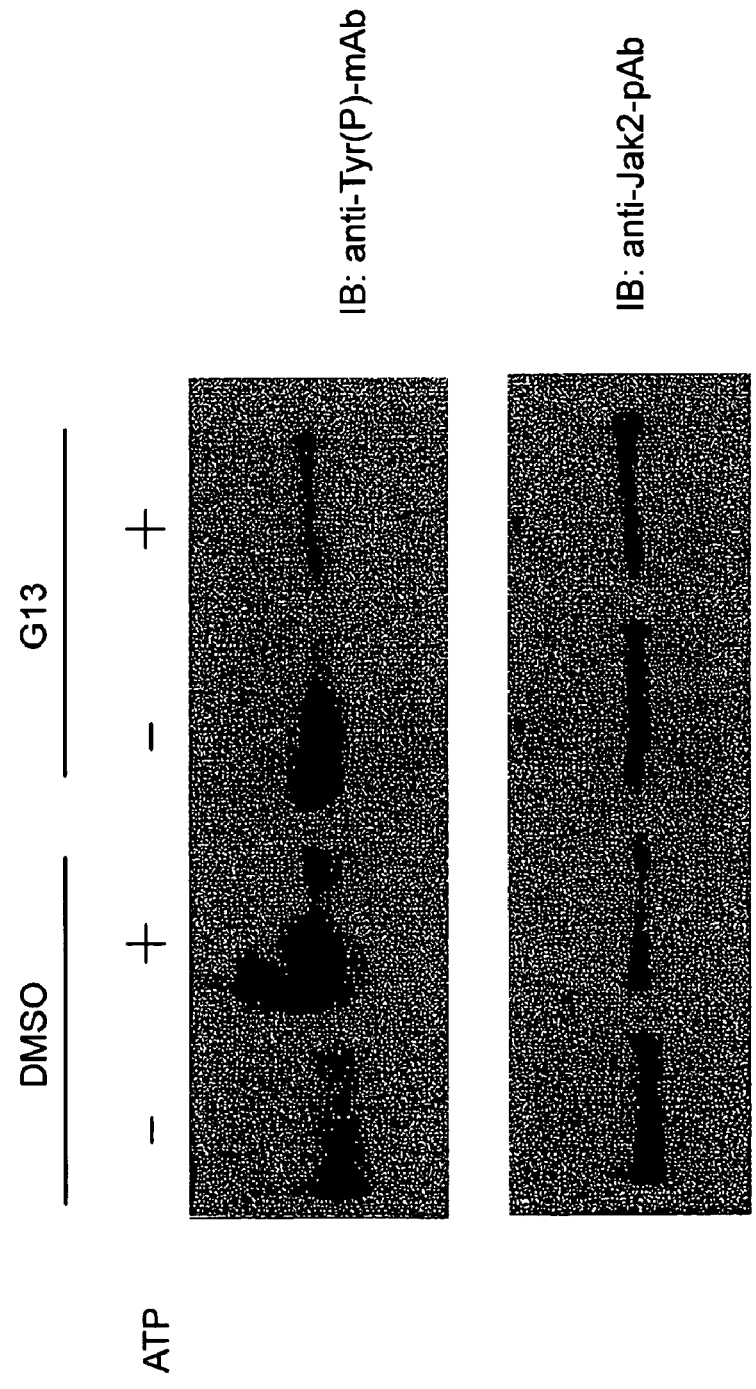
FIG. 4 depicts the results demonstrating that G13 is a direct inhibitor of Jak2.
Figure 5:
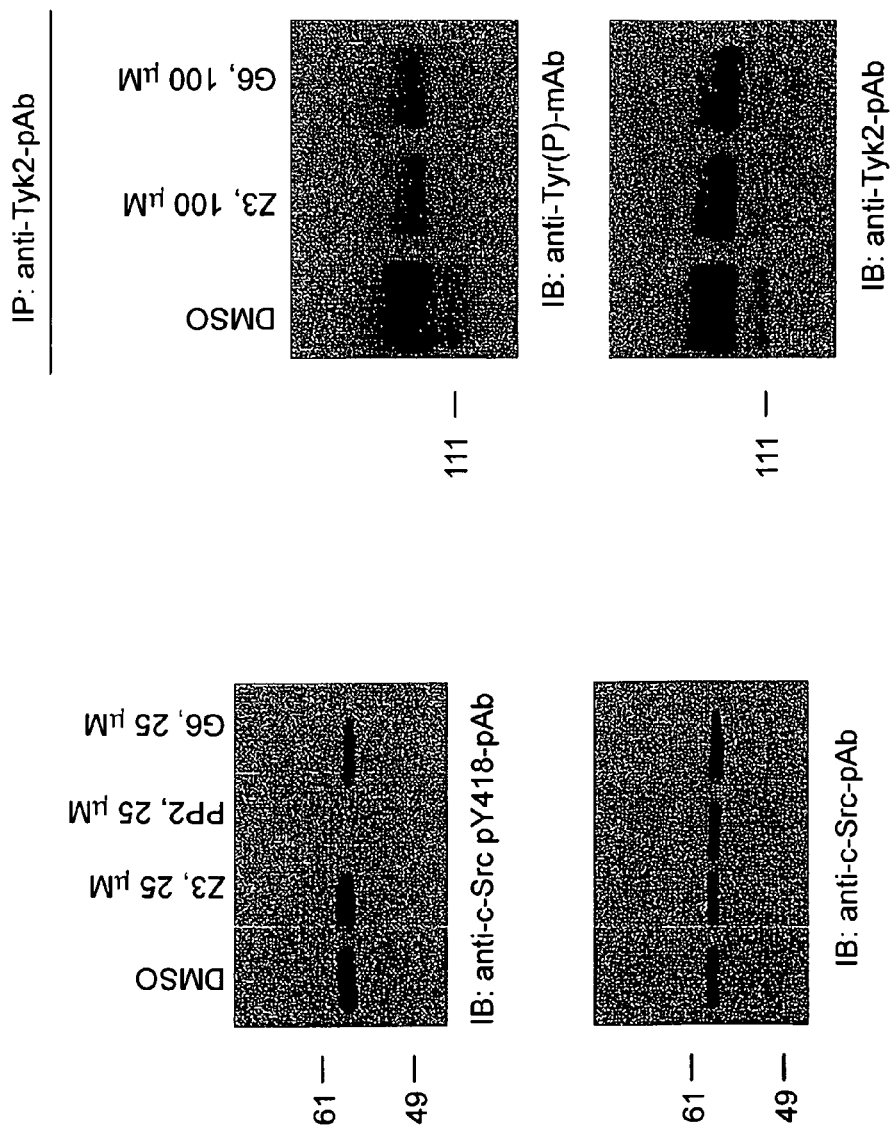
FIG. 5 depicts the results demonstrating the selectivity of test compounds for Jak2 over c-Src and Tyk2 kinase activity on autophosphorylation.
Figure 6:
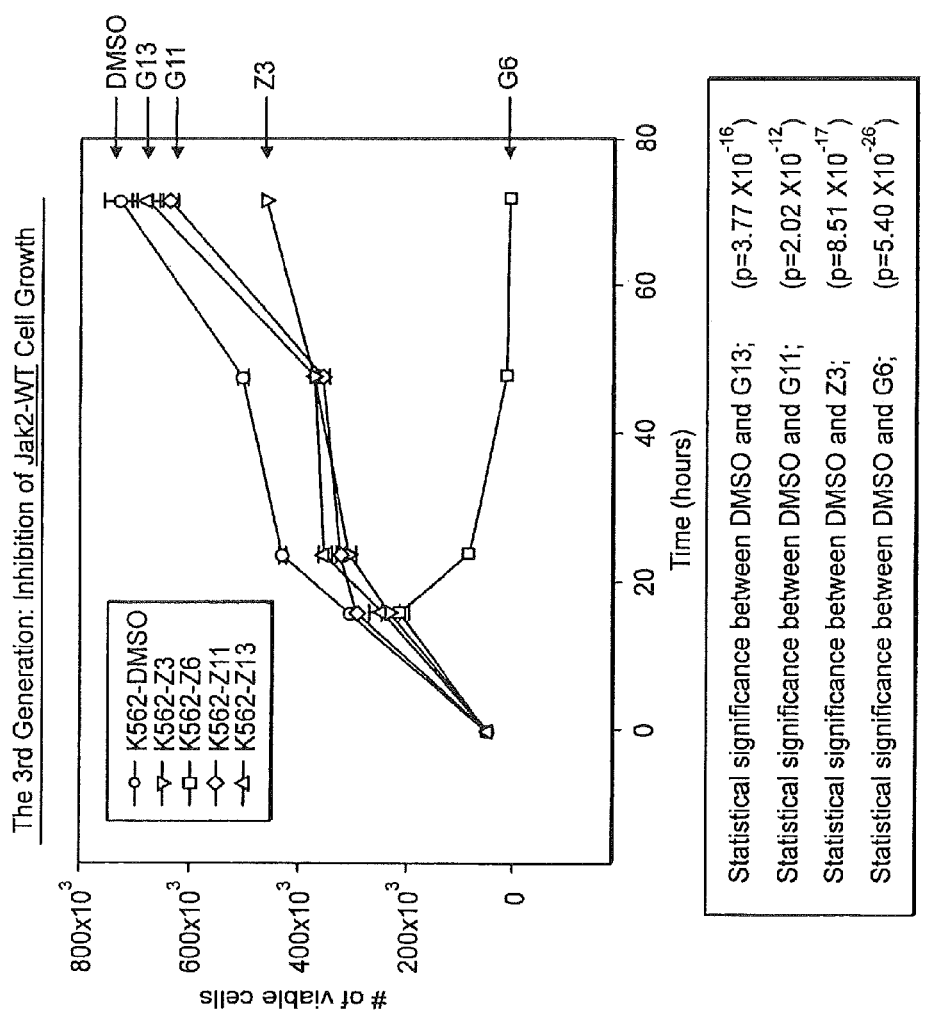
FIG. 6A depicts results showing inhibition of Jak2-WT cell growth.
FIG. 6B shows the statistical significance of the results shown in FIG. 6A.
Figure 7:
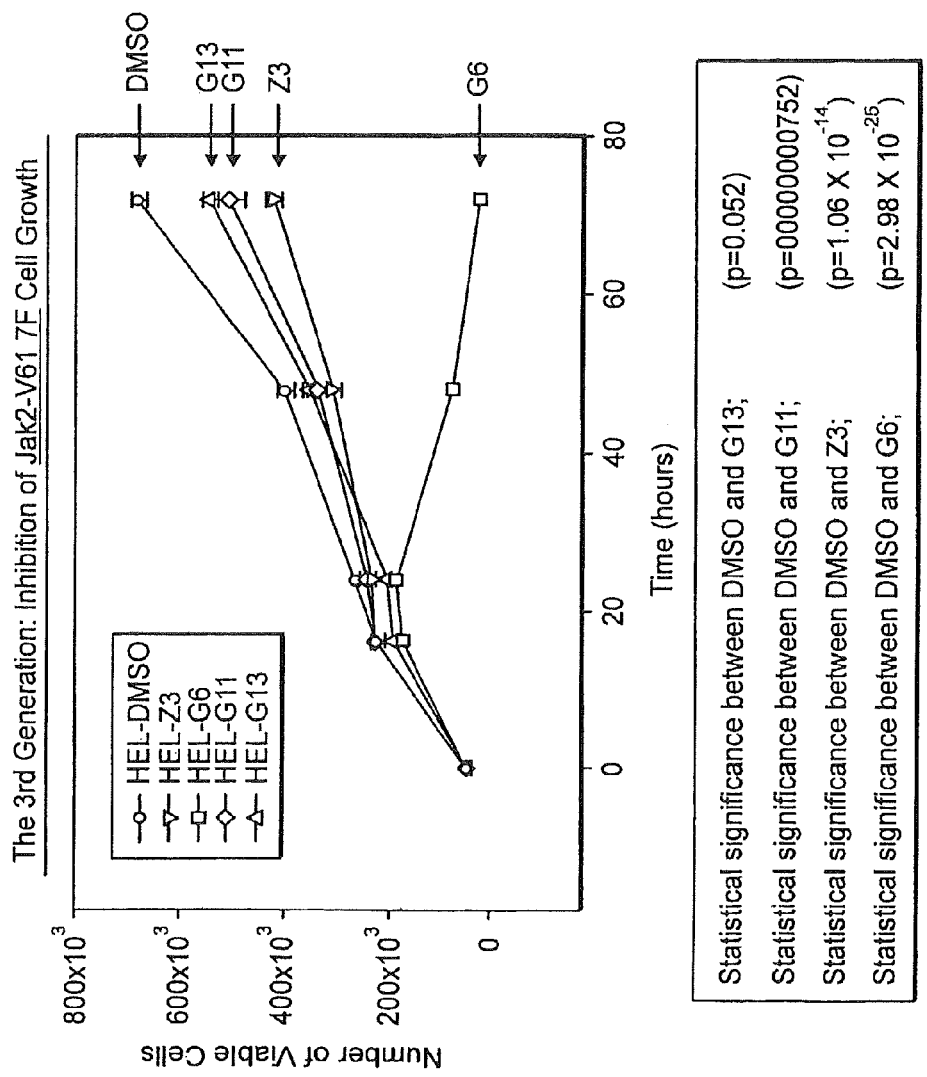
FIG. 7A depicts results showing inhibition of Jak2-V617F cell growth.
FIG. 7B shows the statistical significance of the results shown in FIG. 7A.

The present inventors have now discovered a therapeutic strategy that addresses inhibition of Jak2 and Jak2 mutations by targeting Jak2 interactions. Such interactions are relevant for modulation of Jak2-mediated disease, particularly in certain proliferation disease types where Jak2 and Jak2 mutant mechanisms play a significant role.

The present invention also relates, at least in part, to the discovery that the compounds delineated herein demonstrate selective interactions with certain targets (e.g., selective for Jak2 or Jak 2 mutants) for disease therapy.

1. DEFINITIONS

Before further description of the present invention, and in order that the invention may be more readily understood, certain terms are first defined and collected here for convenience.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally effect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The phrase "in combination with" is intended to refer to all forms of administration that provide an a compound of the invention (e.g. a compound selected from Table 1 or Table 2) together with a second agent, such as a second compound selected from Table 1 or Table 2_therapeutic agent, where the two are administered concurrently or sequentially in any order.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., C1-C30 for straight chain, $C_3$-$C_{30}$ for branched chain), preferably 26 or fewer, and more preferably 20 or fewer, and still more preferably 4 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl i-propyl, tert-butyl, hexyl, heptyl, octyl and so forth. In preferred embodiment, the term "lower alkyl" includes a straight chain alkyl having 4 or fewer carbon atoms in its backbone, e.g., C1-C4 alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "associating with" refers to a condition of proximity between a chemical entity or compound, or portions thereof, and a binding pocket or binding site on a protein. The association may be non-covalent (wherein the juxtaposition is energetically favored by hydrogen bonding or van der Waals or electrostatic interactions) or it may be covalent.

The term "binding pocket", as used herein, refers to a region of a molecule or molecular complex, that, as a result of its shape, favorably associates with another chemical entity or compound.

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In a preferred embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In preferred embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "effective amount" includes an amount effective, at dosages and for periods of time necessary, to achieve the desired result, e.g., sufficient to treat a disorder delineated herein. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

The language "therapeutically effective amount" of a compound of the invention of the invention refers to an amount of an agent which is effective, upon single or multiple dose Jak2-mediated disorder, or in prolonging the survivability of the patient with such a Jak2-mediated disorder beyond that expected in the absence of such treatment.

A therapeutically effective amount of compound of the invention (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. In one example, a subject is treated with a compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound of the invention used for treatment may increase or decrease over the course of a particular treatment.

By "agent" is meant a polypeptide, polynucleotide, or fragment, or analog thereof, small molecule, or other biologically active molecule.

The term "enantiomers" refers to two stereoisomers of a compound which are non-superimposable mirror images of one another. An equimolar mixture of two enantiomers is called a "racemic mixture" or a "racemate."

The term "haloalkyl" is intended to include alkyl groups as defined above that are mono-, di- or polysubstituted by halogen, e.g., fluoromethyl and trifluoromethyl.

The term "halogen" designates —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The term "hematological disease or disorder" is meant to refer to a disease or disorder of the blood or blood forming tissues.

The term "cancer' is meant to refer to any disease that is caused by or results in inappropriately high levels of cell division, inappropriately low levels of apoptosis, or both.

Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphomas (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

The phrase "treating cancer" refers to the killing of malignant, or cancerous, cells. By treating is meant causing in the subject cell death in the tumor. Alternatively, "treating" cancer means arresting or otherwise ameliorating symptoms of cancer in the subject.

The language "improved biological properties" refers to any activity inherent in a compound of the invention that enhances its effectiveness in vivo. In a preferred embodiment, this term refers to any qualitative or quantitative improved therapeutic property of a compound of the invention, such as reduced toxicity.

The term "cell proliferative disorder" includes disorders involving the undesired or uncontrolled proliferation of a cell. Examples of such disorders include, but are not limited to, tumors or cancers (e.g., solid tumors such as breast, ovarian, prostate, lung (small cell and non-small cell), thyroid, pancreatic, breast or colon), sarcoma, leukemia, myeloma, lymphoma, or melanoma.

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-($C_1$-$C_8$alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —CONH$_2$, mono- or di-($C_1$-$C_8$alkyl)aminocarbonyl, —SO$_2$NH$_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "isomers" or "stereoisomers" refers to compounds which have identical chemical constitution, but differ with regard to the arrangement of the atoms or groups in space.

The term "modulate" refers to an increase or decrease, e.g., in the ability of a cell to proliferate in response to exposure to a compound of the invention, e.g., the inhibition of proliferation of at least a sub-population of cells in an animal such that a desired end result is achieved, e.g., a therapeutic result. In certain preferred examples, the modulation is an inhibition. The term "inhibition" means decrease, suppress, attenuate, diminish, arrest, or stabilize the target activity, e.g. cell proliferation. In certain examples, the invention features compounds that modulate Jak2 activity.

The term "obtaining" as in "obtaining a compound" is intended to include purchasing, synthesizing or otherwise acquiring the compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "polycythemia vera" is meant to refer to a disease characterized by an abnormal increase in blood cells (primarily red blood cells) due to excess production of the cells by the bone marrow.

The term "essential thrombocythemia" is meant to refer to a blood disorder characterized by the overproduction of platelets by megakaryocytes in the bone marrow.

The term "primary myelofibrosis" is meant to refer to a disorder of the bone marrow, in which the marrow is replaced by fibrous (scar) tissue.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "a prophylactically effective amount" of a compound refers to an amount of a compound of the invention any formula herein or otherwise described herein which is effective, upon single or multiple dose administration to the patient, in preventing or treating a disorder delineated herein The language "reduced toxicity" is intended to include a reduction in any undesired side effect elicited by a compound of the invention when administered in vivo.

The term "sulfhydryl" or "thiol" means —SH.

The term "subject" includes organisms which are capable of suffering from a Jak2-mediated disorder or who could otherwise benefit from the administration of a compound of the invention of the invention, such as human and non-human animals. Preferred humans include human patients suffering from or prone to suffering from a Jak2-mediated disorder, disorder delineated herein, or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

The term "susceptible to a Jak2-mediated disorder" is meant to include subjects at risk of developing disorder of Jak2-mediated, e.g., Jak2-mediated, i.e., subjects suffering from Jak2-mediated, subjects having a family or medical history of Jak2-mediated disorder, and the like.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

With respect to the nomenclature of a chiral center, terms "d" and "l" configuration are as defined by the IUPAC Recommendations. As to the use of the terms, diastereomer, racemate, epimer and enantiomer will be used in their normal context to describe the stereochemistry of preparations.

2. COMPOUNDS OF THE INVENTION

In one aspect, the invention provides compounds capable of modulating (e.g., inhibiting or stimulating) (directly or indirectly) Jak2-binding activity and methods using the compounds thereof. Other aspects of the compounds and methods include those wherein the subject is identified as having the Jak2-V617F mutant; wherein the subject is identified as having the K603Q, D620E or C644S mutation in the Jak2 JH2 domain; wherein the subject is identified as having the K603Q, D620E and C644S mutations in the Jak2 JH2 domain; or wherein the subject is identified as having the K603Q, D620E and C644S mutations in the Jak2 JH2 domain and is identified as not having the Jak2-V617F mutant.

In one embodiment, the invention provides a compound capable of modulating Jak2-mediated protein binding; and pharmaceutically acceptable esters, salts, and prodrugs thereof.

Certain preferred compounds include compounds specifically delineated herein:

TABLE 1

Inhibitor Compounds 2-methyl-1-phenyl-4-pyridin-2-yl-2-(2-pyridin-2-ylethyl)butan-1-one;
3-[5-[(4-oxo-4-phenyl-butan-2-ylidene)amino]pentylimino]-1-phenyl-butan-1-one (G13);
2-(diethylaminomethyl)-4-[4-[3-(diethylaminomethyl)-4-hydroxy-phenyl]hex-3-en-3-yl]phenol (G6);
2-dibutoxyphosphoryloxypentanenitrile (G31);
ytterbium(+3) cation trihydroxide (G33); and
4-[(1S)-6,7-diethoxy-1,2,3,4-tetrahydroisoquinolin-1-yl]benzonitrile (G40).

The invention also relates to the pharmaceutically acceptable salts and esters of the above-mentioned compounds.

The invention also includes derivatives of 2-(diethylaminomethyl)-4-[4-[3-(diethylaminomethyl)-4-hydroxy-phenyl]hex-3-en-3-yl]phenol (G6). Table 2 lists exemplary G6 derivative compounds, although the invention is not limited to those compounds as shown below.

TABLE 2

G6 derivative compounds

G6 lead compound

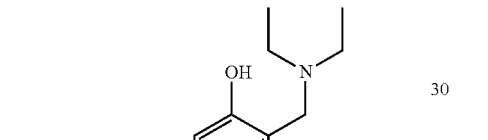

2-(diethylaminomethyl)-4-[4-[3-diethylaminomethyl)-4-hydroxy-phenyl]hex-3-en-3-yl]phenol

D1

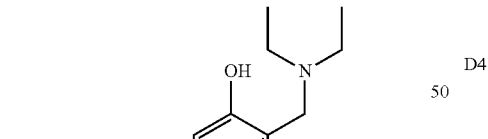

4,4'-(hexane-3,4-diyl)bis(2-((diethylamino)methyl)phenol)

TABLE 2-continued

G6 derivative compounds

D2

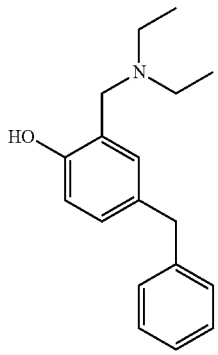 [SMILES: CCN(CC)Cc1cc(Cc2ccccc2)ccc1O]

4-benzyl-2-((diethylamino)methyl)phenol

D3

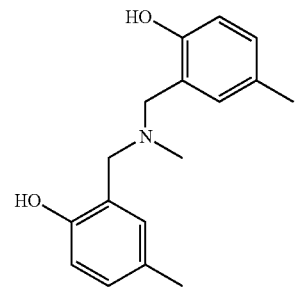

2,2'-(methylazanediyl)bis(methylene)bis(4-methylphenol)

D4

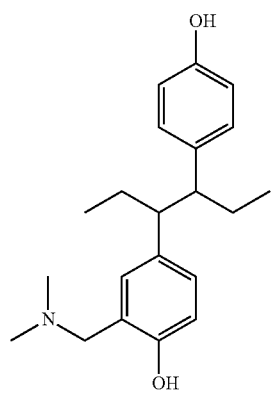 [SMILES: CCC(c1ccc(O)cc1)C(CC)c1ccc(O)c(CN(C)C)c1]

2-((dimethylamino)methyl)-4-(4-(4-hydroxyphenyl)hexan-3-yl)phenol

TABLE 2-continued

G6 derivative compounds

D5 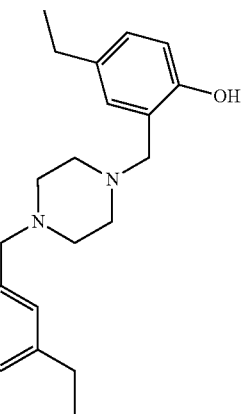

2,2'-(piperazine-1,4-diylbis(methylene))bis(4-ethylphenol)

D6 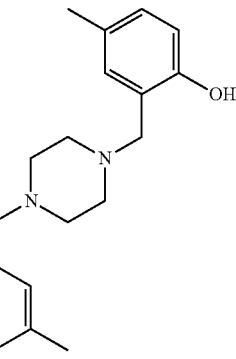

2,2'-(piperazine-1,4-diylbis(methylene))bis(4-methylphenol)

D7 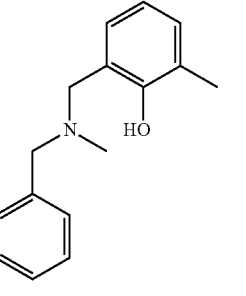

6,6'-(methylazanediyl)bis(methylene))bis(2-methylphenol)

D8 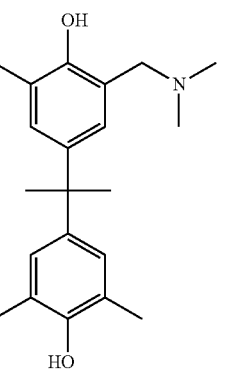

4,4'-(propane-2,2-diyl)bis(2-((dimethylamino)methyl)-6-methylphenol)

D9 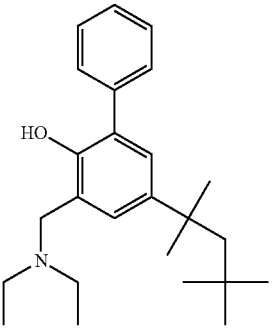 [SMILES: CCN(CC)Cc1cc(C(C)(C)CC(C)(C)C)cc(-c2ccccc2)c1O]

3-((diethylamino)methyl)-5-(2,4,4-trimethylpentan-2-yl)biphenyl-2-ol

D10 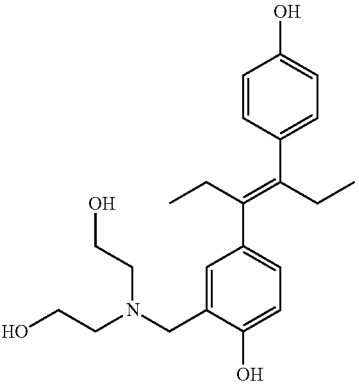 [SMILES: CC/C(=C(/CC)c1ccc(O)c(CN(CCO)CCO)c1)c1ccc(O)cc1]

(E)-2,2'-(2-hydroxy-5-(4-(4-hydroxyphenyl)hex-3-en-3-yl)benzylazanediyl)diethanol D11 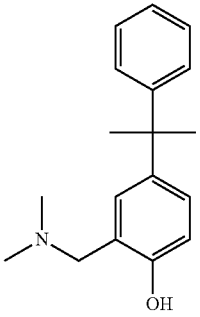 [SMILES: CN(C)Cc1cc(C(C)(C)c2ccccc2)ccc1O]

2-((dimethylamino)methyl)-4-(2-phenylpropan-2-yl)phenol

D12 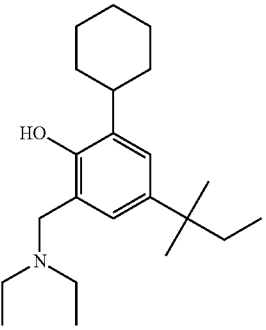 [SMILES: CCN(CC)Cc1cc(C(C)(C)CC)cc(C2CCCCC2)c1O]

2-cyclohexyl-6-((diethylamino)methyl)-4-tert-pentylphenol

TABLE 2-continued

G6 derivative compounds

D13
3-((diethylamino)methyl)-5-tert-pentylbiphenyl-2-ol

D14
5-tert-butyl-3-((diethylamino)methyl)biphenyl-2-ol

D21
3-((dimethylamino)methyl)biphenyl-2-ol

D22
(E)-2-((diethylamino)methyl)-4-(4-(4-methoxyphenyl)hex-3-en-3-yl)phenol

D23
2-((benzylamino)methyl)-4,6-dimethylphenol

D25
2-cyclohexyl-6-((diethylamino)methyl)-4-(2-phenylpropan-2-yl)phenol

D28
(E)-2-((dimethylamino)methyl)-4-(4-(4-methoxyphenyl)hex-3-en-3-yl)phenol

TABLE 2-continued

G6 derivative compounds

D30

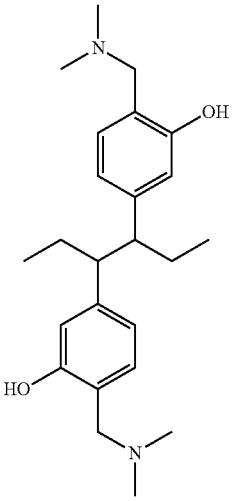 [SMILES: CCC(c1ccc(CN(C)C)c(O)c1)C(CC)c1ccc(CN(C)C)c(O)c1]

5,5'-(hexane-3,4-diyl)bis(2-((dimethylamino)methyl)phenol)

The invention also relates to the pharmaceutically acceptable salts and esters of the above-mentioned compounds.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

According to another embodiment, the invention provides compounds which associate with or bind to the kinase binding pocket of Jak2 defined by the following residues; GLN14 LEU15 GLY16 LYS17 (SEQ ID NO: 8) GLY21 SER22 VAL39 ALA40 VAL41 ARG57 ILE70 ARG86 ILE88 MET89 GLU90 TYR91 LEU92 PRO93 TYR94 GLY95 (SEQ ID NO: 9) LEU97 ARG98 ALA138 THR139 ARG140 ILE152 GLY153 ASP154 PHE155 (SEQ ID NO: 10), or a Jak2 protein-protein binding partner binding pocket (including targets where Jak2 mediates a biological process or mechanism) that are useful in the methods described herein. In one aspect, the interaction of the test compound and the Jak2 kinase domain comprises one H-bond acceptor interaction with Glu90 and one H-bond donor interaction with Leu92. It appears these interactions are important for a potent Jak2 inhibitor.

3. USES OF THE COMPOUNDS OF THE INVENTION

Somatic mutations in the Jak2 allele are described in virtually all patients diagnosed with polycythemia vera (PV), and about 50% of patients with essential thrombocythemia (ET) and chronic idiopathic myelofibrosis (CIMF).[1] The most common Jak2 mutation is the result of a G→T point mutation at nucleotide 1849 within exon 12, resulting in a phenylalanine substation for valine at codon 617 (V617F). The mutation is located in the JAK homology 2 (JH2) negative regulatory domain and its presence results in increased Jak2 kinase activity that is unresponsive to the negative feedback mechanisms that govern normal cell growth. A causal role for the mutation is supported in vivo by murine transfection studies resulting in erythrocytosis and myelofibrosis in recipient animals.[2] Additional somatic, Jak2 gain-of-function mutations have been detected in exon 12 in patients with V617F negative erythrocytosis.[3] Here, a single patient with multiple, novel Jak2 mutations in this region is described, and it is shown that the growth of this patient's cells can be inhibited, ex vivo, with a putative Jak2 small molecule inhibitor.

The patient was a 36 year old male with a history of motor vehicle accident who underwent splenectomy, left nephrectomy and partial pancreatectomy twelve years ago. Three years ago, an elevated platelet count was noted (1.3 million); hemoglobin was 14.8 gm/dl, hematocrit 45% and the white blood cell count was 12.2. Persistent elevations of the platelet count were documented on complete blood count in the intervening three years; recent complete blood counts revealed a platelet count of 2 million, white blood cell count of 15K which unremarkable differential count, hemoglobin of 13.8 gm/dL, hematocrit of 41%. Serum erythropoietin was reduced (less than 3.7). The patient was asymptomatic. Peripheral blood smears showed a striking thrombocytosis with platelets of variable size with frequent larger platelets. Bone marrow biopsy and aspirate were most remarkable for an increase in clustered, atypical megkaryocytes with hyperlobated nuclei (FIG. 1a). The myeloid to erythroid ratio was elevated at 7:1 with complete maturation. Blasts or immature cells were not increased. Reticulin fibrosis was mildly increased. Stainable iron was diminished. Cytogenetics showed a normal karyotype, 46, XY. The overall findings were consistent with a diagnosis of essential thrombocythemia.

A portion of the patient's aspirate containing ~$10^6$ mononuclear cells was subjected to standard mRNA isolation followed by cDNA synthesis. An area covering exon 12 was then amplified via PCR using Jak2 gene specific primers; the top strand primer was 5'-GTT CTT TTG AAA GTC CTA (SEQ ID NO:1) and bottom strand primer was 5'-CTG CTT AGC CAC TCC AAG (SEQ ID NO:2). The PCR products were then directly ligated into a shuttle vector, transformed into *E. Coli* and grown over night on antibiotic resistant plates. Plasmid DNA was prepared from independent colonies and subjected to DNA sequence analysis. While the V617F mutation was never observed in any of this patient's samples, three other mutations were present on all transcripts that were examined (n=4). The mutations were K603Q, D620E, and C644S (FIG. 1b).

Although this patient lacked the V617F mutation, it was hypothesized that the three other Jak2 mutations were the source of his disease. To test this, hematopoietic progenitor cells were cultured in a semi-solid colony assay medium (Stem Cell Technologies) in both the presence and absence of a putative Jak2 small molecule inhibitor, 3-[5-[(4-oxo-4-phenyl-butan-2-ylidene)amino]pentylimino]-1-phenyl-butan-1-one (25 μM final). Additionally, since hematopoietic progenitors taken from patients with myeloproliferative disorders are known to be hyper-sensitive to cytokine stimulation, the cells were also cultured in both the presence and absence of human thrombopoietin (50 ng/ml). Thirteen days after plating, megkaryocyte colonies were scored and tabulated (FIG. 1c). It was found that treatment of this patient's cells with thrombopoietin (TPO) resulted in a marked increase in megkaryocyte colony formation. However, this increased cell growth was largely blunted when the cells were cultured in the presence of the putative Jak2 small molecule inhibitor.

Here, biopsy and clinical findings of a patient were consistent with a myeloproliferative disorder in general and essential thrombocythemia in particular. Although this patient lacked the common V617F Jak2 mutation, he did possess other JH2 domain mutations; namely, K603Q, D620E, and C644S. The D620E mutation has been previously reported in a patient who, in addition, harbored the V617F mutation, and manifested a clinical phenotype of polycythemia vera.[4] In another report, a patient with leukocytosis was found to have the same D620E mutation and it was suggested that this mutation is comparable to the V617F mutation, resulting in loss of auto-inhibitory function within the JH2 domain.[5] Examination of the literature found no previous reports of the K603Q and C644S variants however, and thus, these two Jak2 mutations appear to be novel. The patient described herein is unusual in that multiple mutations were identified in a region of the Jak2 gene (JH2 domain) that would be consistent with producing a gain-of-function phenotype. The interaction of multiple mutations within one patient raises the possibility that there may be modification of the disease phenotype by multiple Jak2 mutations. As such, future studies targeted at the identification and characterization of new Jak2 variants as well as there frequency in given populations, may improve the clinical understanding of these diseases.

Previous efforts of these applicants have been directed at identifying novel Jak2 tyrosine kinase small molecule inhibitors.[6] Recent work from has shown that 3-[5-[(4-oxo-4-phenyl-butan-2-ylidene)amino]pentylimino]-1-phenyl-butan-1-one is also a potent and direct inhibitor of Jak2 tyrosine kinase function (data not shown). Here, it is shown that treatment of this patient's hematopoietic cells with this specific inhibitor greatly reduced pathologic cell growth, ex vivo. As such, this compound may have practical applications in Jak2 related research studies and perhaps, Jak2 clinical studies.

In summary, the clinical and experimental data have identified a patient with essential thrombocythemia who lacks the common Jak2 V617F mutation, but possesses multiple other Jak2 mutations; namely, K603Q, D620E, and C644S. Additionally, the pathologic growth of this patient's hematopoietic progenitor cells can be greatly reduced, ex vivo, via treatment with the putative Jak2 small molecule inhibitor, 3-[5-[(4-oxo-4-phenyl-butan-2-ylidene)amino]pentylimino]-1-phenyl-butan-1-one.

In one embodiment, the invention provides methods for treating a subject for a Jak2-mediated disorder (e.g., polycythemia vera, essential thrombocythemia, angiogenic myeloid metaplasia), by administering to the subject an effective amount of a compound capable of disrupting Jak2 or Jak2-mutant (e.g., K603Q, D620E, and C644S) binding.

In this embodiment, the compounds of the invention may either directly or indirectly modulate having Jak2 or Jak2 mutant activity can be contacted with a compound of the invention to inhibit disease or disorder processes or modulation of the Jak2 metabolic cascade. Contacting cells or administering the compounds of the invention to a subject is one method of treating a cell or a subject suffering from or susceptible to unwanted or undesired Jak2 or a Jak2 mutant mediated disorder.

In this embodiment, the compounds of the invention may either directly or indirectly modulate having Jak2 or Jak2 mutant activity by inhibiting Jak2 autophosphorylation. In another aspect, the compounds of the invention do not inhibit c-Src or Tyk2 autophosphorylation as effectively as Jak2 autophosphorylation. In aspects, the compounds demonstrate a level of Jak2 (or Jak2 mutant) autophosphorylation inhibition that is at least 2-, 5-, 10-, 25-, 50- or 100-fold higher than c-Src or Tyk2 autophosphorylation inhibition. Exemplary compounds include compounds described herein.

In certain embodiments, the methods of the invention include administering to a subject a therapeutically effective amount of a compound of the invention in combination with another pharmaceutically active compound. Examples of pharmaceutically active compounds include compounds known to treat proliferative disorders, e.g., anticancer agents, antitumor agents, antiangiogenesis agents, chemotherapeutics, antibodies, etc. Other pharmaceutically active compounds that may be used can be found in *Harrison's Principles of Internal Medicine*, Thirteenth Edition, Eds. T. R. Harrison et al. McGraw-Hill N.Y., N.Y.; and the Physicians Desk Reference 50th Edition 1997, Oradell N.J., Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

In certain embodiments, the compound of the invention can be used in combination therapy with conventional anticancer therapeutics. Conventional treatment regimens include, for example, radiation, drugs, or a combination of both. In addition to radiation, the following drugs, usually in combinations with each other, are often used to treat acute leukemias: vincristine, prednisone, methotrexate, mercaptopurine, cyclophosphamide, and cytarabine. Other examples include, for example, doxorubicin, cisplatin, taxol, 5-fluorouracil, etoposid, etc., which demonstrate advantages (e.g., chemosensitization of cells) in combination with the compounds described herein. In chronic leukemia, for example, busulfan, melphalan, and chlorambucil can be used in combination. Proteosome inhibitors (e.g., MG-132), hydroxyureas (e.g., Hydrea or hydroxycarbamide) or kinase inhibitors (e.g., GLEEVEC) can also be used in combination with the compounds herein. Most conventional anti-cancer drugs are highly toxic and tend to make patients quite ill while undergoing treatment. Vigorous therapy is based on the premise that unless every cancerous cell is destroyed, the residual cells will multiply and cause a relapse.

Determination of a therapeutically effective anti-proliferative amount or a prophylactically effective anti-proliferative amount of the compound of the invention of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective anti-proliferative amount of a compound of the invention of the invention is expected to vary from about 0.1 milligram per kilogram of body weight per day (mg/kg/day) to about 100 mg/kg/day.

Compounds determined to be effective for the prevention or treatment of disease or disorders in animals, e.g., dogs, chickens, and rodents, may also be useful in treatment of tumors in humans. Those skilled in the art of treating tumors in humans will know, based upon the data obtained in animal studies, the dosage and route of administration of the compound to humans. In general, the dosage and route of administration in humans is expected to be similar to that in animals.

The identification of those patients who are in need of prophylactic treatment for Jak2-mediated disorders is well within the ability and knowledge of one skilled in the art. Certain of the methods for identification of patients which are at risk of developing Jak2-mediated disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a Jak2-mediated disorder by methods well known in the art (e.g., determining tumor size or screening for cancer markers where the Jak2-mediated disorder is present) and then administering a therapeutically effective amount of an inhibitor of cell proliferation (e.g., those described herein) according to the invention to the subject. After an appropriate period of time after the administration of the compound (e.g., 1 day, 1 week, 2 weeks, one month, six months), the extent of the Jak2-mediated disorder is determined again. The modulation (e.g., decrease) of the extent or invasiveness of the Jak2-mediated disorder indicates efficacy of the treatment. The extent or invasiveness of the Jak2-mediated disorder may be determined periodically throughout treatment. For example, the extent or invasiveness of the Jak2-mediated disorder may be checked every few hours, days or weeks to assess the further efficacy of the treatment. A decrease in extent or invasiveness of the Jak2-mediated disorder indicates that the treatment is efficacious. The method described may be used to screen or select patients that may benefit from treatment with an inhibitor of a Jak2-mediated disorder.

As used herein, "obtaining a biological sample from a subject," includes obtaining a sample for use in the methods described herein. A biological sample is described above.

Yet another aspect presents a method to identify a compound that modulates the interaction of Jak2-mediated binding partner, or specific domains thereof. The method may include obtaining the crystal structure of a Jak2-mediated binding partner, or specific domains thereof (optionally apo form or complexed) or obtaining the information relating to the crystal structure of a Jak2-mediated binding partner, or specific domains thereof (optionally apo form or complexed), in the presence and/or absence of the test compound. Compounds may then be computer modeled into or on the Jak2-mediated binding partner, or specific domains thereof binding site of the crystal structure to predict stabilization of the interaction between the Jak2-mediated binding partner, or specific domains thereof and the test compound. Once potential modulating compounds are identified, the compounds may be screened using cellular assays, such as the ones identified herein and competition assays known in the art. Compounds identified in this manner are useful as therapeutic agents.

In another aspect, a compound of the invention is packaged in a therapeutically effective amount with a pharmaceutically acceptable carrier or diluent. The composition may be formulated for treating a subject suffering from or susceptible to a Jak2-mediated disorder, and packaged with instructions to treat a subject suffering from or susceptible to a Jak2-mediated disorder.

In another aspect, the invention provides methods for inhibiting cell proliferation. In one embodiment, a method of inhibiting cell proliferation (or a Jak2-mediated disorder) according to the invention includes contacting cells with a compound capable of modulating Jak2 or a Jak2-mediated binding partner, or specific domains thereof. In either embodiment, the contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

In another aspect, methods of inhibiting a Jak2-mediated disorder in a subject include administering an effective amount of a compound of the invention (i.e., a compound described herein) to the subject. The administration may be by any route of administering known in the pharmaceutical arts. The subject may have a Jak2-mediated disorder, may be at risk of developing a Jak2-mediated disorder, or may need prophylactic treatment prior to anticipated or unanticipated exposure to a conditions capable of increasing susceptibility to a Jak2-mediated disorder, e.g., exposure to carcinogens or to ionizing radiation.

The subject may be at risk of a Jak2-mediated disorder, may be exhibiting symptoms of a Jak2-mediated disorder, may be susceptible to a Jak2-mediated disorder and/or may have been diagnosed with a Jak2-mediated disorder.

If the modulation of the status indicates that the subject may have a favorable clinical response to the treatment, the subject may be treated with the compound. For example, the subject can be administered therapeutically effective dose or doses of the compound.

Kits of the invention include kits for treating a Jak2-mediated disorder in a subject. The kit may include a compound of the invention, for example, a compound described herein, pharmaceutically acceptable esters, salts, and prodrugs thereof, and instructions for use. The instructions for use may include information on dosage, method of delivery, storage of the kit, etc. The kits may also include, reagents, for example, test compounds, buffers, media (e.g., cell growth media), cells, etc. Test compounds may include known compounds or newly discovered compounds, for example, combinatorial libraries of compounds. One or more of the kit of the invention may be packaged together, for example, a kit for assessing the efficacy of an treatment for a Jak2-mediated disorder may be packaged with a kit for monitoring the progress of a subject being treated for a Jak2-mediated disorder according to the invention.

The present methods can be performed on cells in culture, e.g. in vitro or ex vivo, or on cells present in an animal subject, e.g., in vivo. Compounds of the inventions can be initially tested in vitro using primary cultures of proliferating cells, e.g., transformed cells, tumor cell lines, and the like.

The present method can be performed on cells in culture, e.g. in vitro or ex vivo, or on cells present in an animal subject, e.g., in vivo. Compound of the invention can be initially tested in vitro using cells or other mammalian or non-mammalian animal models. Alternatively, the effects of compound of the invention can be characterized in vivo using animals models.

4. PHARMACEUTICAL COMPOSITIONS

The invention also provides a pharmaceutical composition, comprising an effective amount of a compound of the and a pharmaceutically acceptable carrier. In a further embodiment, the effective amount is effective to treat a Jak2-mediated disorder, as described previously.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredients) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious side effects. Preferably, the compound of the invention of the present invention is administered at a concentration of about 0.001 mg to about 100 mg per kilogram of body weight, about 0.001-about 10 mg/kg or about 0.001 mg-about 100 mg/kg of body weight. Ranges intermediate to the above-recited values are also intended to be part of the invention.

6. SCREENING METHODS AND SYSTEMS

In another aspect, the invention provides a machine readable storage medium which comprises the structural coordinates of either one or both of the binding pockets identified herein, or similarly shaped, homologous binding pockets. Such storage medium encoded with these data are capable of displaying a three-dimensional graphical representation of a molecule or molecular complex which comprises such binding pockets on a computer screen or similar viewing device.

The invention also provides methods for designing, evaluating and identifying compounds which bind to the aforementioned binding pockets. Thus, the computer produces a three-dimensional graphical structure of a molecule or a molecular complex which comprises a binding pocket.

In another embodiment, the invention provides a computer for producing a three-dimensional representation of a molecule or molecular complex defined by structure coordinates of Jak2 or domains thereof, or a three-dimensional representation of a homologue of said molecule or molecular complex, wherein said homologue comprises a binding pocket that has a root mean square deviation from the backbone atoms of said amino acids of not more than 2.0 (more preferably not more than 1.5) angstroms.

In exemplary embodiments, the computer or computer system can include components which are conventional in the art, e.g., as disclosed in U.S. Pat. No. 5,978,740 and/or U.S. Pat. No. 6,183,121 (incorporated herein by reference). For example, a computer system can includes a computer comprising a central processing unit ("CPU"), a working memory (which may be, e.g., RAM (random-access memory) or "core" memory), a mass storage memory (such as one or more disk drives or CD-ROM drives), one or more cathode-ray tube (CRT) or liquid crystal display (LCD) display terminals, one or more keyboards, one or more input lines, and one or more output lines, all of which are interconnected by a conventional system bus.

Machine-readable data of this invention may be inputted to the computer via the use of a modem or modems connected by a data line. Alternatively or additionally, the input hardware may include CD-ROM drives, disk drives or flash memory. In conjunction with a display terminal, a keyboard may also be used as an input device.

Output hardware coupled to the computer by output lines may similarly be implemented by conventional devices. By way of example, output hardware may include a CRT or LCD display terminal for displaying a graphical representation of a binding pocket of this invention using a program such as QUANTA or PYMOL. Output hardware might also include a printer, or a disk drive to store system output for later use.

In operation, the CPU coordinates the use of the various input and output devices, coordinates data accesses from the mass storage and accesses to and from working memory, and determines the sequence of data processing steps. A number of programs may be used to process the machine-readable data of this invention, including commercially-available software.

A magnetic storage medium for storing machine-readable data according to the invention can be conventional. A magnetic data storage medium can be encoded with a machine-readable data that can be carried out by a system such as the computer system described above. The medium can be a conventional floppy diskette or hard disk, having a suitable substrate which may be conventional, and a suitable coating, which may also be conventional, on one or both sides, containing magnetic domains whose polarity or orientation can be altered magnetically. The medium may also have an opening (not shown) for receiving the spindle of a disk drive or other data storage device.

The magnetic domains of the medium are polarized or oriented so as to encode in manner which may be conventional, machine readable data such as that described herein, for execution by a system such as the computer system described herein.

An optically-readable data storage medium also can be encoded with machine-readable data, or a set of instructions, which can be carried out by a computer system. The medium can be a conventional compact disk read only memory (CD-ROM) or a rewritable medium such as a magneto-optical disk which is optically readable and magneto-optically writable.

In the case of CD-ROM, as is well known, a disk coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, a data-recording coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Structure data, when used in conjunction with a computer programmed with software to translate those coordinates into the 3-dimensional structure of a molecule or molecular complex comprising a binding pocket may be used for a variety of purposes, such as drug discovery.

For example, the structure encoded by the data may be computationally evaluated for its ability to associate with chemical entities. Chemical entities that associate with a binding pocket of a Jak2, or specific domains thereof, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention relates to a method for evaluating the potential of a chemical entity to associate with a) a molecule or molecular complex comprising a binding pocket of Jak2, or specific domains thereof, or b) a homologue of said molecule or molecular complex, wherein said homologue comprises a binding pocket that has a root mean square deviation from the backbone atoms of said amino acids of not more than 2.0 (more preferably 1.5) angstroms.

This method comprises the steps of:
i) employing computational means to perform a fitting operation between the chemical entity and a binding pocket of the molecule or molecular complex; and
ii) analyzing the results of the fitting operation to quantify the association between the chemical entity and the binding pocket. The term "chemical entity", as used herein, refers to chemical compounds, complexes of at least two chemical compounds, and fragments of such compounds or complexes.

The design of compounds that bind to or inhibit Jak2, or specific domains thereof binding pockets according to this invention generally involves consideration of several factors. First, the entity must be capable of physically and structurally associating with parts or all of the Jak2 binding site, or specific domains thereof-related binding pockets. Non-covalent molecular interactions important in this association include hydrogen bonding, van der Waals interactions, hydrophobic interactions and electrostatic interactions. Second, the entity must be able to assume a conformation that allows it to associate with the Jak2, or specific domains thereof-related binding pocket(s) directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the binding pocket or homologues thereof.

The potential inhibitory or binding effect of a chemical entity on a Jak2, or specific domains thereof-related binding pocket may be analyzed prior to its actual synthesis and testing by the use of computer modeling techniques. If the theoretical structure of the given entity suggests insufficient interaction and association between it and the target binding pocket, testing of the entity is obviated. However, if computer modeling indicates a strong interaction, the molecule may then be synthesized and tested for its ability to bind to a binding pocket. This may be achieved, e.g., by testing the ability of the molecule to inhibit Jak2, or specific domains thereof activity, e.g., using assays described herein or known in the art. In this manner, synthesis of inoperative compounds may be avoided.

A potential inhibitor of a Jak2, or specific domains thereof-related binding pocket may be computationally evaluated by means of a series of steps in which chemical entities or fragments are screened and selected for their ability to associate with the Jak2, or specific domains thereof-related binding pockets.

One skilled in the art may use one of several methods to screen chemical entities or fragments for their ability to associate with Jak2, or specific domains thereof-related binding pocket. This process may begin by visual inspection of, for example, a Jak2, or specific domains thereof-related binding pocket on the computer screen based on the Jak2 binding site, or specific domains thereof structure coordinates described herein, or other coordinates which define a similar shape generated from the machine-readable storage medium. Selected fragments or chemical entities may then be positioned in a variety of orientations, or docked, within that binding pocket as defined supra. Docking may be accomplished using software such as Quanta and DOCK, followed by energy minimization and molecular dynamics with standard molecular mechanics force fields, such as CHARMM and AMBER.

Specialized computer programs (e.g., as known in the art and/or commercially available and/or as described herein) may also assist in the process of selecting fragments or chemical entities.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of the target binding pocket.

Instead of proceeding to build an inhibitor of a binding pocket in a step-wise fashion one fragment or chemical entity at a time as described above, inhibitory or other binding compounds may be designed as a whole or "de novo" using either an empty binding site or optionally including some portion(s) of a known inhibitor(s). There are many de novo ligand design methods known in the art, some of which are commercially available (e.g., LeapFrog, available from Tripos Associates, St. Louis, Mo.).

Other molecular modeling techniques may also be employed in accordance with this invention [see, e.g., N. C. Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)].

Once a compound has been designed or selected, the efficiency with which that entity may bind to a binding pocket may be tested and optimized by computational evaluation.

Specific computer software is available in the art to evaluate compound deformation energy and electrostatic interactions. Examples of programs designed for such uses include: AMBER; QUANTA/CHARMM (Accelrys, Inc., Madison, Wis.) and the like. These programs may be implemented, for instance, using a commercially-available graphics workstation. Other hardware systems and software packages will be known to those skilled in the art.

Another technique involves the in silico screening of virtual libraries of compounds, e.g., as described herein. Many thousands of compounds can be rapidly screened and the best virtual compounds can be selected for further screening (e.g., by synthesis and in vitro testing). Small molecule databases can be screened for Jak2 domain, or specific domains thereof binding pocket. In this screening, the quality of fit of such entities to the binding site may be judged either by shape complementarity or by estimated interaction energy.

7. KITS

The invention also features kits. Included in the kits are compounds that re capable of modulating Jak2 activity. Any compound, or one or more compounds, can be selected from Table 1 or Table 2 for inclusion in the kits of the invention.

The kits also include instructions for use in treating cancer, for use in treating a hematological disorder, for use in treating a cardiac disorder, and for use in reducing Jak2-dependent cell growth.

Carrier means are suited for containing one or more container means such as vials, tubes, and the like, each of the container means comprising one of the separate elements to be used in the method. In view of the description provided herein of invention methods, those of skill in the art can readily determine the apportionment of the necessary reagents among the container means.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

EXAMPLES

Example 1

Database of Small Molecules

The NCI/DTP maintains a repository of approximately 240,000 samples (i.e., the plated compound set) which are non-proprietary and offered to the research community for discovery and development of new agents for the treatment of cancer, AIDS, or opportunistic infections afflicting subjects with cancer or AIDS. The three-dimensional coordinates for the NCI/DTP plated compound set is obtained in the MDL SD format (www.chm.tu-dresden.de/edv/vamp65/REFERS/vr_03d.htm) and converted to the mol2 format by the DOCK utility program SDF2MOL2. Partial atomic charges, solvation energies and van der Waals parameters for the ligands are calculated using SYBDB and added to the plated compound set mol2 files.

Example 2

Database Screening to Identify Potential Small Molecule Inhibitors of Jak2

In lieu of conducting high-throughput screening, a more rapid and economical structure-based approach combining molecular docking in silico with functional testing was used. A large chemical library of compounds with known three-dimensional structure is positioned in the structural pocket selected by "FlexX/Pharm."

For the model building the sequence of JAK-3 was used as a template. This is from the PDB database, the PDB code: 1YVJ. The sequence alignment as follows:

C; A sample alignment in the PIR format; used in tutorial

```
>P1;1YVJ
                                        (SEQ ID NO: 3)
structureX:1YVJ:
814:A:1103:A:undefined:undefined:-1.00:-1.00

PTIFEERHLKYISQLGKGNFGSVELCRYDPLGDNTGALVAVKQLQHS

GPDQQRDFQREIQILKALHSDFIVKYRGVSYGPGRPELRLVMEYLPS

GCLRDFLQRHRARLDASRLLLYSSQICKGMEYLGSRRCVHRDLAARN
```

```
-continued
ILVESEAHVKIADFGLAKLLPLDKD--VVREPGQSPIFWYAPESLSD

NIFSRQSDVWSFGVVLYELFTYCDKSCSPSAEFLRMMGCERDV-PAL

CRLLELLEEGQRLPAPPACPAEVHELMKLCWAPSPQDRPSFSALGPQ

LDMLWSGSR*

>P1;jak2-1
                                          (SEQ ID NO: 4)
sequence:
jak2_1:1::290::ferredoxin:Peptococcus aerogenes:
2.00:_1.00
PTQFEERHLKFLQQLGKGNFGSVEMCRYDPLQDNTGEVVAVKKLQHS

TEEHLRDFEREIEILKSLQHDNIVKYKGVCYSAGRRNLRLIMEYLPY

GSLRDYLQKHKERIDHKKLLQYTSQICKGMEYLGTKRYIHRDLATRN

ILVENENRVKIGDFGLTKVLPQDKEYYKVKEPGESPIFWYAPQSLTE

SKFSVASDVWSFGVVLYELFTYIEKSKSPPVEFMRMIGNDKQGQMIV

FHLIELLKSNGRLPRPEGCPDEIYVIMTECWNNNVSQRPSFRDLSFG

WIKCGTV*
```

The "top 245" compounds with the highest scores are requested for functional testing from the NCI/DTP.

The National Cancer Institute/Developmental Therapeutics Program (NCI/DTP) maintains a repository of approximately 220,000 samples (the plated compound set) that are nonproprietary and offered to the extramural research community free of charge. The three-dimensional coordinates for the NCI/DTP plated compound set was obtained in the MDL SD format and converted to the mol2 format by the DOCK utility program SDF2MOL2. Partial atomic charges, solvation energies, and van der Waals parameters for the ligands were calculated using SYBDB and added to the plated compound set mol2 file.

In Silico Molecular Docking of Potential Jak2 Small Molecule Inhibitors

All docking calculations are performed with the FlexX/Pharm. First, a homology model for the 3D structure of Jak2 was developed, based on the domain structure of Jak3. Virtual screening was performed using FlexX Pharm software for structure based virtual screening. An important finding was to develop a particular combination of scoring functions (FlexX/Chem) that effectively identifies potent Jak2 inhibitors. After screening the whole NCI database the 3D structure of 2500 best scored complexes was carefully analyzed. The binding mode of the ligands and the interactions formed between within the binding pocket was examined, and identified ~250 compounds were identified as the most potent putative Jak2 inhibitors.

Example 3

Jak2-WT Autophosphorylation Assay

BSC-40 cells were transfected in serum free media with 5.0 µg of a plasmid encoding the wild type murine Jak2 cDNA (pRC-CMV-Jak2-WT) under the control of the bacteriophage T7 promoter, using Lipofectin and following the manufacturer's instructions (Invitrogen). Four hours later, the cells were infected with the recombinant vaccinia virus, vTF7-3, at a multiplicity of infection (MOI) of 1.0. One hour after that, the media containing Lipofectin/DNA/vTF7-3 was removed from the cells and replaced with fresh, serum-containing media. Inhibitor was added to the cells at this time at doses ranging from 10-100 µM. The cells were grown overnight at 37° C. to allow for high-level expression and subsequent tyrosine autophosphorylation of Jak2. Sixteen hour after the addition of the inhibitor, cells were washed with two volumes of ice-cold PBS containing 1 mM Na3VO4 and lysed in 0.8 ml ice-cold RIPA buffer containing protease inhibitors. The samples were sonicated and incubated on ice for 1 hour. Samples were spun at 16,000×g for 5 min at 4° C. and supernatants containing soluble protein lysates were normalized. Normalized lysates (approx. 400 ug/ml) were immunoprecipitated for 2-4 h at 4° C. with 2 µg of antibody and 20 ul of Protein A/G Plus agarose beads (Santa Cruz Biotechnology). After centrifugation, protein complexes were washed 3 times with wash buffer (25 mM Tris, pH 7.5, 150 mM NaCl, and 0.1% Triton X-100) and resuspended in SDS-containing sample buffer. Bound proteins were boiled, separated by SDS-PAGE, and transferred onto nitrocellulose membranes. The immunoprecipitating anti-Jak2-pAb (HR758) was from Santa Cruz Biotechnology. The immunoprecipitating anti-Tyr(P)-mAb (clone PY20) was from BD Transduction Laboratories. Phosphorylation levels were detected using enhanced chemiluminescence. Anti-Tyr(P) Western blotting was performed using a cocktail of antibodies consisting of clones 4G10 (Upstate Biotechnology), PY99 (Santa Cruz Biotechnology) and PY20 (BD Transduction Laboratories) at final dilutions of 1:1000 each. The anti-Jak2 antibody (758-776) was from Upstate Biotechnology (Millipore).

Example 4

Jak2-V617F Autophosphorylation Assay

BSC-40 cells were transfected in serum free media with 5.0 µg of a plasmid encoding the wild type murine Jak2 cDNA (pRC-CMV-Jak2-V617F) under the control of the bacteriophage T7 promoter, using Lipofectin and following the manufacturer's instructions (Invitrogen). Four hours later, the cells were infected with the recombinant vaccinia virus, vTF7-3, at a multiplicity of infection (MOI) of 1.0. One hour after that, the media containing Lipofectin/DNA/vTF7-3 was removed from the cells and replaced with fresh, serum-containing media. Inhibitor was added to the cells at this time at doses ranging from 10-100 µM. The cells were grown overnight at 37° C. to allow for high-level expression and subsequent tyrosine autophosphorylation of Jak2. Sixteen hour after the addition of the inhibitor, cells were washed with two volumes of ice-cold PBS containing 1 mM Na3VO4 and lysed in 0.8 ml ice-cold RIPA buffer containing protease inhibitors. The samples were sonicated and incubated on ice for 1 hour. Samples were spun at 16,000×g for 5 min at 4° C. and supernatants containing soluble protein lysates were normalized. Normalized lysates (approx. 400 ug/ml) were immunoprecipitated for 2-4 h at 4° C. with 2 µg of antibody and 20 ul of Protein A/G Plus agarose beads (Santa Cruz Biotechnology). After centrifugation, protein complexes were washed 3 times with wash buffer (25 mM Tris, pH 7.5, 150 mM NaCl, and 0.1% Triton X-100) and resuspended in SDS-containing sample buffer. Bound proteins were boiled, separated by SDS-PAGE, and transferred onto nitrocellulose membranes. The immunoprecipitating anti-Jak2-pAb (HR758) was from Santa Cruz Biotechnology. The immunoprecipitating anti-Tyr(P)-mAb (clone PY20) was from BD Transduction Laboratories. Phosphorylation levels were detected using enhanced chemiluminescence. Anti-Tyr(P) Western blotting was performed using a cocktail of antibodies consisting of clones 4G10 (Upstate Biotechnology), PY99 (Santa Cruz Biotechnology) and PY20 (BD Transduction Laboratories) at final dilutions of 1:1000 each. The anti-Jak2 antibody (758-776) was from Upstate Biotechnology (Millipore).

Example 5 c-Src Assay

Approximately 4 μL (12 units) of catalytically active recombinant p60c-src (Upstate Biotechnology) was incubated in 46 uL of in vitro kinase reaction buffer (50 mM HEPES, pH 7.6, 5 mM MnCl2, 5 mM MgCl2, 100 mM NaCl, 0.5 mM DTT), either in the presence of DMSO or 25 uM Z3. The reactions were incubated for 20 minutes at room temperature and then terminated by addition of SDS-containing buffer. The samples were Western blotted with an anti-Src (pY418) polyclonal antibody (Biosource). The samples were subsequently immunoblotted with a cocktail of c-Src antibodies (Biosource, Upstate Biotechnology) at final dilutions of 1:1000 each to demonstrate equal c-Src protein among all samples.

Example 6

Tyk2 Autophosphorylation Assay

COS-7 cells were transfected with 10 μg of a plasmid encoding the wild-type human Tyk2 cDNA in a eukaryotic expression vector (pMT2T-Tyk2-WT) for 5 hours using Lipofectin (Invitrogen). Following transfection, the cells were grown at 37° C. for 48 hours in serum containing media to allow for high-level Tyk2 tyrosine autophosphorylation. The cells were then treated with DMSO or 100 uM Z3 for 16 hours. Protein lystates were immunoprecipitated for 2 hours at 4° C. with 2 μg of anti-Tyk2 antibody (Santa Cruz Biotechnology) and 20 μL of Protein A/G Plus agarose beads (Santa Cruz Biotechnology). Proteins were separated by SDS-PAGE and transferred onto nitrocellulose membranes. Anti-Tyr(P) Western blotting was performed using a cocktail of antibodies consisting of clones 4G10 (Upstate Biotechnology), PY99 (Santa Cruz Biotechnology), and PY20 (BD Transduction Laboratories) at final dilutions of 1:1000 each.

Example 7

Demonstrating the Therapeutic Efficacy of G6 in Jak2-V61F-Induced Hematopoietic Disease in a NOD-SCID Mouse Model The Jak2-V617F mutation is a somatic activating mutation in the Jak2 tyrosine kinase. The mutation results from a valine to phenylalanine substitution within the regulatory pseudokinase domain of Jak2. This mutation results in the constitutive activation of Jak-STAT signaling. The Jak2-V617F mutation is thought to play a primary role in the pathogenesis of myeloproliferative disorders (MPD), including, but not limited to, polycythemia vera (PV), essential thrombocythemia (ET) and primary myelofibrosis (PMF).

As described herein, G6 is a small molecule that was developed using in silico structure based drug design. As discussed above, ~250 compounds were identified as the most potent putative Jak2 inhibitors, and from these compounds, Table 1 identifies those that may be considered among the most relevant putative Jak2 inhibitors including, but not limited to: 2-methyl-1-phenyl-4-pyridin-2-yl-2-(2-pyridin-2-ylethyl) butan-1-one; 3-[5-[(4-oxo-4-phenyl-butan-2-ylidene)amino] pentylimino]-1-phenyl-butan-1-one (G13); 2-(diethylaminomethyl)-4-[4-[3-(diethylaminomethyl)-4-hydroxyphenyl]hex-3-en-3-yl]phenol (G6); 2-dibutoxyphosphoryloxypentanenitrile (G31); ytterbium(+3) cation trihydroxide (G33); and 4-[(1S)-6,7-diethoxy-1,2,3,4-tetrahydroisoquinolin-1-yl]benzonitrile (G40). From this list, G6 was identified as a compound of particular interest.

Figure 8:
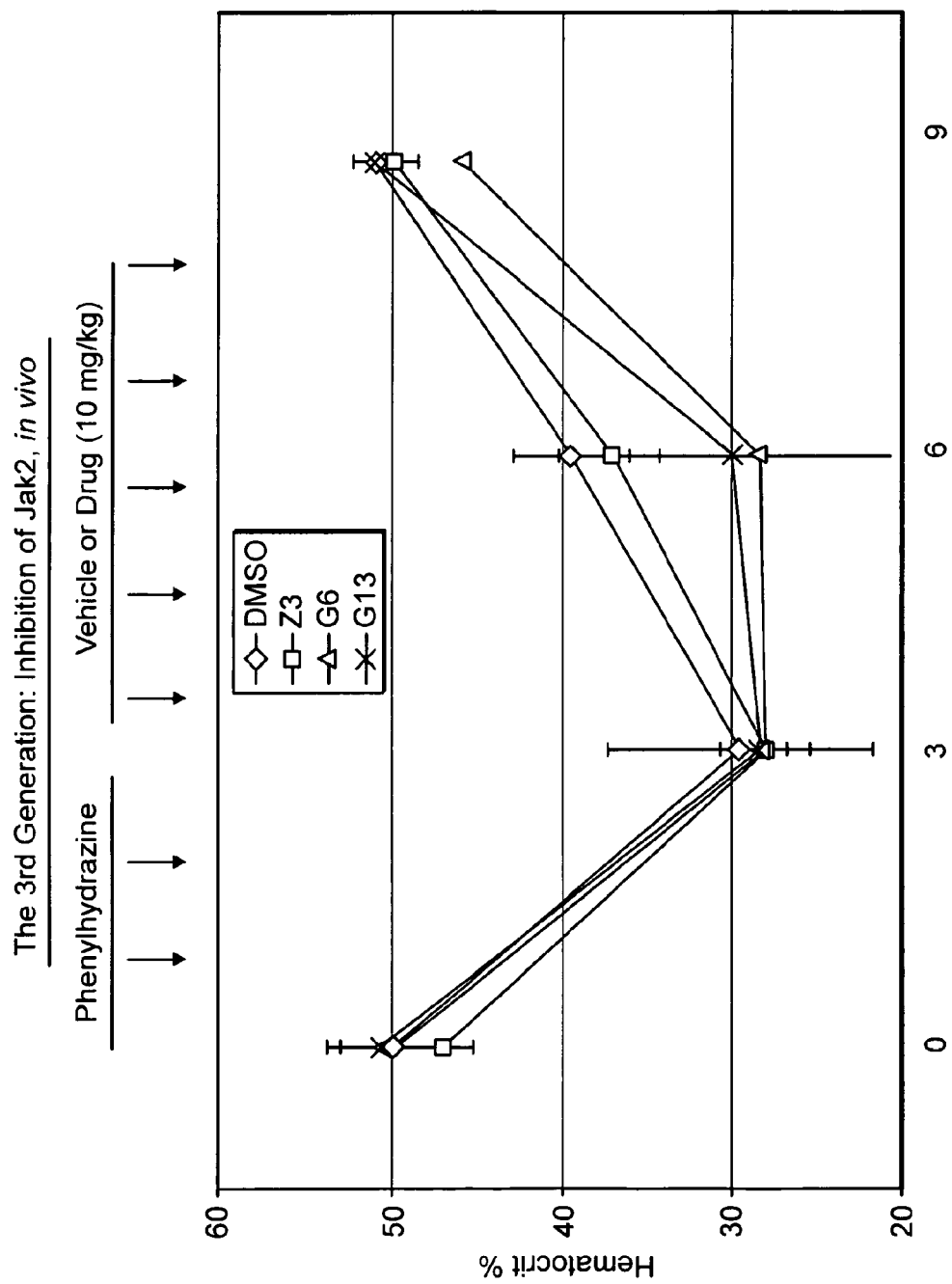
FIG. 8 depicts results showing inhibition of Jak2. in vivo.
Figure 9:
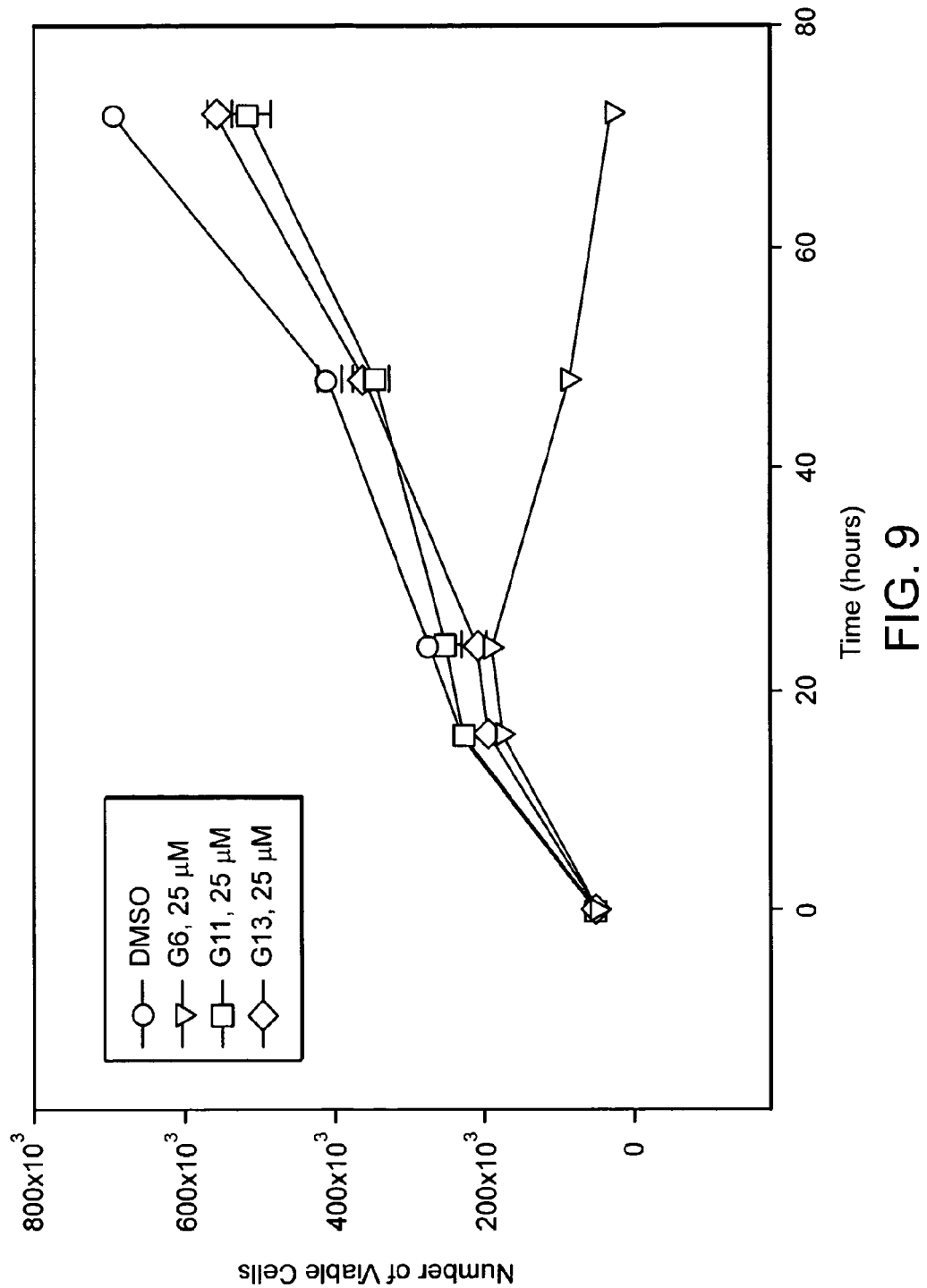
FIG. 9 is a graph showing G6 inhibition of Jak2-V617F dependent HEL cell growth.
Figure 10:
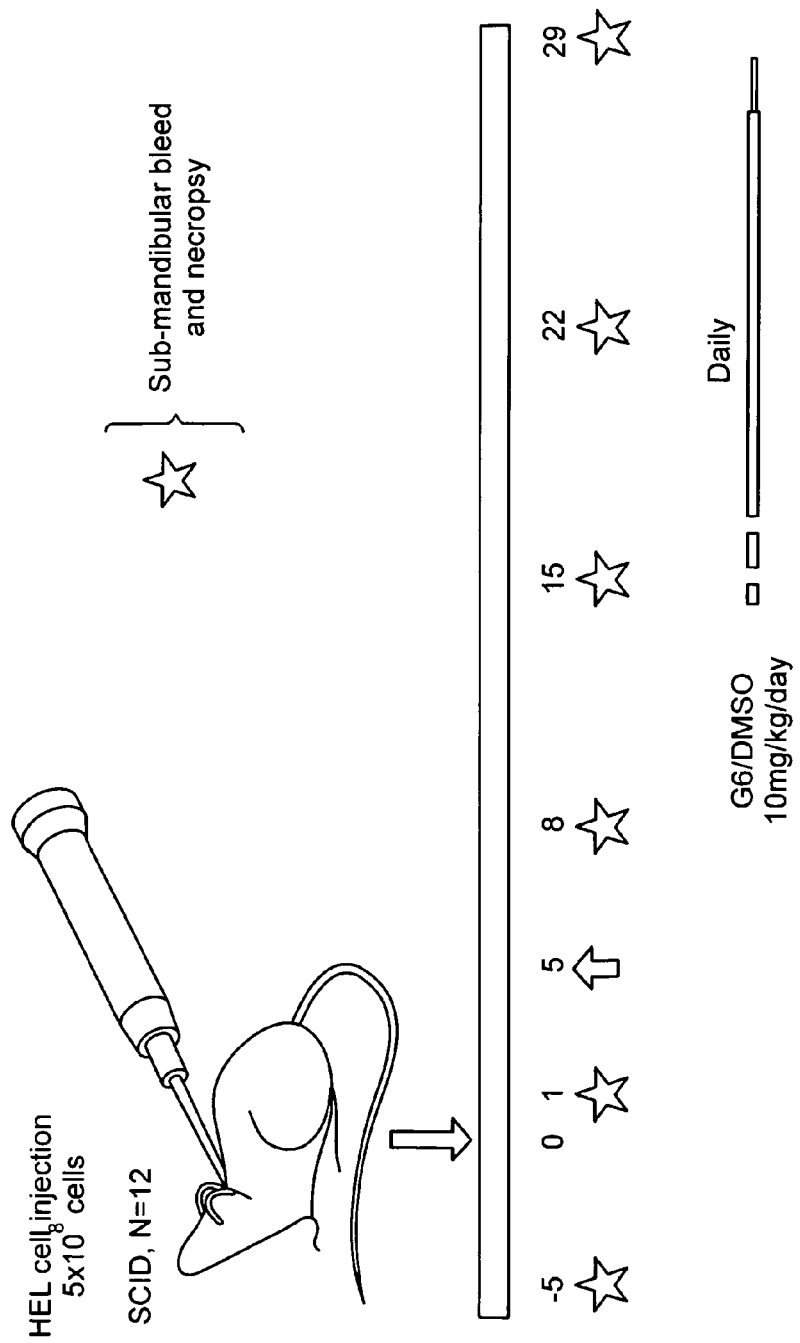
FIG. 10 is a schematic showing the experimental design. In the schematic, the starts represent the time points of submandibular bleed and necropsy.
Figure 11:
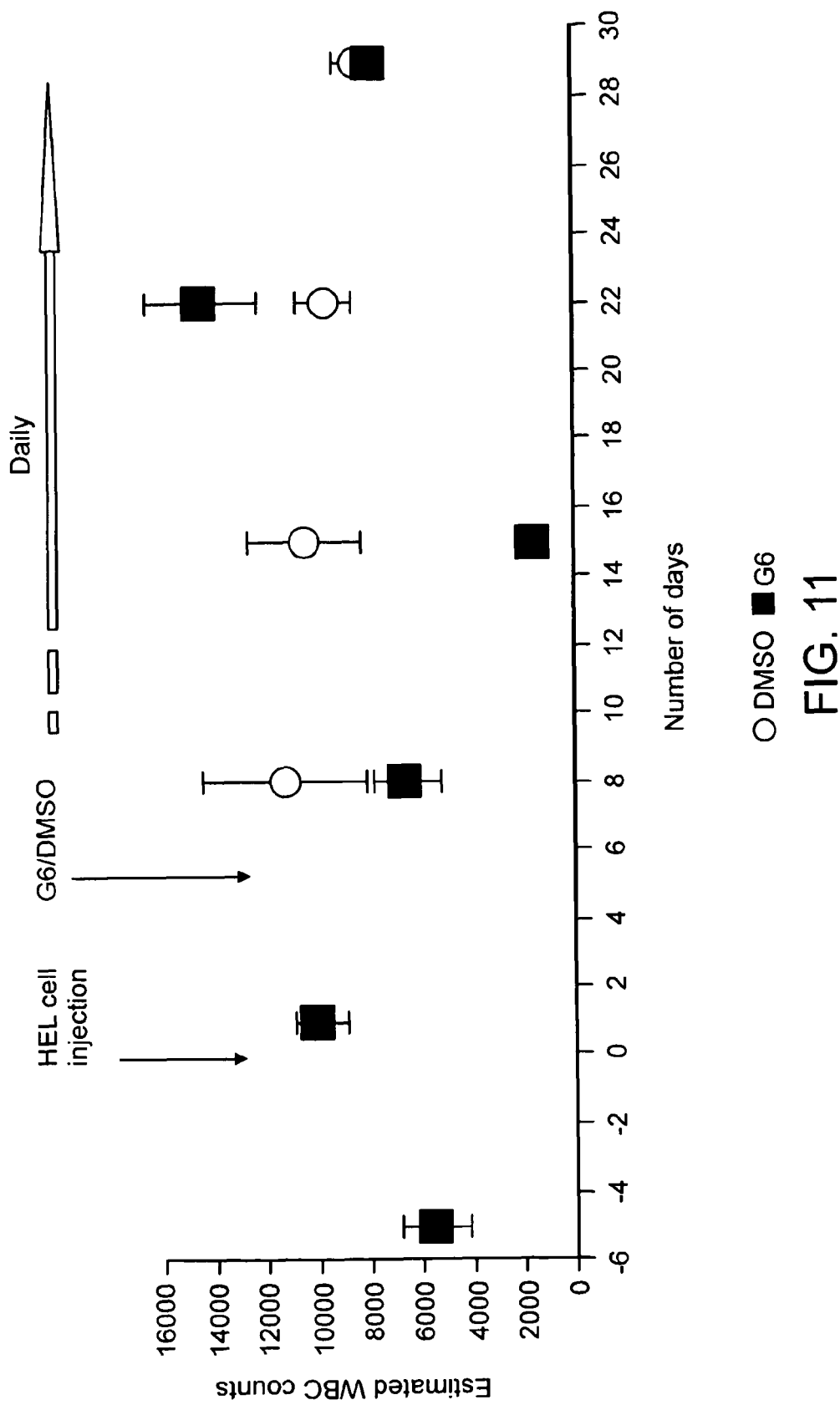
FIG. 11 is a graph showing G6 alleviated HEL cell-induced leukocytosis to normal levels by three days following treatment.
Figure 12:
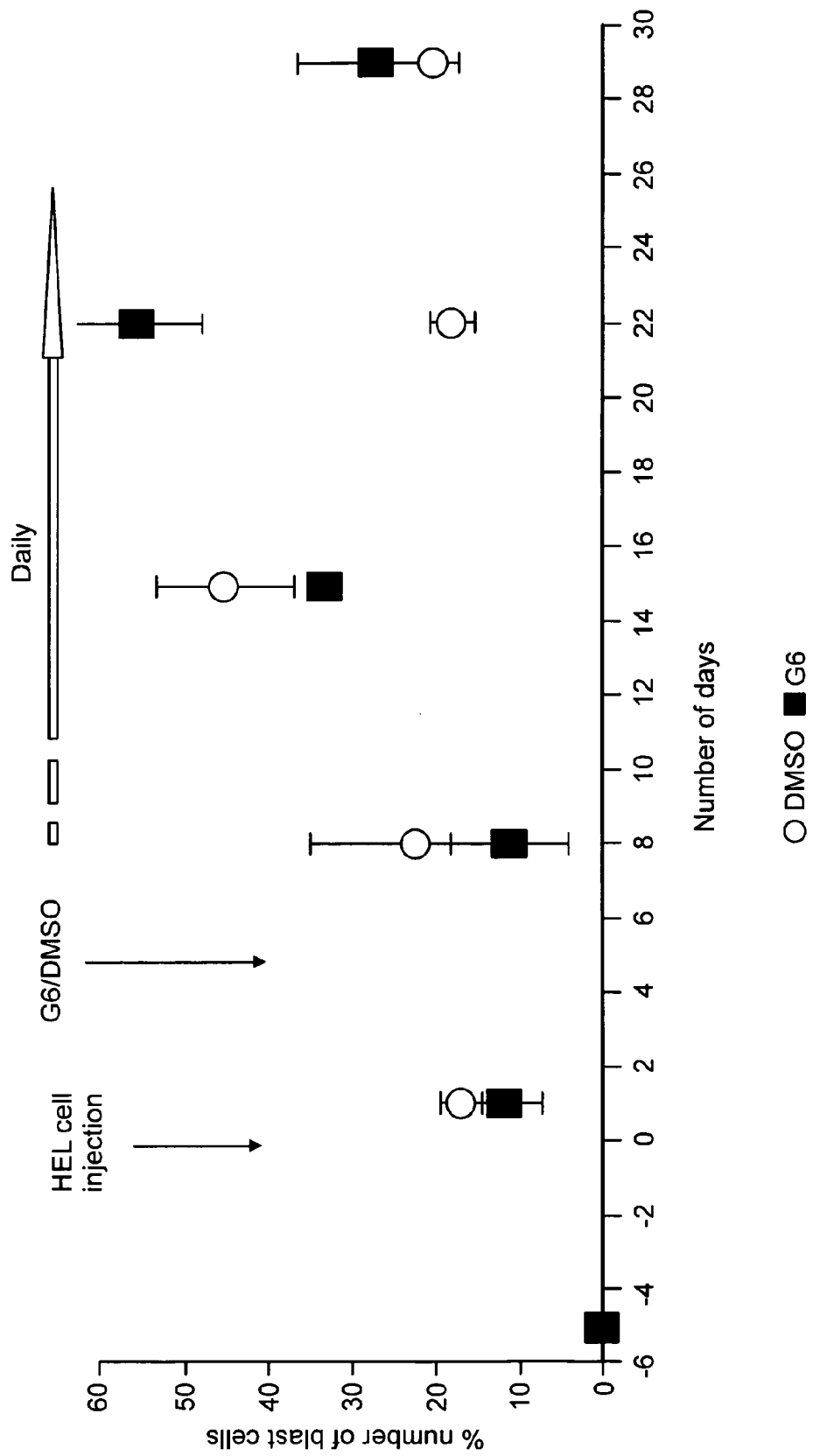
FIG. 12 is a graph showing HEL cell injection increased the percent of circulating blast cells.
Figure 13A:
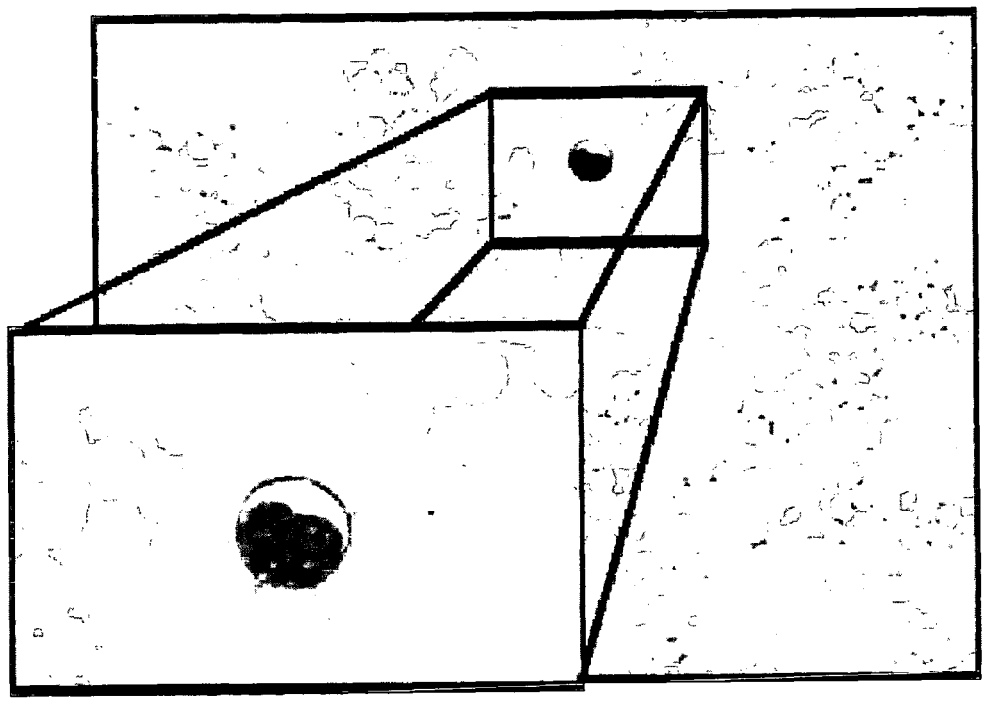
FIG. 13(A-C) is a series of hematoxylin and eosin stained images. Panel A shows a normal monocyte. Panels B and C show that HEL cell injection induce the appearance of blast cells.
Figure 13B:
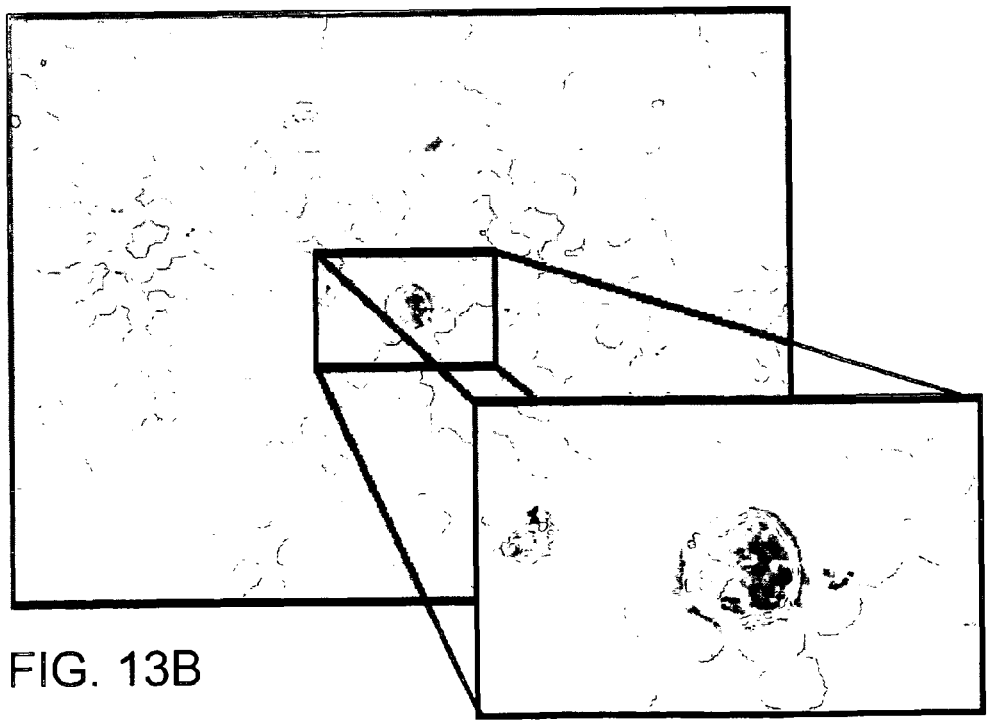
Figure 13C:
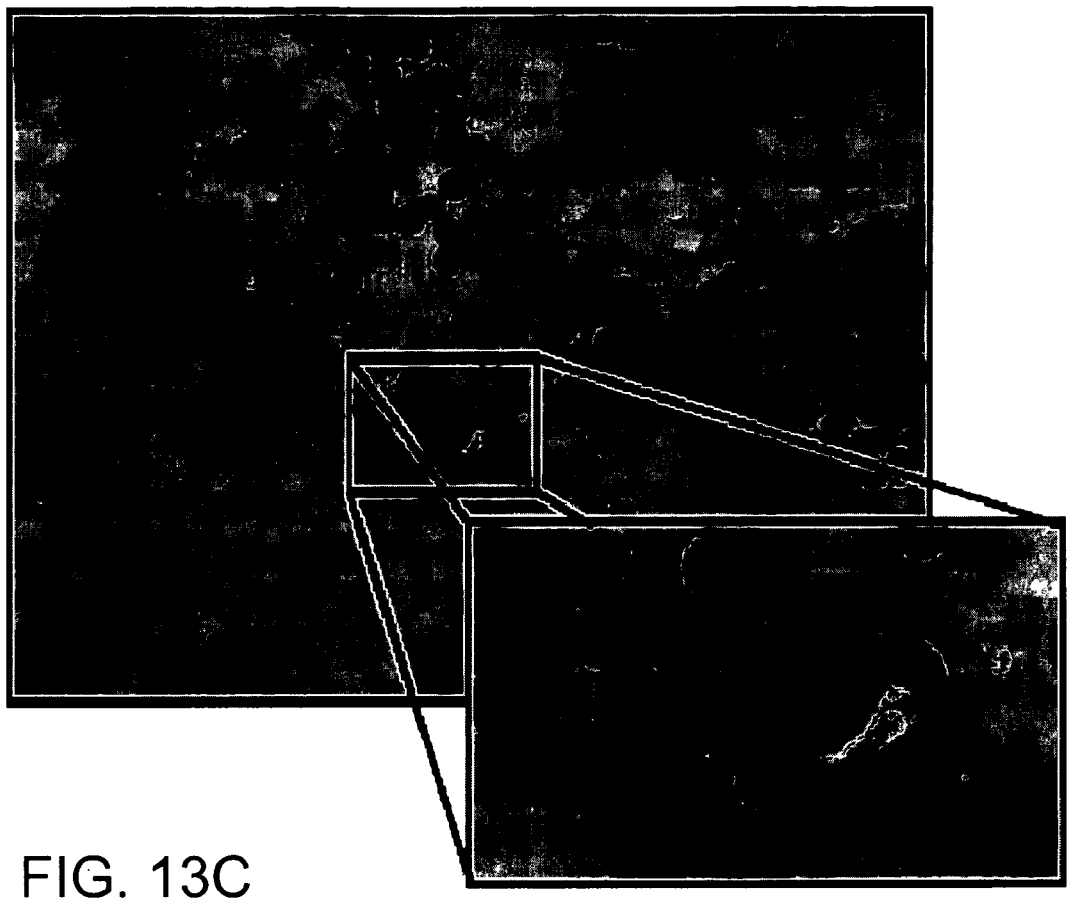
Figure 14:
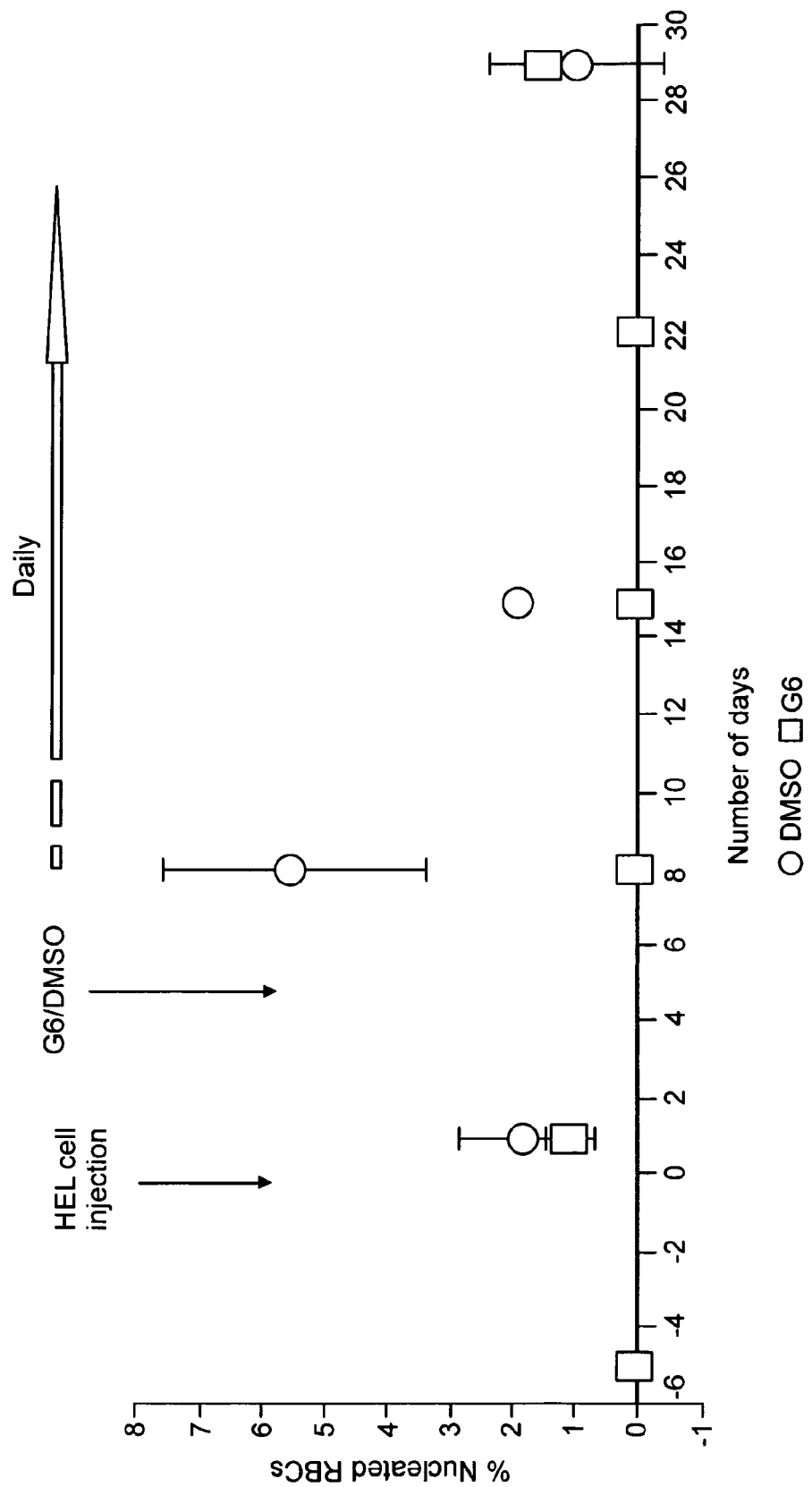
FIG. 14 is a graph showing G6 prevented Hel cell-induced appearance of nucleated red blood cells.
Figure 16A:
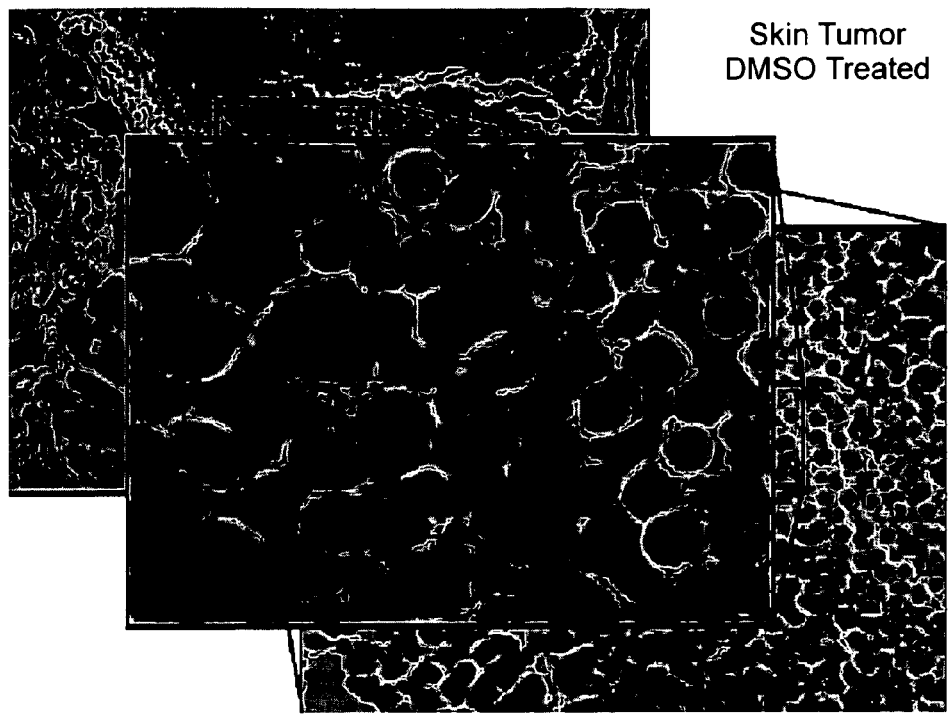
FIG. 16(A-C) is a series of hematoxylin and eosin stained images. Panel A shows a skin tumor treated with DMSO. Panel B shows treatment with G6 induced apoptosis in tumor cells. Panel C shows treatment with G6 induced marked necrosis and apoptosis in cellular elements of bone marrow.
Figure 16B:
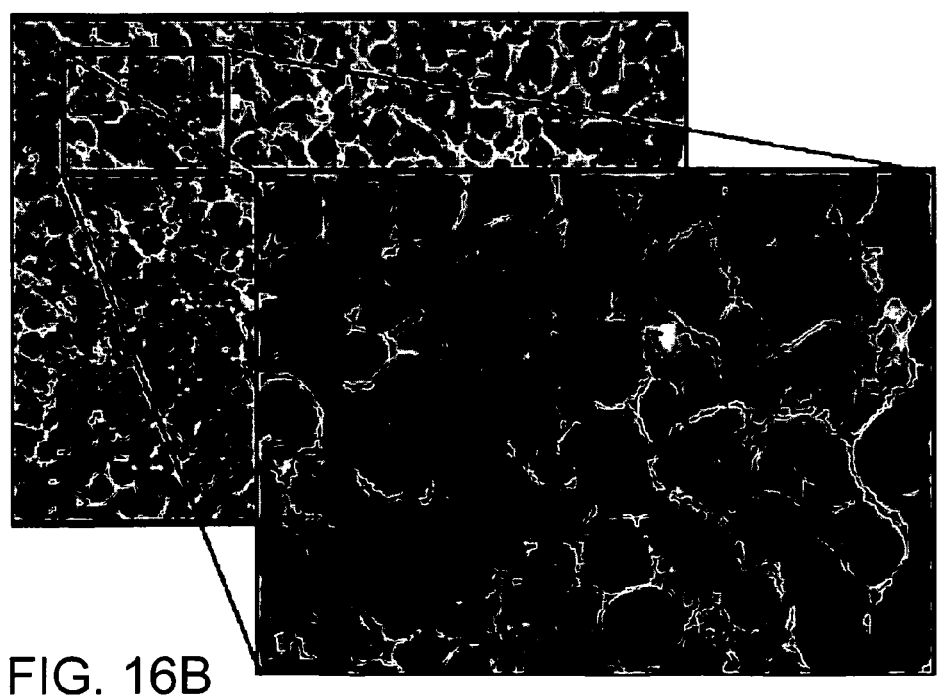
Figures 16C, 17:
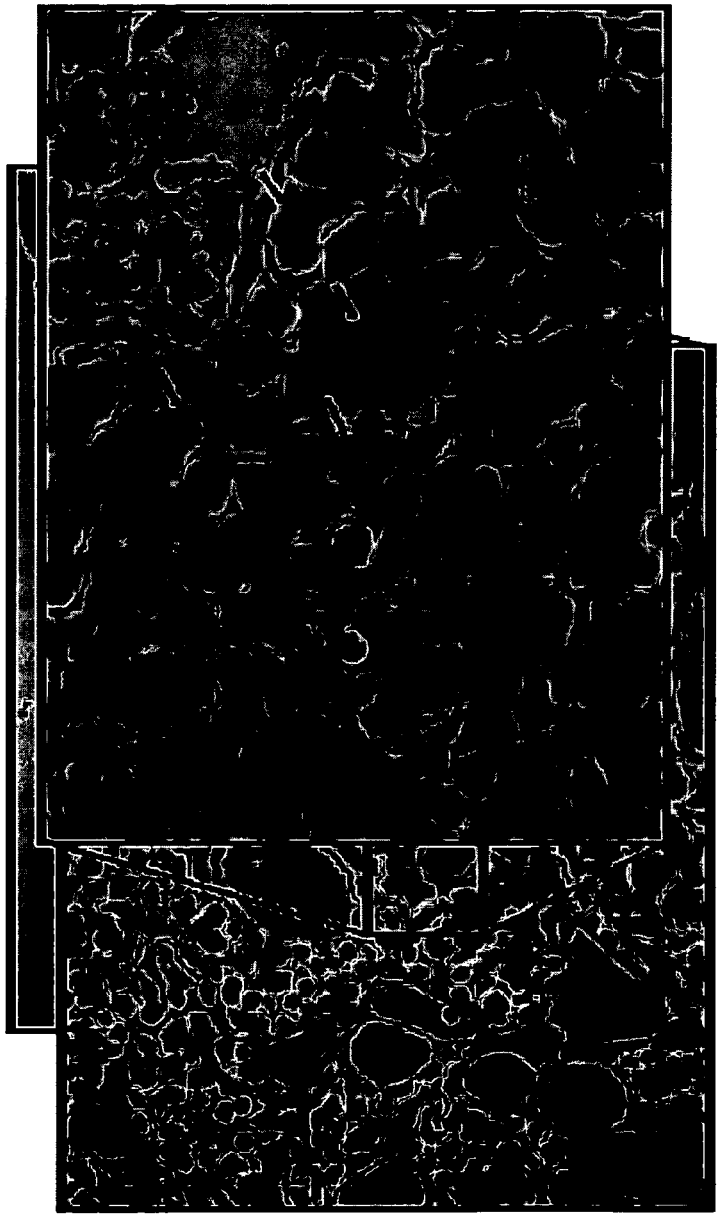
FIG. 17A is a table showing the percent growth inhibition and aqueous solubility of G6 and the G6 derivative compound D1.
FIG. 17B is a table showing the percent growth inhibition and aqueous solubility of the G6 derivatives compound D2 and D3.
FIG. 17C is a table showing the percent growth inhibition and aqueous solubility of the G6 derivative compounds D4 and D5.
FIG. 17D is a table showing the percent growth inhibition and aqueous solubility of the G6 derivative compounds D6 and D7.
FIG. 17E is a table showing the percent growth inhibition and aqueous solubility of the G6 derivative compounds D8 and D9.
FIG. 17F is a table showing the percent growth inhibition and aqueous solubility of the G6 derivative compounds D10 and D11.
FIG. 17G is a table showing the percent growth inhibition and aqueous solubility of the G6 derivative compounds D12 and D13.
Figure 17B:
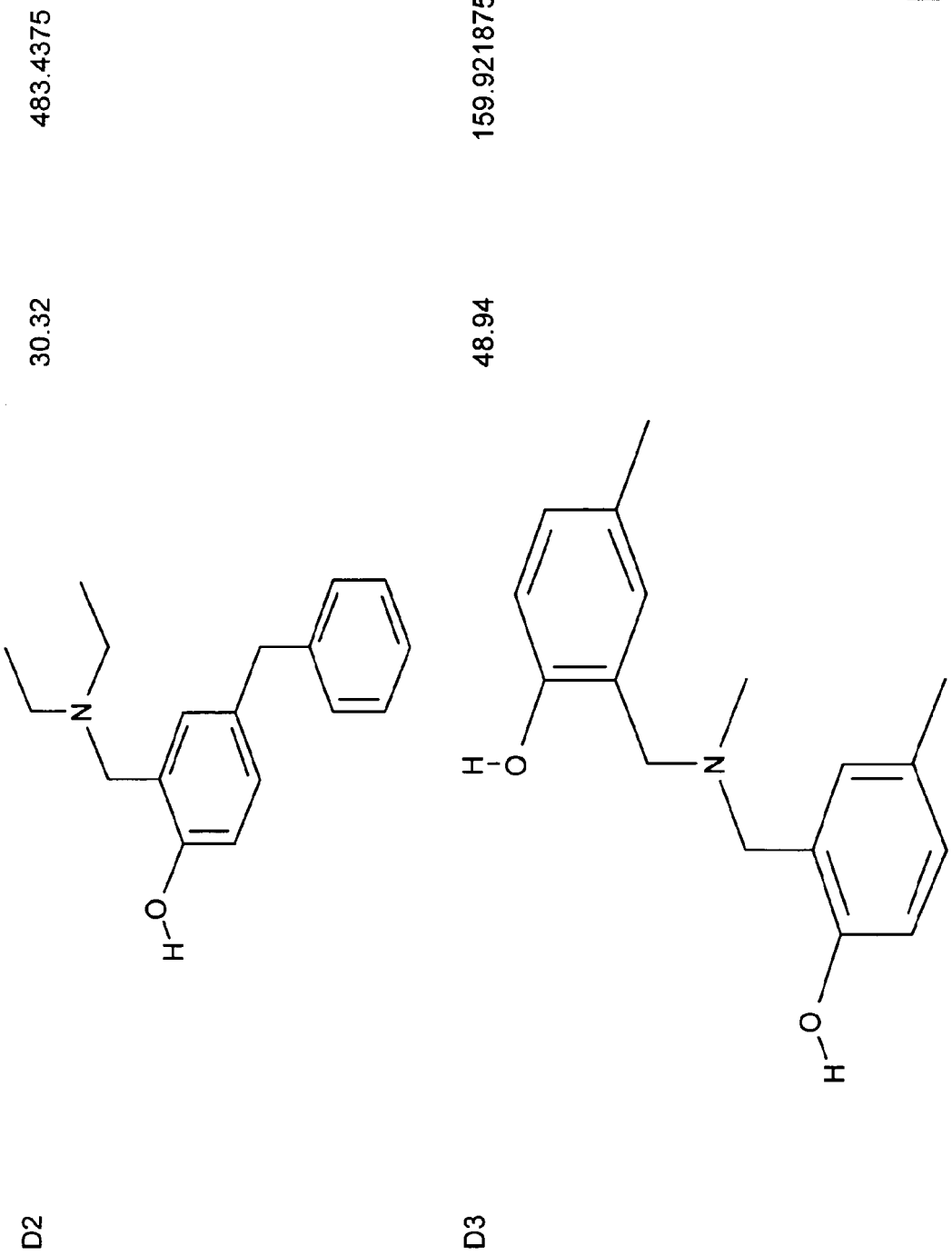

G6 is a selective Jak2 kinase inhibitor. G6 has been found to be a potent inhibitor of the Jak2-V617F mutation in vitro. FIG. 9 shows that G6 inhibits Jak2-V617F dependent HEL cell growth. A hypothesis, therefore, was that G6 effectively reduces Jak2-V617F-induced hematopoetic disease in a NOD-SCID (severe combined immunodeficient) mouse model. FIG. 10 is a schematic showing the experimental design. In the experiment, 5×10e6 HEL cells were injected into SCID mice, N=12 at day 0. At day 5, animals were dosed with either G6 or DMSO at 10 mg/kg/day, until day 29. Sub-mandibular bleed and necropsy were performed at time points as follows: 5 days prior to cell injection (day −5), day 1, day 8, day 15, day 22 and day 29 (indicated with a star on the schematic). In the experiment, the following measurable endpoints were assessed: total white blood cell (WBC) counts, percent of blast cells, percent of nucleated red blood cells, histopathology, including subcutaneous tumors, bone marrow and other organ systems. G6 alleviated HEL cell-induced leukocytosis to normal levels by 3 days following treatment (FIG. 11) and the percent of circulating blast cells (FIG. 12). Histopathology was assessed. FIG. 8E, panel A shows a normal monocyte. FIG. 13, panel B and panel C shows that HEL cell injection induced the appearance of blast cells. The graph shown in FIG. 14 shows that G6 prevented Hel cell-induced appearance of nucleated red blood cells (RBC). In examination of the gross anatomy of some of the skin tumors, it was found that there is no correlation between G6 treatment and tumor size (FIG. 15). FIG. 16, panel A shows a skin tumor that is treated with DMSO. FIG. 16, panel B shows that G6 induced apoptosis in tumor cells, and in cellular elements of bone marrow (FIG. 16, panel C).

Taken together, the results reported herein demonstrate that G6 reduced HEL cell-induced leukocytosis to normal levels by day 3 following treatment. Also, it was shown that G6 reduced HEL cell induced increase in the percent of circulating blast cells by 50 percent. The data presented herein shows that G6 prevented Hel cell-induced appearance of nucleated red blood cells. The histology presented demonstrates that G6 induced marked necrosis and apoptosis in cellular elements of the bone marrow and in solid tumors. It is also possible that G6 inhibits phosphorylation of Jak-STAT in NOD-SCID mouse tissues.

Alternative approaches that can be considered in these experiments are injecting the HEL cells intravenously, and using a dose dependent response in order to prevent cytotoxicity. Further, it may be desirable to aliquot out different vials of the drug for a week or more of treatment to prevent loss of efficacy.

Example 8

G6 Derivative Compounds

Figure 18B:
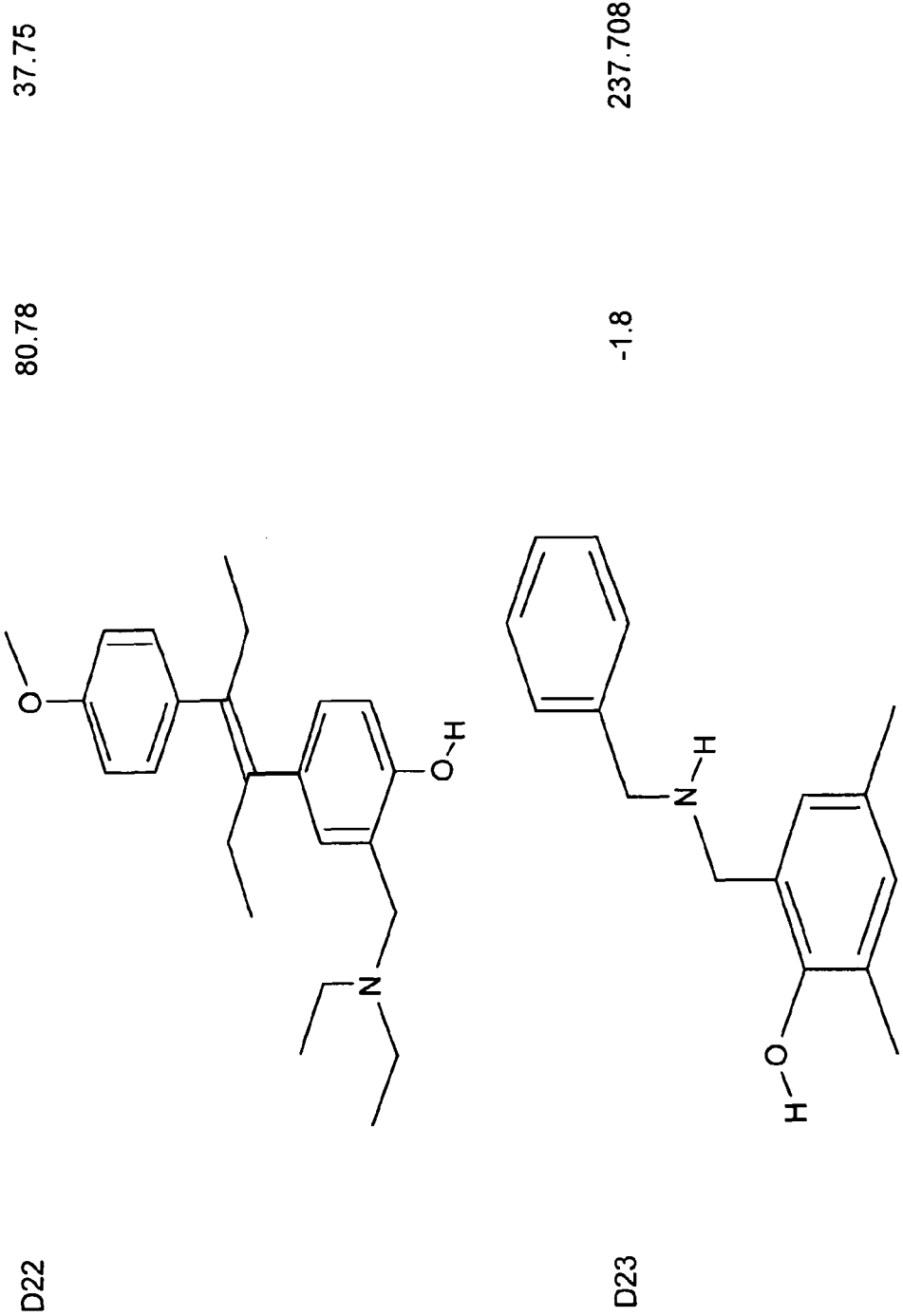
FIG. 18B is a table showing the percent growth inhibition and aqueous solubility of the G6 derivatives compound D22 and D23.
Figure 18C:
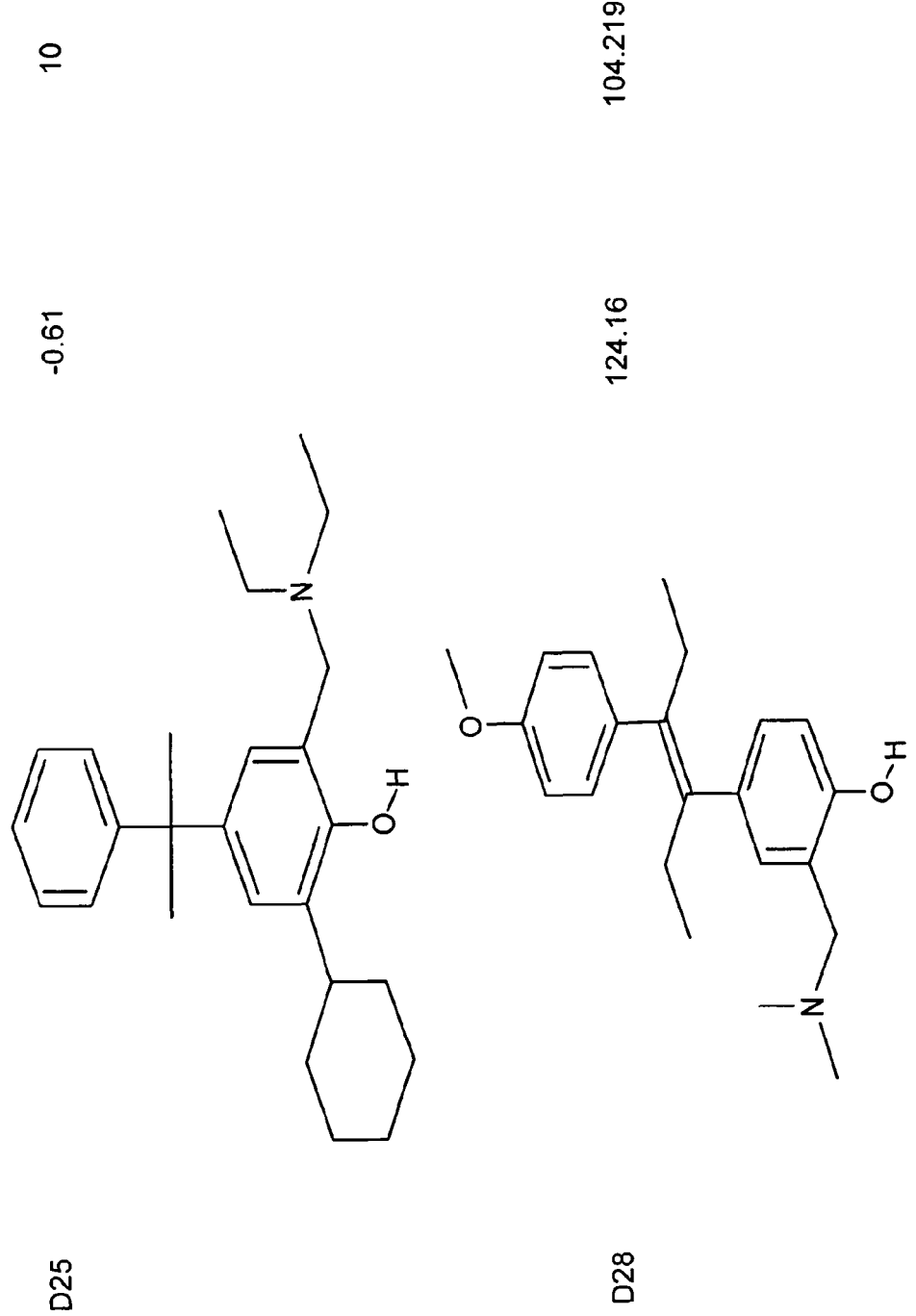
FIG. 18C is a table showing the percent growth inhibition and aqueous solubility of the G6 derivative compounds D25 and D28.
Figure 18D:
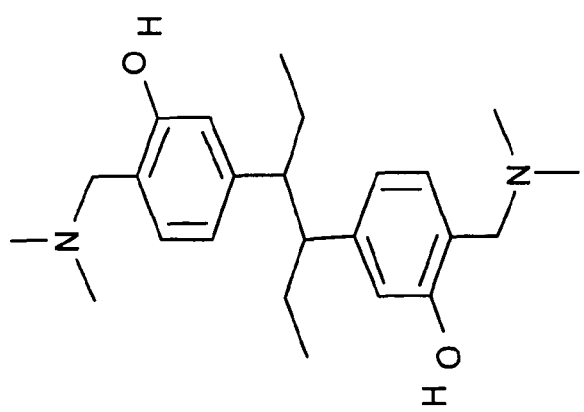
FIG. 18D is a table showing the percent growth inhibition and aqueous solubility of the G6 derivative compound D30.

Next, derivative compounds of G6 were obtained. FIG. 17A, panels A and B is a Table showing the percent growth inhibition and aqeuous solubility of the G6 derivative compounds D1-D14 (A) and D21-D23, D25, D28 and D30. As shown in the Table, there is a variation in the percent growth inhibition of the different derivatives. FIG. 18B is a Table showing a list of compound similar to G6. These studies provide valuable in formation as to which regions of G6 facilitate Jak2 inhibition and which regions mediate aqueous solubility, The data suggest that the stilbene (PhCH=CHPh) ring system is of importance for kinase inhibition (G6, D1 and D4). Also, the rigidity (orientation of the two phenyl rings) seems quite important (G6>D1 and D4). The aqueous solubility of the molecules is coming from polar groups (OH and NR); larger alkyl groups on the stilbenes will be less water soluble. Smaller alkyl group on the amine nitrogen would make it more water soluble. Water solubility can also be increased by preparing a HCl salt.

Example 9

Figure 19:
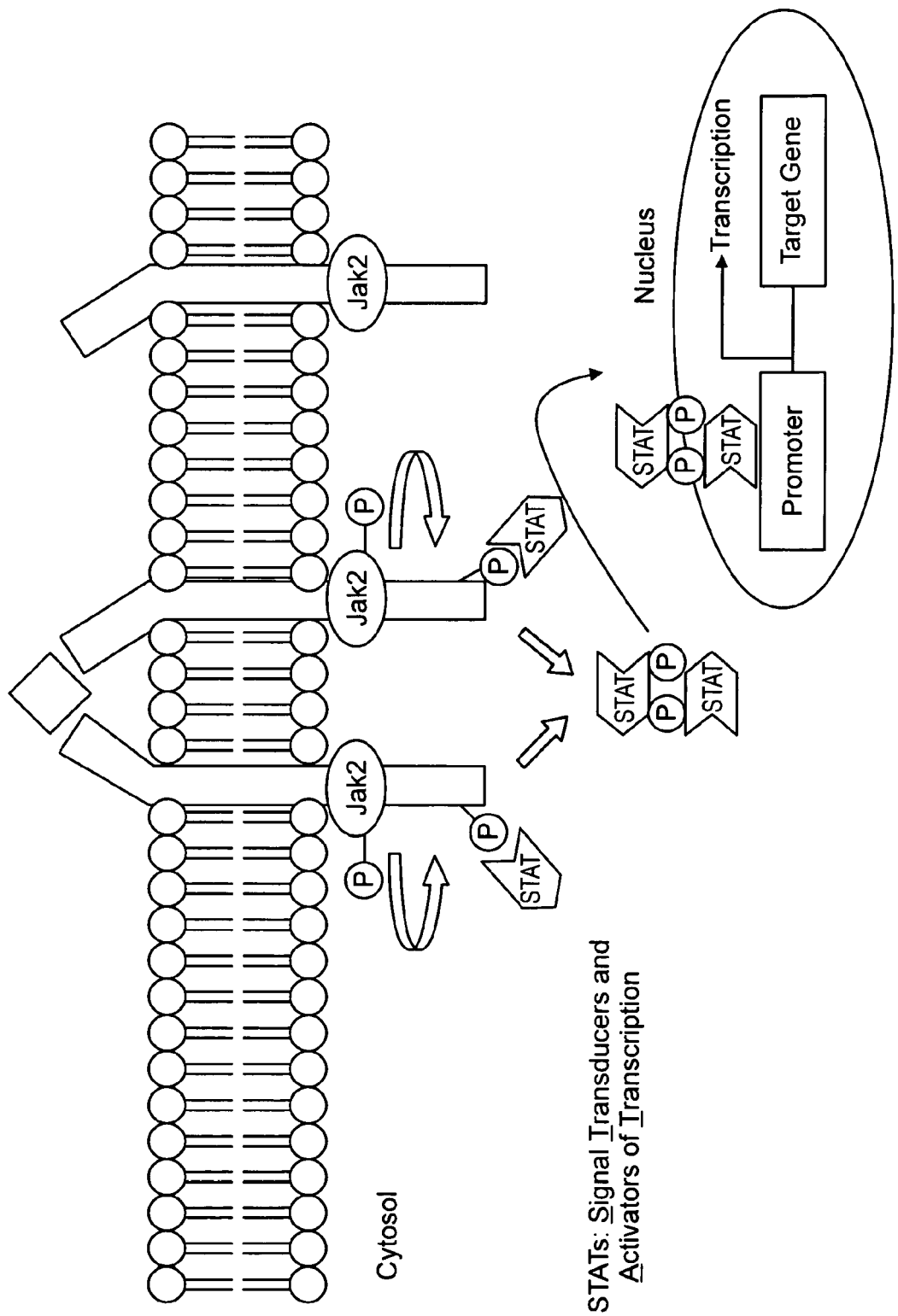
FIG. 19 is a schematic of the ligand-activated Jak/STAT signaling pathway.

Identification of Structure Function Correlation of a Novel Jak2 Small Molecule Inhibitor As described herein, Jak2 is a member of the Janus family of cytoplasmic tyrosine kinases, which also includes Jak1, Jak3 and Tyk2. Jak2 is expressed in numerous tissues, and is activated by cytokines, growth factors and GPCR ligands. Jak2 phosphorylates STATs, which modulate gene transcription. FIG. 19 is a schematic of the ligand activated Jak/STAT signaling pathway.

Jak2 signaling has pathological relevance and therapeutic implication. Jak2 is essential for life. It has been shown that Jak2-/- mice die prenatally due to the lack of erythropoesis. Jak2 signaling has been linked to cancer, as constitutive activation of Jak2 results in various leukemias, lymphomas, myelomas and solid mass tumors of the breast, prostate, head and neck. A link between Jak2 and cardiovascular disease has also been found, with a role for Jak2 being implicated in cardiac hypertrophy, cardiac ischemia-reperfusion, and heart failure. Jak2 has been found to play a role in myeloproliferative disorders. Activating mutations in Jak2 have been found in red blood cells, leading to polycythemia vera (Jak2-V617F), in platelets, leading to essential thrombocythemia (Jak2-V617F) and in monocytes, leading to primary myelofibrosis (Jak2-V617F).

Figure 20:
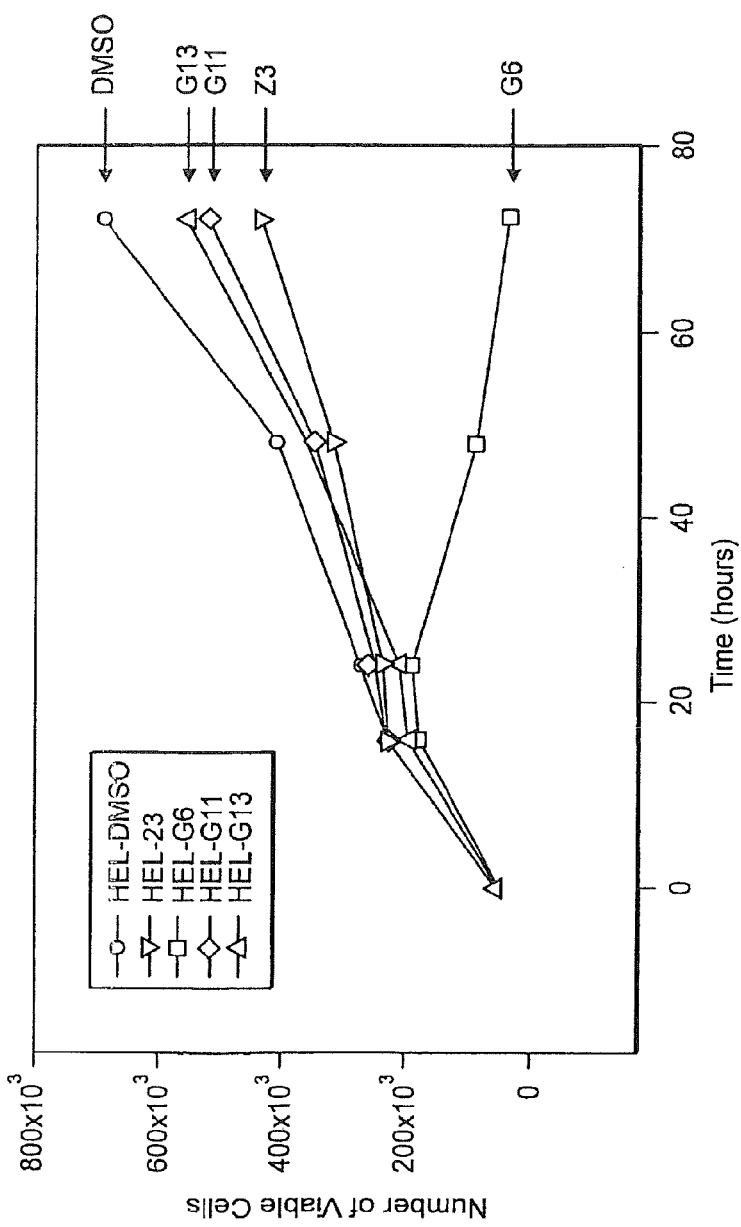
FIG. 20A is a graph showing G6 mediated inhibition of Jak2 dependent HEL cell proliferation.
FIG. 20B shows the statistical significance of the results shown in FIG. 20A.

In a first set of experiments, HEL cells were treated with G6 and the effect on Jak2 dependent proliferation was determined. As shown in FIG. 20, G6 mediated inhibition of Jak2 was dependent HEL cell proliferation. Other compounds were tested as well, including G13 and G11. The statistical significance between DMSO and G6 was $p=2.98 \times 10e-25$. The statistical significance between DMSO and G13 was $p=0.052$, and the statistical significance between DMSO and G11 was $p=00000000752$.

Figure 21:
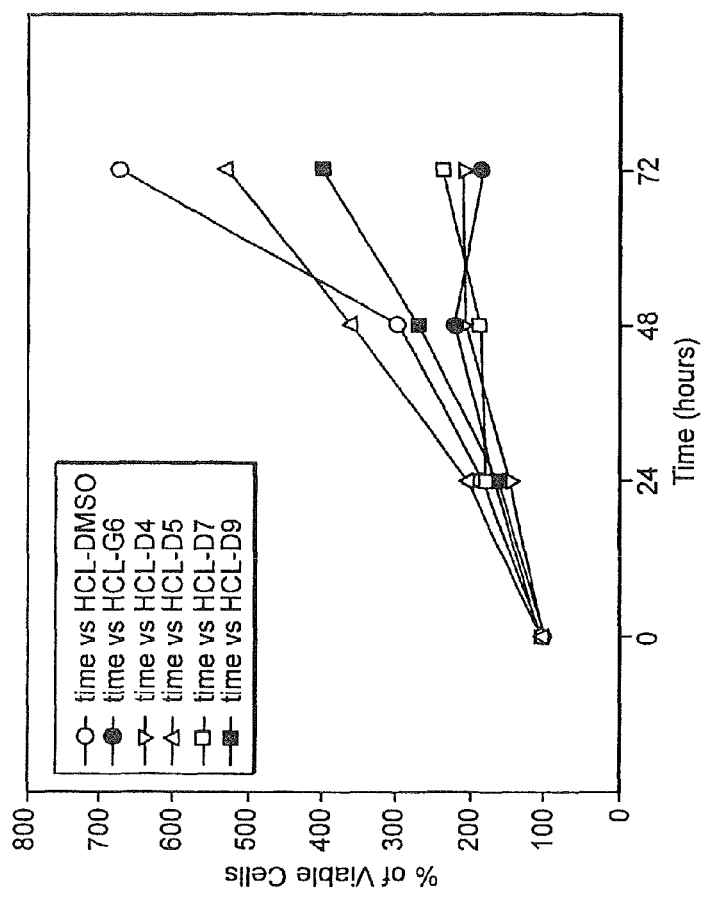
FIG. 21A is a graph showing G6 derivatives show different inhibition potentials.
FIG. 21B shows the statistical significance of the results shown in FIG. 21A.
Figure 22:
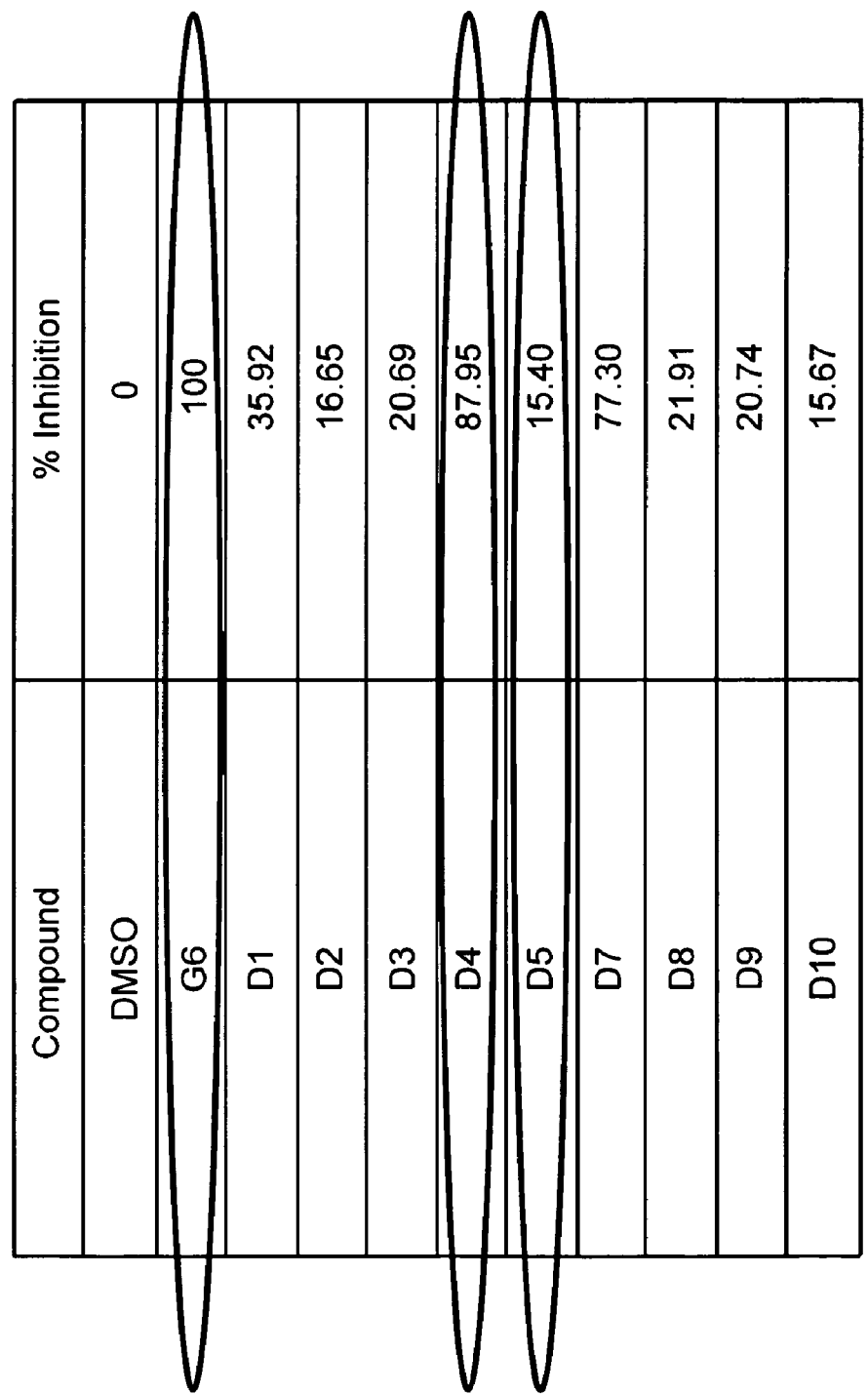
FIG. 22 is a Table listing some of the G6 derivatives and their inhibition potentials.

It is possible then that distinct regions of the native G6 structure may be responsible for mediating Jak2 dependent cell growth inhibition, versus its aqueous solubility. To test this, G6 and its derivatives were isolated from the NIH repository using in silico homology modeling. HEL cells were treated with DMSO, G6 and derivatives D1-D10 at a concentration of 25 µM. Cells were counted at the time points of 0, 24, 48 and 72 hours. A plot of cell count at each time point as a function of the time of treatment with drug was made. As shown in FIG. 21, G6 derivatives show different inhibition potentials. The statistical significance between DMSO and G6 was $p=5.718 \times 10e-13$. The statistical significance between DMSO and D5 was $p=0.086$. The statistical significance between G6 and D4 was $p=0.666$. As shown in the Table in FIG. 22, G6 derivatives show different inhibition potentials. While G6 shows 100% inhibition, D4 and D5 show 87.95% and 15.40%, respectively. The interactions of G6, D4 and D5 with the interaction loop of Jak2 were examined, shown in FIG. 23. Table 3, below, shows a comparison between G6, D4 and D5.

TABLE 3

| Compound | NCI No | Grid Score (Order of Decreasing Affinity) | Experimental result (% inhibition) |
|---|---|---|---|
| G6 | 33994 | −55.13 | 100% |
| D4 | 619076 | −45.703 | 87.95% |
| D5 | 607426 | −42.9 | 34.34% |

The data and results presented herein indicate that alterations in the different regions of the structure of G6 has shown different functional consequences.

The recitation of a listing of chemical groups in any definition of a variable herein includes definitions of that variable as any single group or combination of listed groups. The recitation of an element, an embodiment herein includes that element or embodiment as any single element or embodiment or in combination with any other element, embodiments or portions thereof.

The disclosures of each and every patent, patent application and publication cited herein are hereby incorporated herein by reference in their entirety.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

REFERENCES

1. Kaushansky K. The chronic myeloproliferative disorders and mutation of JAK2: Dameshek's 54 year old speculation comes of age. *Best Pract Res Clin Haematol.* 2007; 20: 5-12.
2. Lacout C, Pisani D F, Tulliez M, Gachelin F M, Vainchenker W, Villeval J L. JAK2V617F expression in murine hematopoietic cells leads to MPD mimicking human PV with secondary myelofibrosis. *Blood* 2006; 108: 1652-1660.
3. Zhang S J, Li J Y, Li W D, Song J H, Xu W, Qiu H X. The investigation of JAK2 mutation in Chinese myeloproliferative diseases-identification of a novel C616Y point mutation in a PV patient. *Int J Lab Hematol.* 2007; 29: 71-72.
4. Grunebach F, Bross-Bach U, Kanz L, Brossart P. Detection of a new JAK2 D620E mutation in addition to V617F in a patient with polycythemia vera. *Leukemia* 2006; 20: 2210-2211.
5. Schnittger S, Bacher U, Kern W, Schroder M, Haferlach T, Schoch C. Report on two novel nucleotide exchanges in the JAK2 pseudokinase domain: D620E and E627E. *Leukemia* 2006; 20: 2195-2197.
6. Sandberg E M, Ma X, He K, Frank S J, Ostrov D A, Sayeski P P. Identification of 1,2,3,4,5,6-hexabromocyclohexane as a small molecule inhibitor of Jak2 tyrosine kinase autophosphorylation. *J Med Chem.* 2005; 48: 2526-2533.

What is claimed is:

1. A method of treating a JAK2 mediated disorder in a subject identified as in need thereof comprising: administering to the subject a compound selected from the group consisting of:

2-methyl-1-phenyl-4-pyridin-2-yl-2-(2-pyridin-2-ylethyl)butan-1-one;

3-[5-[(4-oxo-4-phenyl-butan-2-ylidene)amino]pentyl-imino]-1-phenyl-butan-1-one (G13);

2-(diethylaminomethyl)-4-[4-[3-(diethylaminomethyl)-4-hydroxy-phenyl]hex-3-en-3-yl]phenol (G6);

2-dibutoxyphosphoryloxypentanenitrile (G31);

ytterbium(+3) cation trihydroxide (G33); and

4-[(1S)-6,7-diethoxy-1,2,3,4-tetrahydroisoquinolin-1-yl]benzonitrile (G40);

or a derivative, salt, hydrate or solvate thereof.

2. The method of claim 1, wherein the compound is 2-(diethylaminomethyl)-4-[4-[3-(diethylaminomethyl)-4-hydroxy-phenyl]hex-3-en-3-yl]phenol (G6), or a derivative thereof.

3. The method of claim 1, wherein the G6 derivative is a compound selected from the group consisting of:

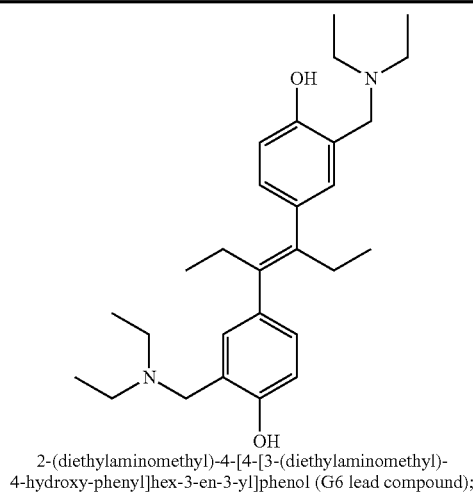

2-(diethylaminomethyl)-4-[4-[3-(diethylaminomethyl)-4-hydroxy-phenyl]hex-3-en-3-yl]phenol (G6 lead compound);

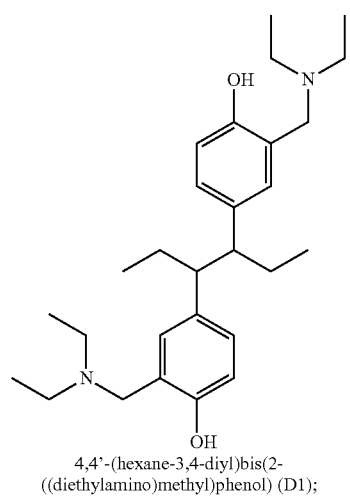

4,4'-(hexane-3,4-diyl)bis(2-((diethylamino)methyl)phenol) (D1);

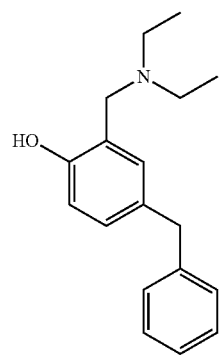 [SMILES: CCN(CC)Cc1cc(Cc2ccccc2)ccc1O]

4-benzyl-2-((diethylamino)methyl)phenol (D2);

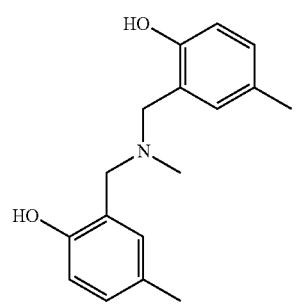 [SMILES: Cc1ccc(O)c(CN(C)Cc2cc(C)ccc2O)c1]

2,2'-(methylazanediyl)bis(methylene)bis(4-methylphenol) (D3);

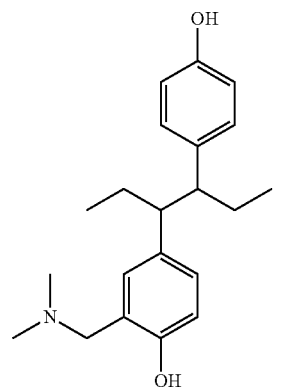 [SMILES: CCC(c1ccc(O)cc1)C(CC)c1ccc(O)c(CN(C)C)c1]

2-((dimethylamino)methyl)-4-(4-(4-hydroxyphenyl)hexan-3-yl)phenol (D4);

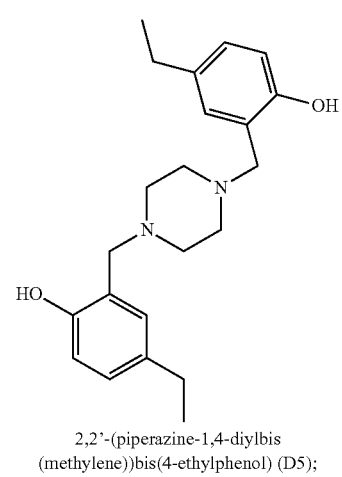

2,2'-(piperazine-1,4-diylbis(methylene))bis(4-ethylphenol) (D5);

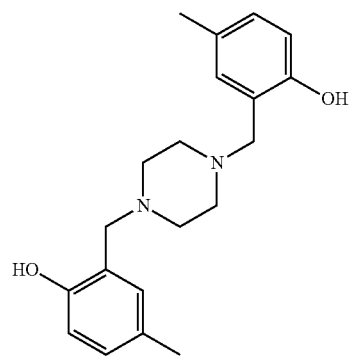 [SMILES: Cc1ccc(O)c(CN2CCN(Cc3cc(C)ccc3O)CC2)c1]

2,2'-(piperazine-1,4-diylbis
(methylene))bis(4-methylphenol) (D6);

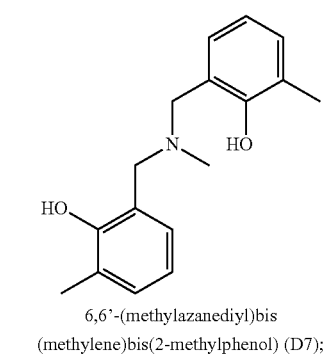

6,6'-(methylazanediyl)bis
(methylene)bis(2-methylphenol) (D7);

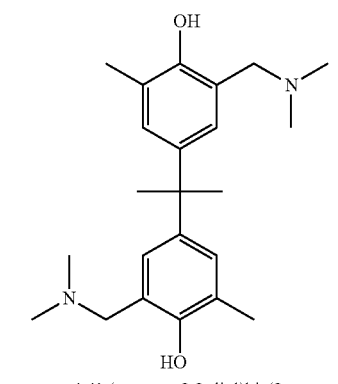

4,4'-(propane-2,2-diyl)bis(2-
((dimethylamino)methyl)-6-methylphenol) (D8);

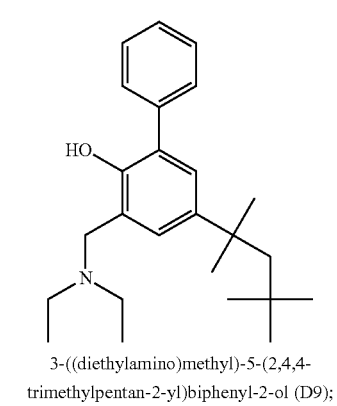

3-((diethylamino)methyl)-5-(2,4,4-
trimethylpentan-2-yl)biphenyl-2-ol) (D9);

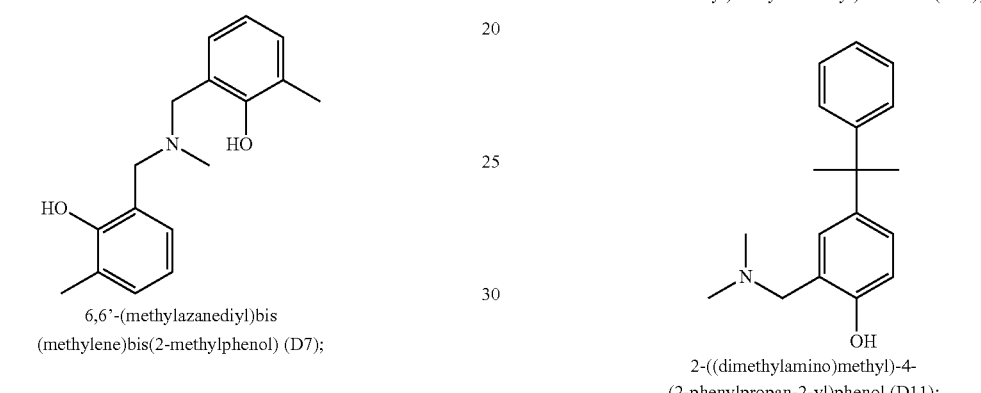

(E)-2,2'-(2-hydroxy-5-(4-(4-hydroxyphenyl)
hex-3-en-3-yl)benzylazanediyl)diethanol (D10);

2-((dimethylamino)methyl)-4-
(2-phenylpropan-2-yl)phenol (D11);

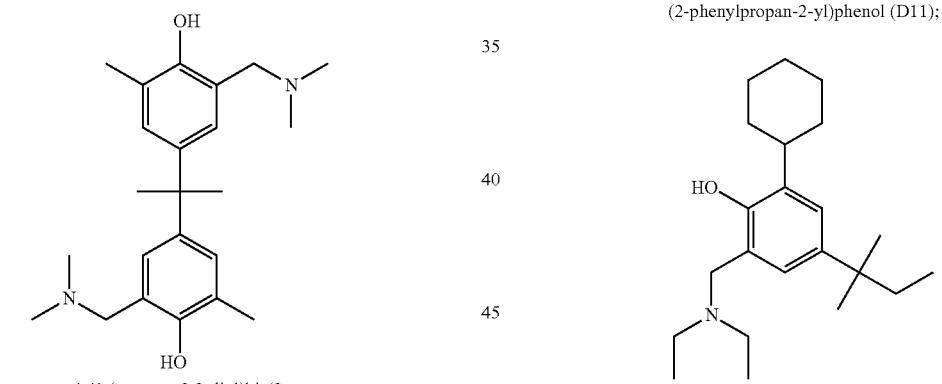

2-cyclohexyl-6-((diethylamino)methyl)-
4-tert-pentylphenol (D12);

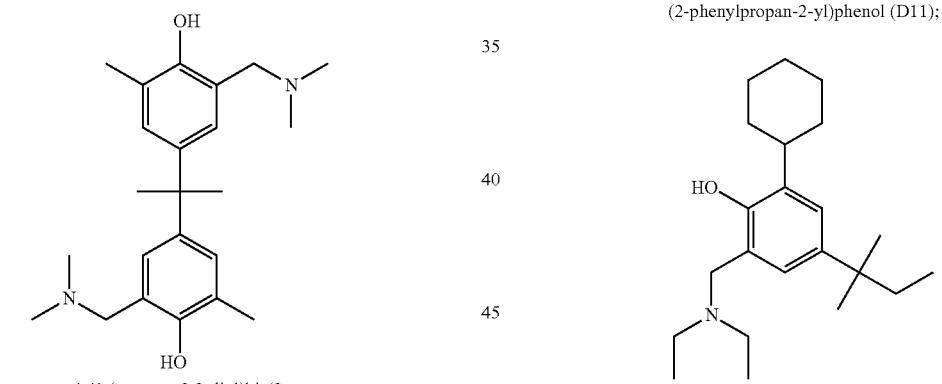

3-((diethylamino)methyl)-5-
tert-pentylbiphenyl-2-ol (D13);

-continued

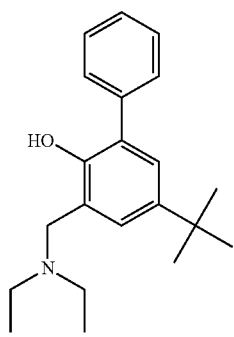 [SMILES: CCN(CC)Cc1cc(C(C)(C)C)cc(-c2ccccc2)c1O]

5-tert-butyl-3-((diethylamino)
methyl)biphenyl-2-ol (D14);

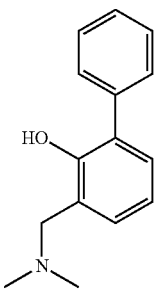

3-((dimethylamino)methyl)biphenyl-2-ol (D21);

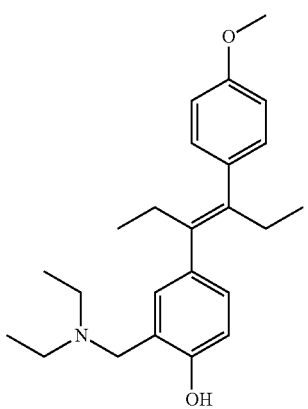 [SMILES: CC/C(=C(/CC)c1ccc(O)c(CN(CC)CC)c1)c1ccc(OC)cc1]

(E)-2-((diethylamino)methyl)-4-(4-
(4-methoxyphenyl)hex-3-en-3-yl)phenol (D22);

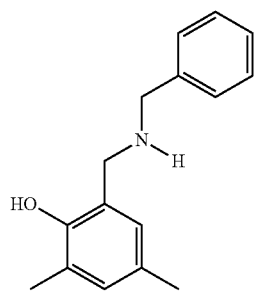 [SMILES: Cc1cc(C)c(O)c(CNCc2ccccc2)c1]

2-((benzylamino)methyl)-4,6-dimethylphenol (D23);

-continued

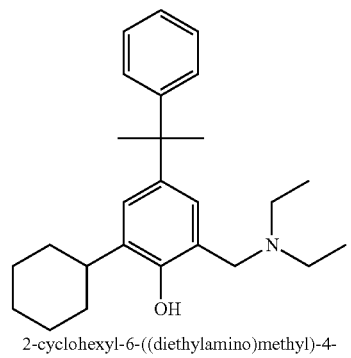

2-cyclohexyl-6-((diethylamino)methyl)-4-
(2-phenylpropan-2-yl)phenol (D25);

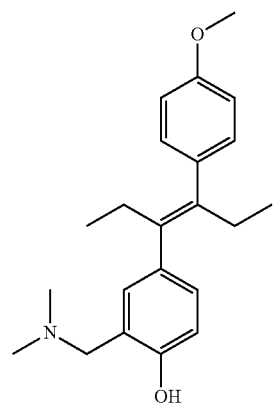 [SMILES: CC/C(=C(/CC)c1ccc(O)c(CN(C)C)c1)c1ccc(OC)cc1]

(E)-2-((dimethylamino)methyl)-4-(4-
(4-methoxyphenyl)hex-3-en-3-yl)phenol (D28);
and

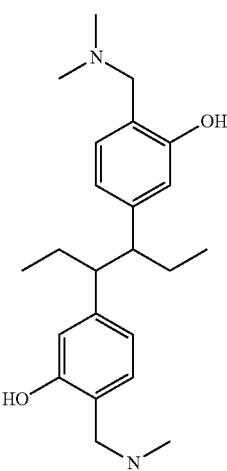

5,5'-(hexane-3,4-diyl)bis(2-
((dimethylamino)methyl)phenol) (D30);

or a salt, hydrate or solvate thereof.

4. The method of claim 1, wherein the subject is administered with an additional therapeutic agent.

5. The method of claim 4, wherein the compound and the additional therapeutic agent are administered simultaneously.

6. The method of claim 4, wherein the compound and the additional therapeutic agent are administered sequentially.

7. The method of claim 1, wherein the JAK2 mediated disorder is a hematological disease or disorder.

8. The method of claim 7, wherein the hematological disease or disorder is selected from the group consisting of:

polycythemia vera, essential thrombocythemia, angiogenic myeloid metaplasia, and primary myelofibrosis.

9. The method of claim 1, wherein the JAK2 mediated disorder is cancer.

10. The method of claim 9, wherein the cancer is selected from the group consisting of: leukemias, lymphomas, myelomas, and solid tumors.

11. The method of claim 10, wherein the leukemia is selected from the group consisting of: chronic myelogenous leukemia (CML), acute myeloid leukemia (AML) and acute promyelocytic leukemia (APL).

12. The method of claim 1, wherein the JAK2 mediated disorder is a cardiac disease or disorder.

13. The method of claim 12, wherein the cardiac disease or disorder is selected from the group consisting of: cardiac hypertrophy, cardiac ischemia-reperfusion, and heart failure.

14. The method of claim 1, wherein the compound is an inhibitor of the JAK2-V617F mutant.

15. The method of claim 1, wherein the compound inhibits JAK2 autophosphorylation.

16. The method of claim 1, wherein the compound is selected from the group consisting of: G6, G13, G31, G33 and G40.

17. The method of claim 3, wherein the compound is selected from the group consisting of: D4, D5, D28 and D30.

18. A method of treating a hematological disease or disorder in a subject identified as in need thereof comprising administering to the subject a compound selected from the group consisting of:

2-methyl-1-phenyl-4-pyridin-2-yl-2-(2-pyridin-2-ylethyl)butan-1-one;

3-[5-[(4-oxo-4-phenyl-butan-2-ylidene)amino]pentyl-imino]-1-phenyl-butan-1-one (G13);

2-(diethylaminomethyl)-4-[4-[3-(diethylaminomethyl)-4-hydroxy-phenyl]hex-3-en-3-yl]phenol (G6);

2-dibutoxyphosphoryloxypentanenitrile (G31);

ytterbium(+3) cation trihydroxide (G33); and

4-[(1S)-6,7-diethoxy-1,2,3,4-tetrahydroisoquinolin-1-yl]benzonitrile (G40); or a salt, derivative, hydrate or solvate thereof.

19. A method for reducing JAK2-dependent cell growth comprising contacting a cell with a JAK2 inhibitor compound selected from the group consisting of:

2-methyl-1-phenyl-4-pyridin-2-yl-2-(2-pyridin-2-ylethyl)butan-1-one;

3-[5-[(4-oxo-4-phenyl-butan-2-ylidene)amino]pentyl-imino]-1-phenyl-butan-1-one (G13);

2-(diethylaminomethyl)-4-[4-[3-(diethylaminomethyl)-4-hydroxy-phenyl]hex-3-en-3-yl]phenol (G6);

2-dibutoxyphosphoryloxypentanenitrile (G31);

ytterbium(+3) cation trihydroxide (G33); and

4-[(1S)-6,7-diethoxy-1,2,3,4-tetrahydroisoquinolin-1-yl]benzonitrile (G40); or a compound selected from the group consisting of:

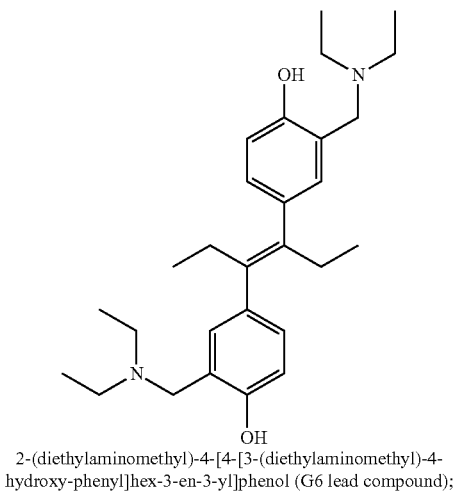

2-(diethylaminomethyl)-4-[4-[3-(diethylaminomethyl)-4-hydroxy-phenyl]hex-3-en-3-yl]phenol (G6 lead compound);

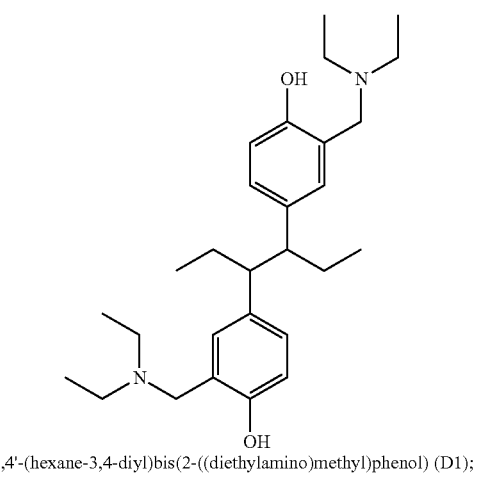

4,4'-(hexane-3,4-diyl)bis(2-((diethylamino)methyl)phenol) (D1);

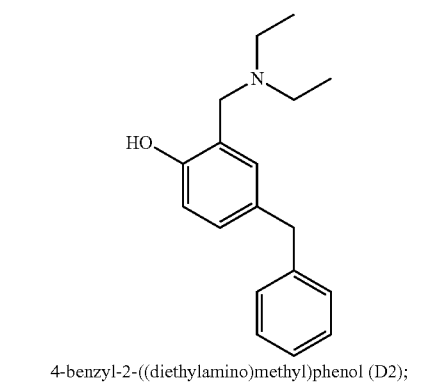

4-benzyl-2-((diethylamino)methyl)phenol (D2);

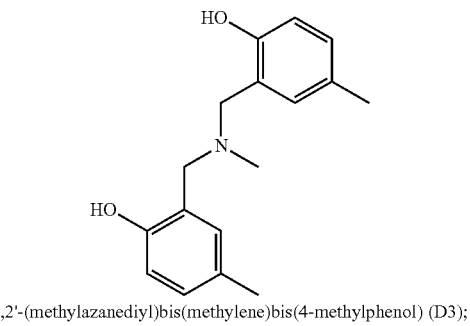

2,2'-(methylazanediyl)bis(methylene)bis(4-methylphenol) (D3);

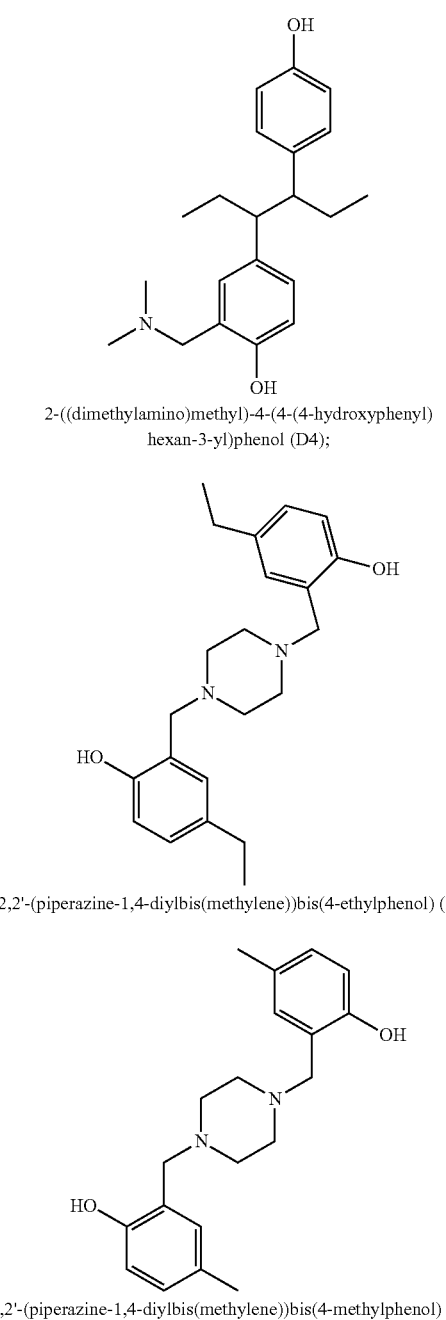

2-((dimethylamino)methyl)-4-(4-(4-hydroxyphenyl)hexan-3-yl)phenol (D4);

2,2'-(piperazine-1,4-diylbis(methylene))bis(4-ethylphenol) (D5);

2,2'-(piperazine-1,4-diylbis(methylene))bis(4-methylphenol) (D6);

6,6'-(methylazanediyl)bis(methylene)bis(2-methylphenol) (D7);

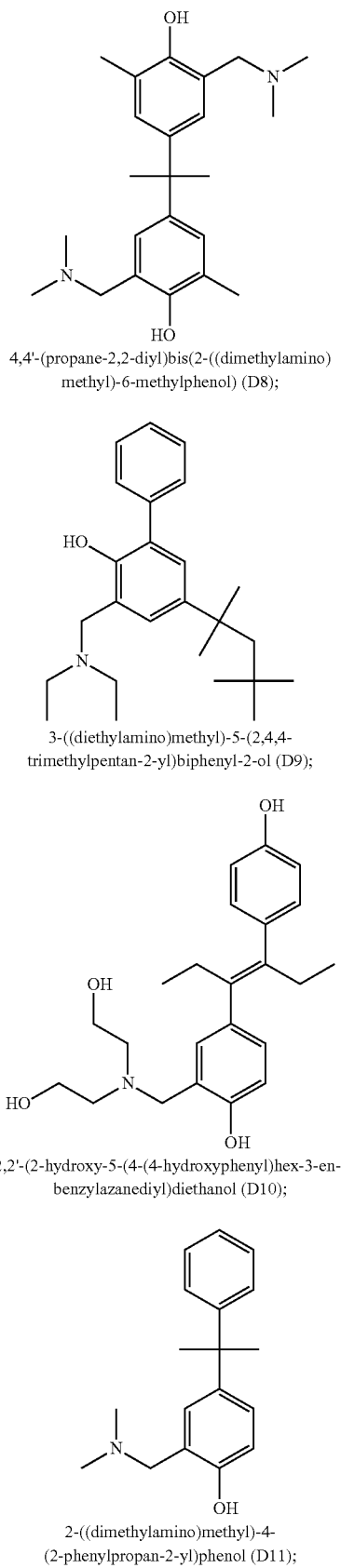

4,4'-(propane-2,2-diyl)bis(2-((dimethylamino)methyl)-6-methylphenol) (D8);

3-((diethylamino)methyl)-5-(2,4,4-trimethylpentan-2-yl)biphenyl-2-ol (D9);

(E)-2,2'-(2-hydroxy-5-(4-(4-hydroxyphenyl)hex-3-en-3-yl)benzylazanediyl)diethanol (D10);

2-((dimethylamino)methyl)-4-(2-phenylpropan-2-yl)phenol (D11);

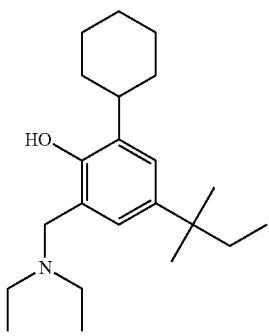 [SMILES: CCN(CC)Cc1cc(C(C)(C)CC)cc(C2CCCCC2)c1O]

2-cyclohexyl-6-((diethylamino)methyl)-
4-tert-pentylphenol (D12);

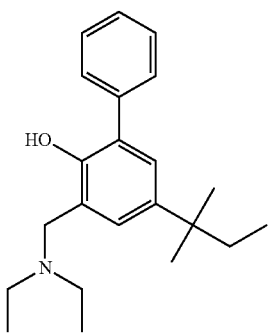 [SMILES: CCN(CC)Cc1cc(C(C)(C)CC)cc(-c2ccccc2)c1O]

3-((diethylamino)methyl)-5-tert-pentylbiphenyl-2-ol (D13);

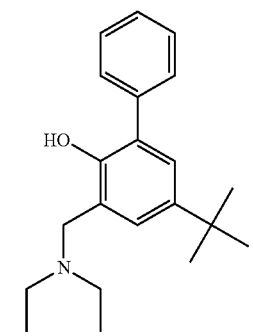 [SMILES: CCN(CC)Cc1cc(C(C)(C)C)cc(-c2ccccc2)c1O]

5-tert-butyl-3-((diethylamino)methyl)biphenyl-2-ol (D14);

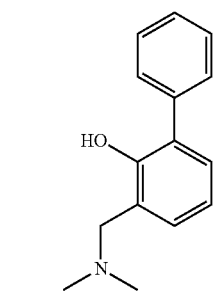

3-((dimethylamino)methyl)biphenyl-2-ol (D21);

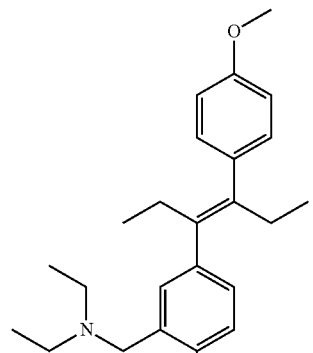

(E)-2-((diethylamino)methyl)-4-(4-(4-
methoxyphenyl)hex-3-en-3-yl)phenol (D22);

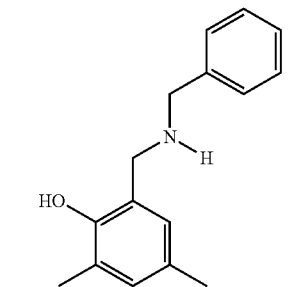 [SMILES: Cc1cc(C)c(O)c(CNCc2ccccc2)c1]

2-((benzylamino)methyl)-4,6-dimethylphenol (D23);

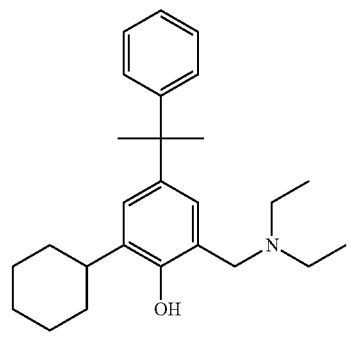 [SMILES: CCN(CC)Cc1cc(C(C)(C)c2ccccc2)cc(C2CCCCC2)c1O]

2-cyclohexyl-6-((diethylamino)methyl)-4-
(2-phenylpropan-2-yl)phenol (D25);

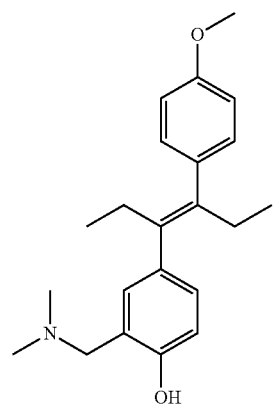 [SMILES: CC/C(=C(/CC)c1ccc(O)c(CN(C)C)c1)c1ccc(OC)cc1]

(E)-2-((dimethylamino)methyl)-4-(4-
(4-methoxyphenyl)hex-3-en-3-yl)phenol (D28);
and

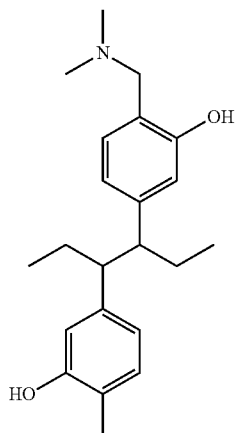

5,5'-(hexane-3,4-diyl)bis(2-((dimethylamino)methyl)phenol) (D30);

or a derivative, salt, hydrate, or solvate thereof.

20. The method of claim 1, wherein the subject is identified as having the JAK2-V617F mutant.

21. The method of claim 1, wherein the subject is identified as having the K603Q, D620E or C644S mutation in the JAK2 JH2 domain.

22. The method of claim 1, wherein the subject is identified as having the K603Q, D620E and C644S mutations in the JAK2 JH2 domain.

23. The method of claim 22, wherein the subject is identified as having the K603Q, D620E and C644S mutations in the JAK2 JH2 domain and is identified as not having the JAK2-V617F mutant.

24. The method of claim 1, wherein the subject is a human.

25. A pharmaceutical composition comprising a compound capable of modulating JAK2 activity selected from one or more compounds elected from the group consisting of:

2-methyl-1-phenyl-4-pyridin-2-yl-2-(2-pyridin-2-ylethyl)butan-1-one;

3-[5-[(4-oxo-4-phenyl-butan-2-ylidene)amino]pentyl-imino]-1-phenyl-butan-1-one (G13);

2-(diethylaminomethyl)-4-[4-[3-(diethylaminomethyl)-4-hydroxy-phenyl]hex-3-en-3-yl]phenol (G6);

2-dibutoxyphosphoryloxypentanenitrile (G31);

ytterbium(+3) cation trihydroxide (G33); and

4-[(1S)-6,7-diethoxy-1,2,3,4-tetrahydroisoquinolin-1-yl]benzonitrile (G40) or a compound selected from the group consisting of:

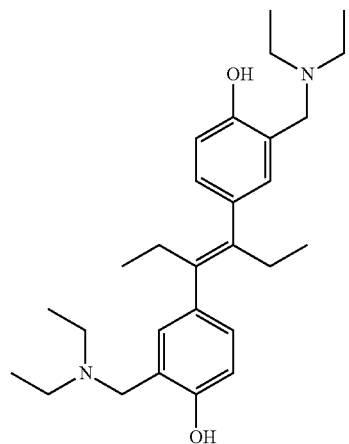

2-(diethylaminomethyl)-4-[4-[3-(diethylaminomethyl)-4-hydroxy-phenyl]hex-3-en-3-yl]phenol (G6 lead compound);

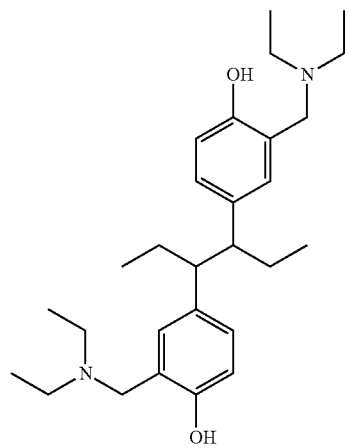 [SMILES: CCC(c1ccc(O)c(CN(CC)CC)c1)C(CC)c1ccc(O)c(CN(CC)CC)c1]

4,4'-(hexane-3,4-diyl)bis(2-((diethylamino)methyl)phenol) (D1);

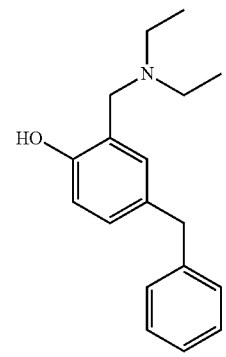 [SMILES: CCN(CC)Cc1cc(Cc2ccccc2)ccc1O]

4-benzyl-2-((diethylamino)methyl)phenol (D2);

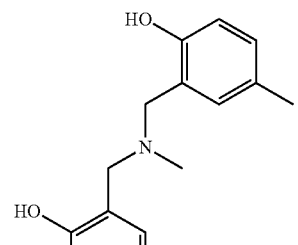

2,2'-(methylazanediyl)bis(methylene)
bis(4-methylphenol) (D3);

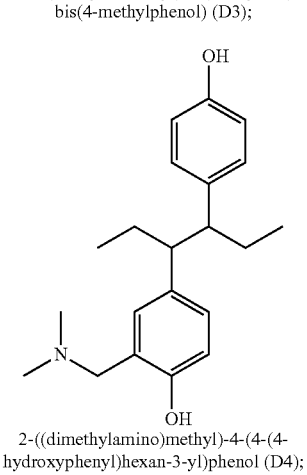

2-((dimethylamino)methyl)-4-(4-(4-
hydroxyphenyl)hexan-3-yl)phenol (D4);

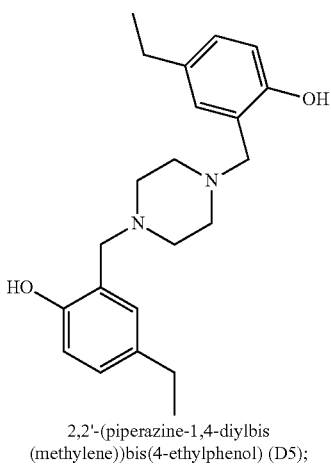

2,2'-(piperazine-1,4-diylbis
(methylene))bis(4-ethylphenol) (D5);

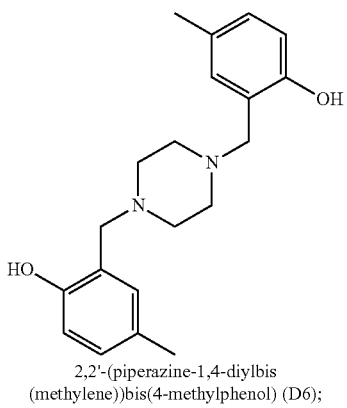

2,2'-(piperazine-1,4-diylbis
(methylene))bis(4-methylphenol) (D6);

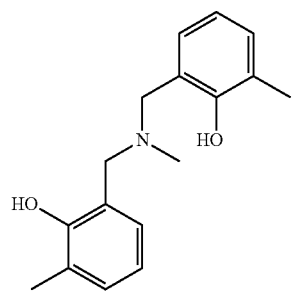 [SMILES: Cc1cccc(CN(C)Cc2cccc(C)c2O)c1O]

6,6'-(methylazanediyl)bis
(methylene)bis(2-methylphenol) (D7);

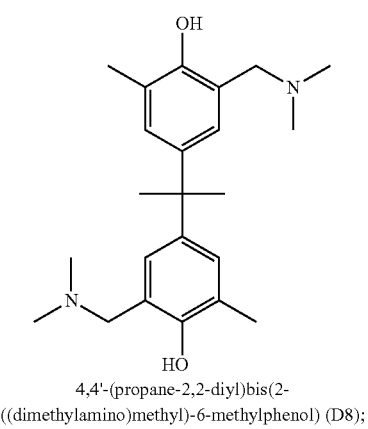

4,4'-(propane-2,2-diyl)bis(2-
((dimethylamino)methyl)-6-methylphenol) (D8);

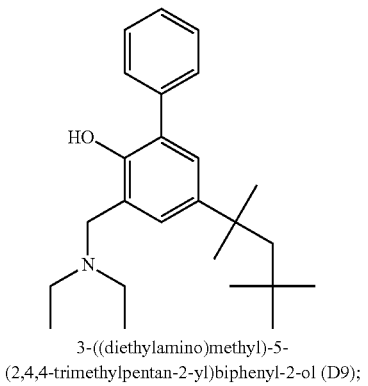

3-((diethylamino)methyl)-5-
(2,4,4-trimethylpentan-2-yl)biphenyl-2-ol (D9);

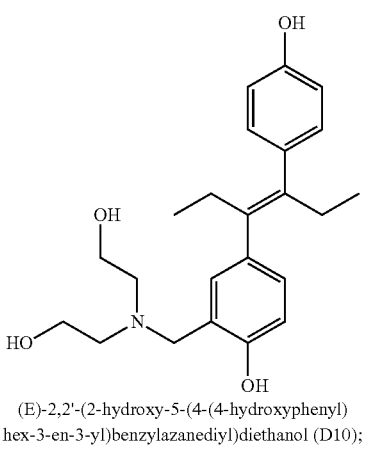

(E)-2,2'-(2-hydroxy-5-(4-(4-hydroxyphenyl)
hex-3-en-3-yl)benzylazanediyl)diethanol (D10);

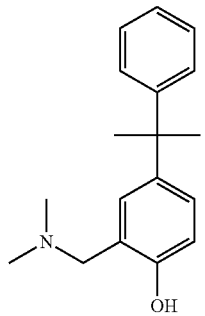

2-((dimethylamino)methyl)-4-
(2-phenylpropan-2-yl)phenol (D11);

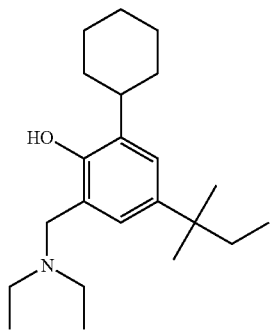 [SMILES: CCN(CC)Cc1cc(C(C)(C)CC)cc(C2CCCCC2)c1O]

2-cyclohexyl-6-((diethylamino)
methyl)-4-tert-pentylphenol (D12);

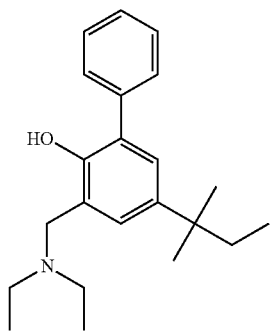 [SMILES: CCN(CC)Cc1cc(C(C)(C)CC)cc(-c2ccccc2)c1O]

3-((diethylamino)methyl)-
5-tert-pentylbiphenyl-2-ol (D13);

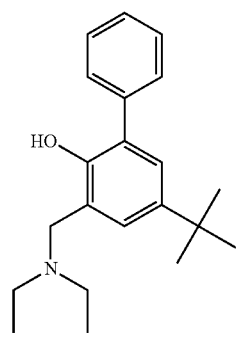 [SMILES: CCN(CC)Cc1cc(C(C)(C)C)cc(-c2ccccc2)c1O]

5-tert-butyl-3-((diethylamino)
methyl)biphenyl-2-ol (D14);

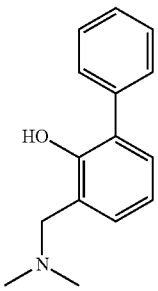 [SMILES: CN(C)Cc1cccc(-c2ccccc2)c1O]

3-((dimethylamino)methyl)biphenyl-2-ol (D21);

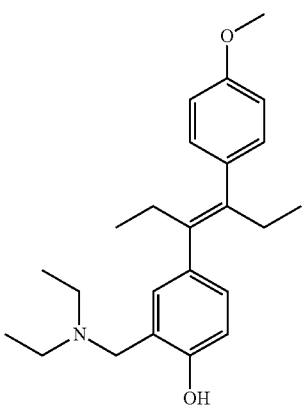 [SMILES: CC/C(=C(/CC)c1ccc(O)c(CN(CC)CC)c1)c1ccc(OC)cc1]

(E)-2-((diethylamino)methyl)-4-(4-
(4-methoxyphenyl)hex-3-en-3-yl)phenol (D22);

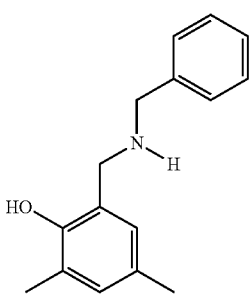 [SMILES: Cc1cc(C)c(O)c(CNCc2ccccc2)c1]

2-((benzylamino)methyl)-4,6-dimethylphenol (D23);

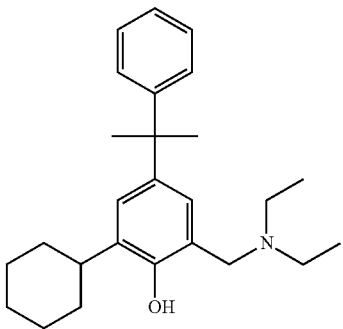 [SMILES: CCN(CC)Cc1cc(C(C)(C)c2ccccc2)cc(C2CCCCC2)c1O]

2-cyclohexyl-6-((diethylamino)
methyl)-4-(2-phenylpropan-2-yl)phenol (D25);

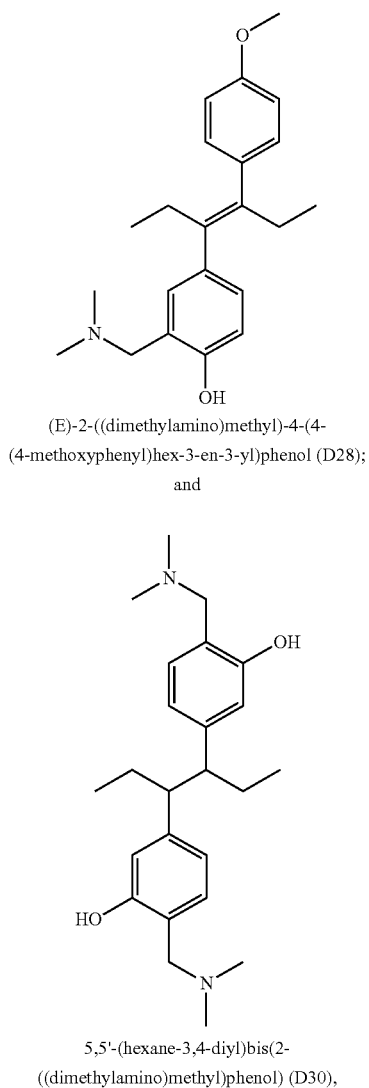

(E)-2-((dimethylamino)methyl)-4-(4-(4-methoxyphenyl)hex-3-en-3-yl)phenol (D28); and

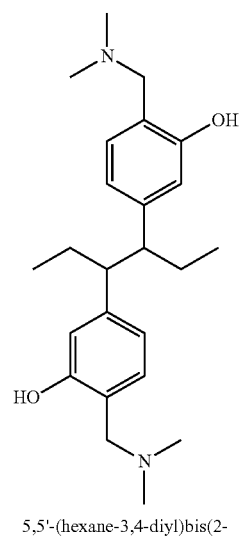

5,5'-(hexane-3,4-diyl)bis(2-((dimethylamino)methyl)phenol) (D30), or a pharmaceutically acceptable ester, salt, derivative, hydrate, solvate, or prodrug thereof, together with a pharmaceutically acceptable carrier.

26. A method of treating a JAK2 mediated disorder selected from the group consisting of cancer, a hematological disease or disorder, and a cardiac disease or disorder, in a subject identified as in need thereof, the method comprising: administering to the subject a compound selected from the group consisting of:

2-methyl-1-phenyl-4-pyridin-2-yl-2-(2-pyridin-2-ylethyl) butan-1-one;

3-[5-[(4-oxo-4-phenyl-butan-2-ylidene)amino]pentyl-imino]-1-phenyl-butan-1-one (G13);

2-(diethylaminomethyl)-4-[4-[3-(diethylaminomethyl)-4-hydroxy-phenyl]hex-3-en-3-yl]phenol (G6);

2-dibutoxyphosphoryloxypentanenitrile (G31);

ytterbium(+3) cation trihydroxide (G33);

4-[(1S)-6,7-diethoxy-1,2,3,4-tetrahydroisoquinolin-1-yl] benzonitrile (G40);

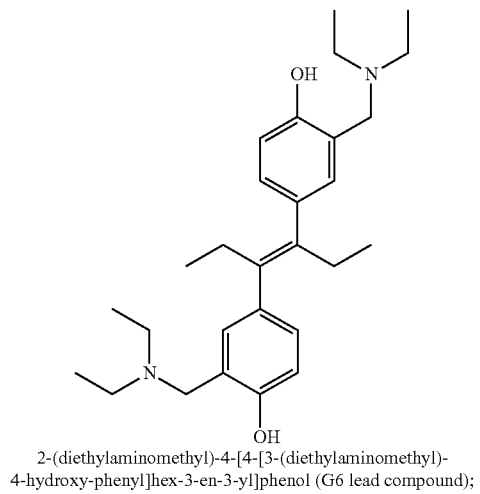

2-(diethylaminomethyl)-4-[4-[3-(diethylaminomethyl)-4-hydroxy-phenyl]hex-3-en-3-yl]phenol (G6 lead compound);

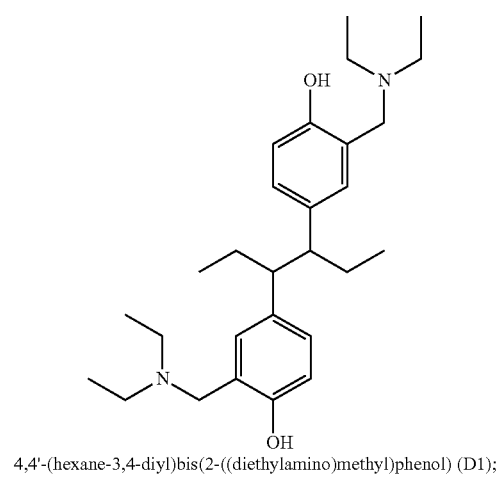

4,4'-(hexane-3,4-diyl)bis(2-((diethylamino)methyl)phenol) (D1);

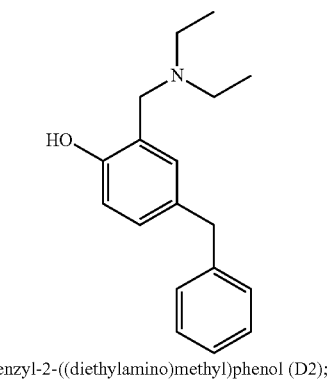

4-benzyl-2-((diethylamino)methyl)phenol (D2);

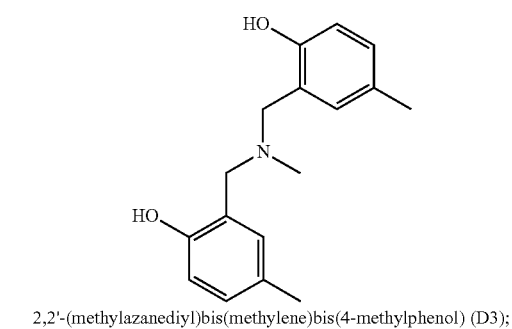

2,2'-(methylazanediyl)bis(methylene)bis(4-methylphenol) (D3);

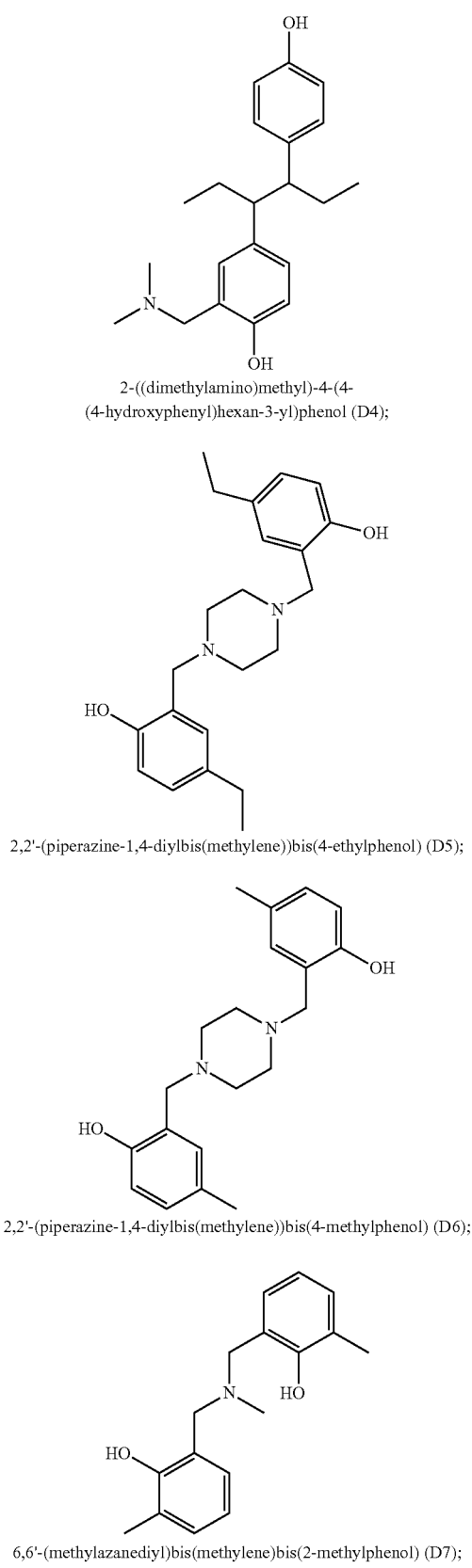

2-((dimethylamino)methyl)-4-(4-(4-hydroxyphenyl)hexan-3-yl)phenol (D4);

2,2'-(piperazine-1,4-diylbis(methylene))bis(4-ethylphenol) (D5);

2,2'-(piperazine-1,4-diylbis(methylene))bis(4-methylphenol) (D6);

6,6'-(methylazanediyl)bis(methylene)bis(2-methylphenol) (D7);

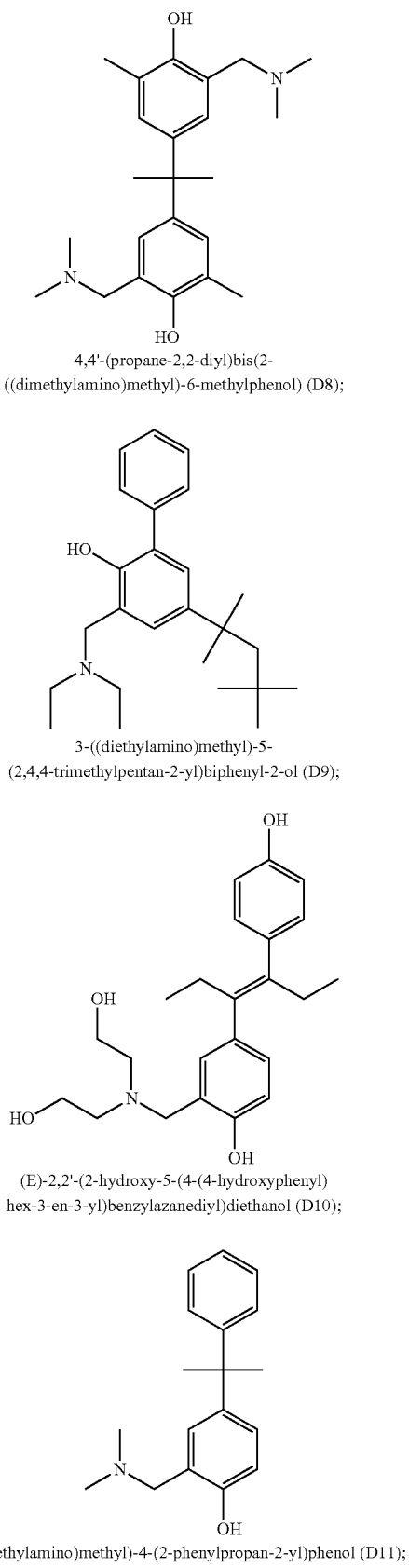

4,4'-(propane-2,2-diyl)bis(2-((dimethylamino)methyl)-6-methylphenol) (D8);

3-((diethylamino)methyl)-5-(2,4,4-trimethylpentan-2-yl)biphenyl-2-ol (D9);

(E)-2,2'-(2-hydroxy-5-(4-(4-hydroxyphenyl)hex-3-en-3-yl)benzylazanediyl)diethanol (D10);

2-((dimethylamino)methyl)-4-(2-phenylpropan-2-yl)phenol (D11);

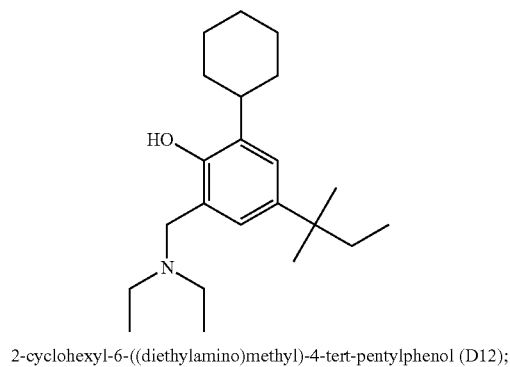
2-cyclohexyl-6-((diethylamino)methyl)-4-tert-pentylphenol (D12);
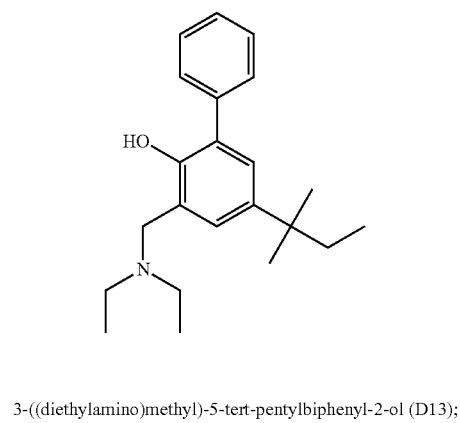
3-((diethylamino)methyl)-5-tert-pentylbiphenyl-2-ol (D13);
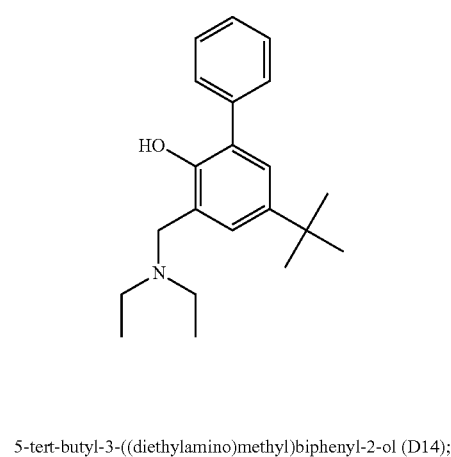
5-tert-butyl-3-((diethylamino)methyl)biphenyl-2-ol (D14);
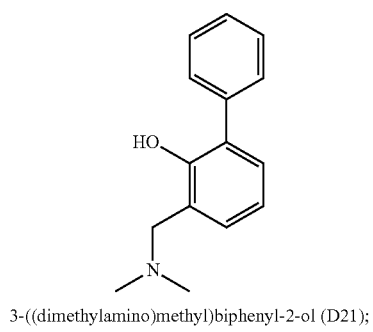
3-((dimethylamino)methyl)biphenyl-2-ol (D21);
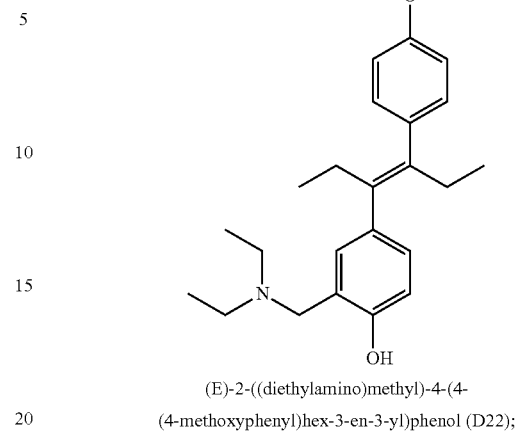
(E)-2-((diethylamino)methyl)-4-(4-(4-methoxyphenyl)hex-3-en-3-yl)phenol (D22);
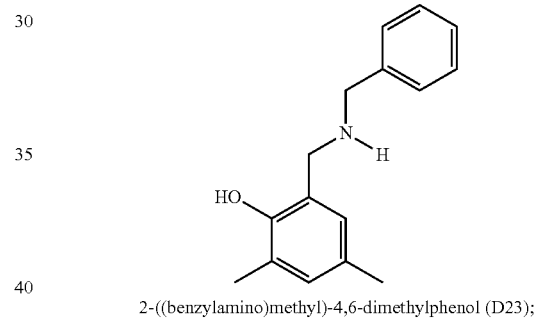
2-((benzylamino)methyl)-4,6-dimethylphenol (D23);
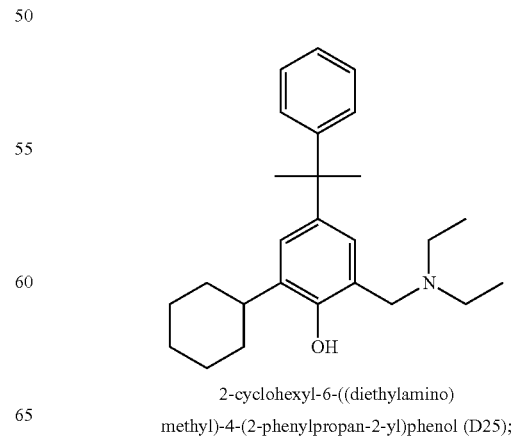
2-cyclohexyl-6-((diethylamino)methyl)-4-(2-phenylpropan-2-yl)phenol (D25);

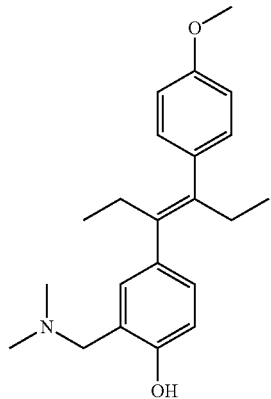 [SMILES: CC/C(=C(/CC)c1ccc(O)c(CN(C)C)c1)c1ccc(OC)cc1]
(E)-2-((dimethylamino)methyl)-4-(4-(4-methoxyphenyl)hex-3-en-3-yl)phenol (D28); and
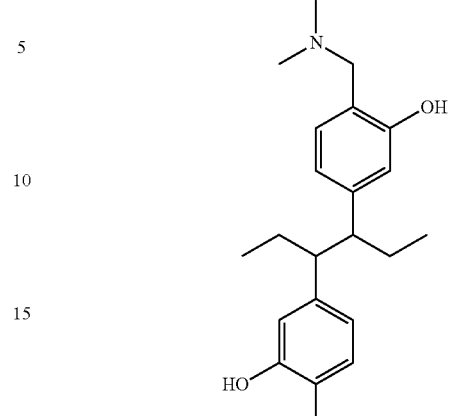
5,5'-(hexane-3,4-diyl)bis(2-((dimethylamino)methyl)phenol) (D30);
or a salt, hydrate or solvate thereof.
* * * * *

UNITED STATES PATENT AND TRADEMARK OFFICE
CERTIFICATE OF CORRECTION

PATENT NO. : 8,367,078 B2
APPLICATION NO. : 12/663521
DATED : February 5, 2013
INVENTOR(S) : Peter P. Sayeski et al.

Page 1 of 1

It is certified that error appears in the above-identified patent and that said Letters Patent is hereby corrected as shown below:

In the Specification

At Column 1, Line 12, beneath heading "STATEMENT OF RIGHTS TO INVENTIONS MADE UNDER FEDERALLY SPONSORED RESEARCH", please delete the below paragraph, at Lines 16-18, as follows:
"This work was supported in part by a National Institutes of Health/NHLBI Grant, Grant No. R01 HL067277. The government may have certain rights in the invention."

And insert:
-- This invention was made with government support under Grant No. HL067277 awarded by the National Institutes of Health. The government has certain rights in the invention. --

Signed and Sealed this
Twenty-third Day of February, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 10

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gttcttttga aagtccta                                                    18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgcttagcc actccaag                                                    18

<210> SEQ ID NO 3
<211> LENGTH: 288
<212> TYPE: PRT
<213> ORGANISM: Homo sapiens

<400> SEQUENCE: 3

Pro Thr Ile Phe Glu Glu Arg His Leu Lys Tyr Ile Ser Gln Leu Gly
 1               5                  10                  15

Lys Gly Asn Phe Gly Ser Val Glu Leu Cys Arg Tyr Asp Pro Leu Gly
                20                  25                  30

Asp Asn Thr Gly Ala Leu Val Ala Val Lys Gln Leu Gln His Ser Gly
            35                  40                  45

Pro Asp Gln Gln Arg Asp Phe Gln Arg Glu Ile Gln Ile Leu Lys Ala
        50                  55                  60

Leu His Ser Asp Phe Ile Val Lys Tyr Arg Gly Val Ser Tyr Gly Pro
 65                  70                  75                  80

Gly Arg Pro Glu Leu Arg Leu Val Met Glu Tyr Leu Pro Ser Gly Cys
                85                  90                  95

Leu Arg Asp Phe Leu Gln Arg His Arg Ala Arg Leu Asp Ala Ser Arg
                100                 105                 110

Leu Leu Leu Tyr Ser Ser Gln Ile Cys Lys Gly Met Glu Tyr Leu Gly
            115                 120                 125

Ser Arg Arg Cys Val His Arg Asp Leu Ala Ala Arg Asn Ile Leu Val
        130                 135                 140

Glu Ser Glu Ala His Val Lys Ile Ala Asp Phe Gly Leu Ala Lys Leu
145                 150                 155                 160

Leu Pro Leu Asp Lys Asp Val Val Arg Glu Pro Gly Gln Ser Pro Ile
                165                 170                 175

Phe Trp Tyr Ala Pro Glu Ser Leu Ser Asp Asn Ile Phe Ser Arg Gln
                180                 185                 190

Ser Asp Val Trp Ser Phe Gly Val Val Leu Tyr Glu Leu Phe Thr Tyr
            195                 200                 205

Cys Asp Lys Ser Cys Ser Pro Ser Ala Glu Phe Leu Arg Met Met Gly
        210                 215                 220

```
Cys Glu Arg Asp Val Pro Ala Leu Cys Arg Leu Leu Glu Leu Leu Glu
225                 230                 235                 240

Glu Gly Gln Arg Leu Pro Ala Pro Pro Ala Cys Pro Ala Glu Val His
            245                 250                 255

Glu Leu Met Lys Leu Cys Trp Ala Pro Ser Pro Gln Asp Arg Pro Ser
        260                 265                 270

Phe Ser Ala Leu Gly Pro Gln Leu Asp Met Leu Trp Ser Gly Ser Arg
    275                 280                 285

<210> SEQ ID NO 4
<211> LENGTH: 289
<212> TYPE: PRT
<213> ORGANISM: Peptococcus aerogenes

<400> SEQUENCE: 4

Pro Thr Gln Phe Glu Glu Arg His Leu Lys Phe Leu Gln Gln Leu Gly
1               5                   10                  15

Lys Gly Asn Phe Gly Ser Val Glu Met Cys Arg Tyr Asp Pro Leu Gln
            20                  25                  30

Asp Asn Thr Gly Glu Val Val Ala Val Lys Lys Leu Gln His Ser Thr
        35                  40                  45

Glu Glu His Leu Arg Asp Phe Glu Arg Glu Ile Glu Ile Leu Lys Ser
    50                  55                  60

Leu Gln His Asp Asn Ile Val Lys Tyr Lys Gly Val Cys Tyr Ser Ala
65                  70                  75                  80

Gly Arg Arg Asn Leu Arg Leu Ile Met Glu Tyr Leu Pro Tyr Gly Ser
                85                  90                  95

Leu Arg Asp Tyr Leu Gln Lys His Lys Glu Arg Ile Asp His Lys Lys
            100                 105                 110

Leu Leu Gln Tyr Thr Ser Gln Ile Cys Lys Gly Met Glu Tyr Leu Gly
        115                 120                 125

Thr Lys Arg Tyr Ile His Arg Asp Leu Ala Thr Arg Asn Ile Leu Val
    130                 135                 140

Glu Asn Glu Asn Arg Val Lys Ile Gly Asp Phe Gly Leu Thr Lys Val
145                 150                 155                 160

Leu Pro Gln Asp Lys Glu Tyr Tyr Lys Val Lys Glu Pro Gly Glu Ser
                165                 170                 175

Pro Ile Phe Trp Tyr Ala Pro Gln Ser Leu Thr Glu Ser Lys Phe Ser
            180                 185                 190

Val Ala Ser Asp Val Trp Ser Phe Gly Val Val Leu Tyr Glu Leu Phe
        195                 200                 205

Thr Tyr Ile Glu Lys Ser Lys Ser Pro Pro Val Glu Phe Met Arg Met
    210                 215                 220

Ile Gly Asn Asp Lys Gln Gly Gln Met Ile Val Phe His Leu Ile Glu
225                 230                 235                 240

Leu Leu Lys Ser Asn Gly Arg Leu Pro Arg Pro Glu Gly Cys Pro Asp
                245                 250                 255

Glu Ile Tyr Val Ile Met Thr Glu Cys Trp Asn Asn Asn Val Ser Gln
            260                 265                 270

Arg Pro Ser Phe Arg Asp Leu Ser Phe Gly Trp Ile Lys Cys Gly Thr
        275                 280                 285

Val

<210> SEQ ID NO 5
<211> LENGTH: 11
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 5
gagtcagcyy y                                                            11

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtggagagga g                                                            11

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aaaattccat a                                                            11

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Leu Gly Lys
  1

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Met Glu Tyr Leu Pro Tyr Gly
  1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Gly Asp Phe
  1
```